US008202831B2

(12) United States Patent
Lant et al.

(10) Patent No.: US 8,202,831 B2
(45) Date of Patent: Jun. 19, 2012

(54) DETERGENT COMPOSITION COMPRISING A VARIANT OF A FAMILY 44 XYLOGLUCANASE

(75) Inventors: Neil Joseph Lant, Newcastle upon Tyne (GB); Werner Besenmatter, Søborg (DK); Esben Peter Friis, Herlev (DK); Keith Gibson, Bagsvaerd (DK); Frank Winther Rasmussen, Roskilde (DK); Michael Skjøt, Jyllinge (DK)

(73) Assignee: The Procter & Gamble Company, Cincinnati, OH (US)

( * ) Notice: Subject to any disclaimer, the term of this patent is extended or adjusted under 35 U.S.C. 154(b) by 196 days.

(21) Appl. No.: 12/478,793

(22) Filed: Jun. 5, 2009

(65) Prior Publication Data

US 2009/0312221 A1 Dec. 17, 2009

Related U.S. Application Data

(60) Provisional application No. 61/131,227, filed on Jun. 6, 2008, provisional application No. 61/114,519, filed on Nov. 14, 2008.

(51) Int. Cl.
*C11D 3/00* (2006.01)
*C11D 3/22* (2006.01)
*C11D 3/386* (2006.01)
*C12N 9/24* (2006.01)
*C07H 21/04* (2006.01)

(52) U.S. Cl. ........ 510/320; 510/473; 510/530; 435/200; 536/23.2

(58) Field of Classification Search .................. None
See application file for complete search history.

(56) References Cited

U.S. PATENT DOCUMENTS

| | | | |
|---|---|---|---|
| 4,963,655 A | 10/1990 | Kinder et al. | |
| 5,159,060 A | 10/1992 | Kinder et al. | |
| 5,223,409 A | 6/1993 | Ladner et al. | |
| 5,354,491 A | 10/1994 | Bjorkquist et al. | |
| 5,431,842 A | 7/1995 | Panandiker et al. | |
| 5,442,100 A | 8/1995 | Bjorkquist et al. | |
| 5,472,628 A | 12/1995 | Panandiker et al. | |
| 5,488,157 A | 1/1996 | Bjorkquist et al. | |
| 5,576,282 A | 11/1996 | Miracle et al. | |
| 5,580,486 A | 12/1996 | Labeque et al. | |
| 5,834,415 A | 11/1998 | Nielsen et al. | |
| 5,916,796 A * | 6/1999 | Jorgensen et al. | 510/321 |
| 6,165,966 A | 12/2000 | McIver et al. | |
| 6,214,598 B1 | 4/2001 | Dalboege et al. | |
| 6,268,197 B1 | 7/2001 | Schulein et al. | |
| 6,306,812 B1 | 10/2001 | Perkins et al. | |
| 6,326,348 B1 | 12/2001 | Vinson et al. | |
| 6,682,924 B1 | 1/2004 | Sierkstra et al. | |
| 6,815,192 B2 * | 11/2004 | Schnorr et al. | 435/210 |
| 6,893,845 B1 | 5/2005 | Huse | |
| 7,208,459 B2 | 4/2007 | Sadlowski et al. | |
| 7,361,736 B2 | 4/2008 | Schnorr et al. | |
| 2003/0017955 A1 * | 1/2003 | Forth et al. | 510/296 |
| 2004/0171154 A1 | 9/2004 | Storici et al. | |
| 2006/0234895 A1 | 10/2006 | Souter et al. | |
| 2008/0015135 A1 | 1/2008 | De Buzzaccarini et al. | |
| 2008/0139442 A1 | 6/2008 | Lang | |
| 2008/0153983 A1 | 6/2008 | Boeckh et al. | |
| 2008/0261833 A1 | 10/2008 | Stemmer et al. | |
| 2009/0036641 A1 | 2/2009 | Lang et al. | |
| 2009/0172895 A1 | 7/2009 | Lant et al. | |
| 2009/0176291 A1 | 7/2009 | Boutique et al. | |
| 2009/0176680 A1 | 7/2009 | Patterson et al. | |
| 2009/0176682 A1 | 7/2009 | Boutique et al. | |

FOREIGN PATENT DOCUMENTS

| | | |
|---|---|---|
| WO | WO 95/17413 A1 | 6/1995 |
| WO | WO 01/62903 A1 | 8/2001 |
| WO | WO 03/095658 A1 | 11/2003 |
| WO | WO 2007/138054 A1 | 12/2007 |
| WO | WO 2007/149806 A1 | 12/2007 |
| WO | WO 2008/110318 A2 | 9/2008 |

OTHER PUBLICATIONS

Vincken, Jean-Paul, et al., Substrate specificity of endoglucanases: what determines xyloglucanase activity?, Carbohydrate Research, 1997, pp. 299-310, vol. 298, No. 4.
Henrissat, Bernard, A classification of glycosyl hydrolases based on amino acid sequence similarities, Biochem. J., 1991, pp. 309-316, vol. 280.
Henrissat, Bernard, et al., New families in the classification of glycosyl hydrolases based on amino acid sequence similarities, Biochem. J., 1993, pp. 781-788, vol. 293.
Needleman, Saul B., et al., A General Method Applicable to the Search for Similarities in the Amino Acid Sequence of Two Proteins, J. Mol. Biol., 1970, pp. 443-453, vol. 48.
Rice, Peter, et al., Emboss & Emboss version of Blosum 62: The European Molecular Biology Open Software Suite, Jun. 2000, pp. 276-277, vol. 16, No. 6.
Thompson, Julie D., et al., Clustal W: improving the sensitivity of progressive multiple sequence alignment through sequence weighting, position-specific gap penalties and weight matrix choice, Nucleic Acids Research, 1994, pp. 4673-4680, vol. 22, No. 22.
Nilsson, Björn, et al., Immobilization and purification of enzymes with staphylococcal protein A gene fusion vectors, The EMBO Journal, 1985, pp. 1075-1080, vol. 4, No. 4.
Ford, Clark F., et al., Fusion Tails for the Recovery and Purification of Recombinant Proteins, Protein Expression and Purification, 1991, pp. 95-107, vol. 2.
Hilton, Douglas J, et al., Saturation Mutagenesis of the WSXWS Motif of the Erythropoietin Receptor, The Journal of Biological Chemistry, 1996, pp. 4699-4708, vol. 271, No. 9.
De Vos, Abraham M., et al., Human Growth Hormone and Extracellular Domain of its Receptor: Crystal Structure of the Complex, Science, Jan. 17, 1992, pp. 306-312, vol. 255.

(Continued)

*Primary Examiner* — Anand Desai
*Assistant Examiner* — Iqbal H Chowdhury
(74) *Attorney, Agent, or Firm* — Melissa G Krasovec; James F McBride; Leonard W Lewis

(57) ABSTRACT

The present invention relates to detergent compositions comprising a variant of a parent xyloglucanase.

16 Claims, 2 Drawing Sheets

OTHER PUBLICATIONS

Smith, Lorna J., et al., Human Interleukin 4 the Solution Structure of a Four-Helix Bundle Protein, J. Mol. Biol., 1992, pp. 899-904, vol. 224.

Wlodaver, Alexander, et al., Crystal structure of human recombinant interleukin-4 at 2.25 Å resolution, FEBS Letters, Aug. 1992, pp. 59-64, vol. 309, No. 1.

Kitago, Yu, et al., Crystal Structure of Cel44A, a Glycoside Hydrolase Family 44 Endoglucanase from *Clostridium thermocellum*, The Journal of Biological Chemistry, 2007, pp. 35703-35711, vol. 282, No. 49.

Bolton, E. T., et al., A General Method for the Isolation of RNA Complementary to DNA, Proceedings of the National Academy of Sciences USA, 1962, pp. 1390-1397, vol. 48.

Tian, J., et al., Accurate multiplex gene synthesis from programmable DNA microchips, Nature, Dec. 2004, pp. 1050-1054, vol. 432.

Scherer, Stewart, et al., Replacement of chromosome segments with altered DNA sequences contructed in vitro, Proc. Natl. Acad. Sci. USA, Oct. 1979, pp. 4951-4955, vol. 76, No. 10.

Barton, M. C., et al., Site-directed, recombination-mediated mutagenesis of a complex gene locus, Nucleic Acids Research, 1990, pp. 7349-7355, vol. 18, No. 24.

Melnikov, A., et al., Random mutagenesis by recombinational capture of PCR products in *Bacillus subtilis* and *Acinetobacter calcoaceticus*, Nucleic Acids Research, 1999, pp. 1056-1062, vol. 27, No. 4.

Storici, F., et al., In vivo site-directed mutagenesis using oligonucleotides, Nature Biotechnology, Aug. 2001, pp. 773-776, vol. 19.

Kren, B. T., et al., In vivo site-directed mutagenesis of the *factor IX* gene by chimeric RNA/DNA oligonucleotides, Nature Medicine, Mar. 1998, pp. 285-290, vol. 4, No. 3.

Calissano, M., et al., In vivo site-directed mutagenesis of *Neurospora crassa beta-tubulin* gene by spheroplasts transformation with oligonucleotides, Fungal Genet. Newslett., 1996, pp. 15-16, vol. 43.

Reidhaar-Olson, J. F., et al., Combinatorial Cassette Mutagenesis as a Probe of the Informational Content of Protein Sequences, Science, 1988, pp. 53-57, vol. 241.

Bowie, James U., et al., Identifying determinants of folding and activity for a protein of unknown structure, Proc. Natl. Acad. Sci. USA, 1989, pp. 2152-2156, vol. 86.

Enzymes in Detergency, 1997, published by Marcel Dekker, pp. 139-140.

International Search Report, International Application No. PCT/US2009/045770, Date of mailing Sep. 17, 2009, 3 pages.

* cited by examiner

Figure 1B

SEQUENCE LISTING

<160> NUMBER OF SEQ ID NOS: 7

<210> SEQ ID NO 1
<211> LENGTH: 1695
<212> TYPE: DNA
<213> ORGANISM: Paenibacillus polymyxa

<400> SEQUENCE: 1

```
atgaagaaac cgttggggaa aattgtcgca agcaccgcac tactcatttc tgttgctttt      60
agttcatcga tcgcatcggc tgtagttcac ggtcaaacgg caaagactat tactattaaa     120
gtagatacat tcaaggatcg taagcctatt agcccttata tatacggtac aaatcaggat     180
ttggcaggcg atgaaaatat ggctgccaga cgacttggtg caaccgaat gaccggatac     240 aactgggaaa acaatatgtc caatgcagga agtgactggc agcaatctag cgataactat     300
ttatgcagta atggtggcct gacacaagcc gaatgtgaaa agccaggagc ggtgacgact     360
tcgtttcatg accaatcgct gaagcttggc acttattctt tagttacgtt gccgatggcc     420
ggttatgtgg ctaaggatgg aaacggaagt gtgcaggaaa gcgaaaaggc cccttccgct     480
cgttggaatc aggtcgtaaa cgccaaaaat gcaccgttcc aactacagcc tgatctgaat     540
gacaatcggg tctatgtgga tgagttcgtc cattttttag tgaacaagta cggcactgct     600
```

```
tcaacaaagg cgggggtgaa aggatatgcc ctcgacaatg aacccgctct ctggtcgcat    660
acgcacccac gcattcatgg tgaaaaagtc ggagcgaaag agttggtaga ccggtcagtc    720
agtttatcca aagctgtgaa agcgattgac gcggggggcag aggttttttgg cccggttctt   780 tacggatttg cgcctataa agatcttcaa actgcacctg attgggactc tgtaaaaggc     840
aattatagct ggttcgtaga ctattacctg gatcaaatgc gccttagctc gcaagtcgaa    900
ggcaagagat tgctggatgt attcgacgta cactggtatc ccgaagcgat gggcggaggc    960
atacgaatta cgaatgaggt aggcaatgac gaaacgaaga aagccagaat gcaggcacct   1020
cgcaccttgt gggaccccgac ctataaggaa gatagttgga tcgctcaatg aacagcgag   1080 ttttttgccca tactacctcg attgaagcag tcggtggata aatattatcc gggaaccaag  1140
ctggcaatga ccgagtatag ctatggcggc gaaaatgata tttccggcgg gattgcgatg  1200
accgatgtgc tgggtatctt gggcaaaaat gatgtttata tggcaaacta ctggaagcta  1260
aaggatggtg tcaacaacta cgttagtgcc gcttacaagc tttatcgcaa ttatgacgga  1320
aaaaactcta ctttcggtga taccagtgtt agtgcgcaaa catcggatat tgtcaatagc  1380
tcggtccatg cttctgtaac gaatgcatcc gacaaagaac tgcatctcgt tgtcatgaat  1440
aaaagcatgg acagcgcatt cgacgcccaa tttgatcttt ccggcgcgaa gacttacatt  1500
tccggtaaag tatgggggtt cgataaaaac agctcgcaaa ttaaagaagc agcgccaatc  1560
acgcaaattt caggcaaccg ttttacttat accgtaccgc ctttgacggc atatcacatt  1620
gtgctgacta ctggcaatga cacgtctcca gtgtaaggcg tacttgtttg gggaaccgag  1680
ccgacagcta attaa                                                    1695
```

<210> SEQ ID NO 2
<211> LENGTH: 551
<212> TYPE: PRT
<213> ORGANISM: Paenibacillus polymyxa

<400> SEQUENCE: 2

```
Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Val Val His Gly Gln
                20                  25                  30

Thr Ala Lys Thr Ile Thr Ile Lys Val Asp Thr Phe Lys Asp Arg Lys
            35                  40                  45

Pro Ile Ser Pro Tyr Ile Tyr Gly Thr Asn Gln Asp Leu Ala Gly Asp
        50                  55                  60

Glu Asn Met Ala Ala Arg Arg Leu Gly Gly Asn Arg Met Thr Gly Tyr
65                  70                  75                  80

Asn Trp Glu Asn Asn Met Ser Asn Ala Gly Ser Asp Trp Gln Gln Ser
                85                  90                  95

Ser Asp Asn Tyr Leu Cys Ser Asn Gly Gly Leu Thr Gln Ala Glu Cys
                100                 105                 110

Glu Lys Pro Gly Ala Val Thr Thr Ser Phe His Asp Gln Ser Leu Lys
            115                 120                 125

Leu Gly Thr Tyr Ser Leu Val Thr Leu Pro Met Ala Gly Tyr Val Ala
        130                 135                 140

Lys Asp Gly Asn Gly Ser Val Gln Glu Ser Lys Ala Pro Ser Ala
145                 150                 155                 160

Arg Trp Asn Gln Val Val Asn Ala Lys Asn Ala Pro Phe Gln Leu Gln
                165                 170                 175

Pro Asp Leu Asn Asp Asn Arg Val Tyr Val Asp Glu Phe Val His Phe
```

```
            180                 185                 190
Leu Val Asn Lys Tyr Gly Thr Ala Ser Thr Lys Ala Gly Val Lys Gly
            195                 200                 205

Tyr Ala Leu Asp Asn Glu Pro Ala Leu Trp Ser His Thr His Pro Arg
            210                 215                 220

Ile His Gly Glu Lys Val Gly Ala Lys Glu Leu Val Asp Arg Ser Val
225                 230                 235                 240

Ser Leu Ser Lys Ala Val Lys Ala Ile Asp Ala Gly Ala Glu Val Phe
            245                 250                 255

Gly Pro Val Leu Tyr Gly Phe Gly Ala Tyr Lys Asp Leu Gln Thr Ala
            260                 265                 270

Pro Asp Trp Asp Ser Val Lys Gly Asn Tyr Ser Trp Phe Val Asp Tyr
            275                 280                 285

Tyr Leu Asp Gln Met Arg Leu Ser Ser Gln Val Glu Gly Lys Arg Leu
            290                 295                 300

Leu Asp Val Phe Asp Val His Trp Tyr Pro Glu Ala Met Gly Gly Gly
305                 310                 315                 320

Ile Arg Ile Thr Asn Glu Val Gly Asn Asp Glu Thr Lys Lys Ala Arg
            325                 330                 335

Met Gln Ala Pro Arg Thr Leu Trp Asp Pro Thr Tyr Lys Glu Asp Ser
            340                 345                 350

Trp Ile Ala Gln Trp Asn Ser Glu Phe Leu Pro Ile Leu Pro Arg Leu
            355                 360                 365

Lys Gln Ser Val Asp Lys Tyr Tyr Pro Gly Thr Lys Leu Ala Met Thr
            370                 375                 380

Glu Tyr Ser Tyr Gly Gly Glu Asn Asp Ile Ser Gly Gly Ile Ala Met
385                 390                 395                 400

Thr Asp Val Leu Gly Ile Leu Gly Lys Asn Asp Val Tyr Met Ala Asn
            405                 410                 415

Tyr Trp Lys Leu Lys Asp Gly Val Asn Asn Tyr Val Ser Ala Ala Tyr
            420                 425                 430

Lys Leu Tyr Arg Asn Tyr Asp Gly Lys Asn Ser Thr Phe Gly Asp Thr
            435                 440                 445

Ser Val Ser Ala Gln Thr Ser Asp Ile Val Asn Ser Ser Val His Ala
            450                 455                 460

Ser Val Thr Asn Ala Ser Asp Lys Glu Leu His Leu Val Val Met Asn
465                 470                 475                 480

Lys Ser Met Asp Ser Ala Phe Asp Ala Gln Phe Asp Leu Ser Gly Ala
            485                 490                 495

Lys Thr Tyr Ile Ser Gly Lys Val Trp Gly Phe Asp Lys Asn Ser Ser
            500                 505                 510

Gln Ile Lys Glu Ala Ala Pro Ile Thr Gln Ile Ser Gly Asn Arg Phe
            515                 520                 525

Thr Tyr Thr Val Pro Pro Leu Thr Ala Tyr His Ile Val Leu Thr Thr
            530                 535                 540

Gly Asn Asp Thr Ser Pro Val
545                 550

<210> SEQ ID NO 3
<211> LENGTH: 524
<212> TYPE: PRT
<213> ORGANISM: Paenibacillus polymyxa

<400> SEQUENCE: 3

Val Val His Gly Gln Thr Ala Lys Thr Ile Thr Ile Lys Val Asp Thr
```

-continued

```
1               5                   10                  15
Phe Lys Asp Arg Lys Pro Ile Ser Pro Tyr Ile Tyr Gly Thr Asn Gln
                20                  25                  30

Asp Leu Ala Gly Asp Glu Asn Met Ala Ala Arg Arg Leu Gly Gly Asn
            35                  40                  45

Arg Met Thr Gly Tyr Asn Trp Glu Asn Asn Met Ser Asn Ala Gly Ser
        50                  55                  60

Asp Trp Gln Gln Ser Ser Asp Asn Tyr Leu Cys Ser Asn Gly Gly Leu
65                  70                  75                  80

Thr Gln Ala Glu Cys Glu Lys Pro Gly Ala Val Thr Thr Ser Phe His
                85                  90                  95

Asp Gln Ser Leu Lys Leu Gly Thr Tyr Ser Leu Val Thr Leu Pro Met
            100                 105                 110

Ala Gly Tyr Val Ala Lys Asp Gly Asn Gly Ser Val Gln Glu Ser Glu
        115                 120                 125

Lys Ala Pro Ser Ala Arg Trp Asn Gln Val Val Asn Ala Lys Asn Ala
130                 135                 140

Pro Phe Gln Leu Gln Pro Asp Leu Asn Asp Asn Arg Val Tyr Val Asp
145                 150                 155                 160

Glu Phe Val His Phe Leu Val Asn Lys Tyr Gly Thr Ala Ser Thr Lys
                165                 170                 175

Ala Gly Val Lys Gly Tyr Ala Leu Asp Asn Glu Pro Ala Leu Trp Ser
            180                 185                 190

His Thr His Pro Arg Ile His Gly Glu Lys Val Gly Ala Lys Glu Leu
        195                 200                 205

Val Asp Arg Ser Val Ser Leu Ser Lys Ala Val Lys Ala Ile Asp Ala
210                 215                 220

Gly Ala Glu Val Phe Gly Pro Val Leu Tyr Gly Phe Gly Ala Tyr Lys
225                 230                 235                 240

Asp Leu Gln Thr Ala Pro Asp Trp Asp Ser Val Lys Gly Asn Tyr Ser
                245                 250                 255

Trp Phe Val Asp Tyr Tyr Leu Asp Gln Met Arg Leu Ser Ser Gln Val
            260                 265                 270

Glu Gly Lys Arg Leu Leu Asp Val Phe Asp Val His Trp Tyr Pro Glu
        275                 280                 285

Ala Met Gly Gly Gly Ile Arg Ile Thr Asn Glu Val Gly Asn Asp Glu
290                 295                 300

Thr Lys Lys Ala Arg Met Gln Ala Pro Arg Thr Leu Trp Asp Pro Thr
305                 310                 315                 320

Tyr Lys Glu Asp Ser Trp Ile Ala Gln Trp Asn Ser Glu Phe Leu Pro
                325                 330                 335

Ile Leu Pro Arg Leu Lys Gln Ser Val Asp Lys Tyr Tyr Pro Gly Thr
            340                 345                 350

Lys Leu Ala Met Thr Glu Tyr Ser Tyr Gly Gly Glu Asn Asp Ile Ser
        355                 360                 365

Gly Gly Ile Ala Met Thr Asp Val Leu Gly Ile Leu Gly Lys Asn Asp
370                 375                 380

Val Tyr Met Ala Asn Tyr Trp Lys Leu Lys Asp Gly Val Asn Asn Tyr
385                 390                 395                 400

Val Ser Ala Ala Tyr Lys Leu Tyr Arg Asn Tyr Asp Gly Lys Asn Ser
                405                 410                 415

Thr Phe Gly Asp Thr Ser Val Ser Ala Gln Thr Ser Asp Ile Val Asn
            420                 425                 430
```

```
Ser Ser Val His Ala Ser Val Thr Asn Ala Ser Asp Lys Glu Leu His
        435                 440                 445
Leu Val Val Met Asn Lys Ser Met Asp Ser Ala Phe Asp Ala Gln Phe
    450                 455                 460
Asp Leu Ser Gly Ala Lys Thr Tyr Ile Ser Gly Lys Val Trp Gly Phe
465                 470                 475                 480
Asp Lys Asn Ser Gln Ile Lys Glu Ala Ala Pro Ile Thr Gln Ile
                485                 490                 495
Ser Gly Asn Arg Phe Thr Tyr Thr Val Pro Pro Leu Thr Ala Tyr His
                500                 505                 510
Ile Val Leu Thr Thr Gly Asn Asp Thr Ser Pro Val
        515                 520

<210> SEQ ID NO 4
<211> LENGTH: 1590
<212> TYPE: DNA
<213> ORGANISM: Paenibacillus polymyxa

<400> SEQUENCE: 4
gtagttcacg gtcaaacggc aaagactgtt accattaaag tcgatacatc caaggatcgt      60
aagcctatta gcccttatat ttacggtacg aatcaggagt tggcaggcga tgagaatctg     120
actgccagac gacttggtgg caatcgaatg accggatata actgggaaaa caatatgtcc     180
aatgcaggaa gcgactggat gcagtccagc gatagctatt tatgcgacaa cgccggattg     240
acaaaagccg aatgtgaaaa gccaggtgcg gtggcaacct cgtttcacga tcaatcgctg     300
aagcagggca catattcttt agtcacactg ccgatggccg ttatgtggc caaggatgga     360
aacggaagtg tgcaggaaag cgaaaaggct ccttccgctc ggtggaatga ggtcgtaaac     420
gctaaaaatg cgccgtttca attgcagcct gatctgaaag acaatcaggt ttatgcggat     480
gaattcgtca cttttttagt gaaaaagtac ggcgttgctt caacaaaaac gggcgtgaaa     540
ggatactcgc tcgacaatga acccgctctc tggtcgcata cgcatccgcg cattcatggt     600
gaaaaggtcg gagcgaaaga gttggtagac cggtcggtaa gtttatccaa agccgctaag     660
gcggttgacg cgggtgcgga aatttttggg cccgttcttt acggttttgg cgcctataaa     720
gatcttcaaa ctgcacctga ttggaactct gtaaaaggca actacagctg gttcgtggac     780
tattacctcg atcaaatgcg cctcagctcg caagccgaag caagagatt gctggatgtc     840
ttcgatgtac actggtatcc tgaagcgatg ggcggaggca tacgaattac aaatgaggta     900
ggcaacgacg aaacgaagaa agccagaatg caagcgcctc gtactttgtg ggatccgacc     960
tacaaggaag atagctggat cgctcaatgg aacagtgaat tcttgccttt actgcctcga    1020
ttaaagcagt cggtggataa gtattacccg ggaaccaagc tggctttgac tgagtatagc    1080
tatggtggcg aaaatgatat ttccggcggt atcgctatgg ccgatgtgct gggcatcttg    1140
ggcaaaaacg acgtttatat ggcaaactac tggaagttaa aggatggtgc aacaactac     1200
gttagtgccg cttacaagct ttaccgcaat tatgacggaa aaagctctac tttcggtgat    1260
atcagcgttc atgcgcaaac gtcggatatt gttaatagct cggtgcatgc ttccgtaacg    1320
gatgcatcct acaaagaact gcacctcgtt gtcatgaata aaagcatgga cagtgcattc    1380
gacgcccaat ttgatctttc cggcgagacg acttacggtt ccgtaaagt atggggtttc     1440
gacaaaaata gctcgcaaat taaggaagca gcgccaatca cscaaatttc aggcaaccgy    1500
tttacctata cagtaccgcc tttgacggct tatcacatcg tgttgactgc cggcaatgat    1560
acacctgtag aaaatcctga aagctttgcg                                     1590
```

<210> SEQ ID NO 5
<211> LENGTH: 530
<212> TYPE: PRT
<213> ORGANISM: Paenibacillus polymyxa

<400> SEQUENCE: 5

```
Val Val His Gly Gln Thr Ala Lys Thr Val Thr Ile Lys Val Asp Thr
  1               5                  10                  15
Ser Lys Asp Arg Lys Pro Ile Ser Pro Tyr Ile Tyr Gly Thr Asn Gln
                 20                  25                  30
Glu Leu Ala Gly Asp Glu Asn Leu Thr Ala Arg Arg Leu Gly Gly Asn
             35                  40                  45
Arg Met Thr Gly Tyr Asn Trp Glu Asn Asn Met Ser Asn Ala Gly Ser
 50                  55                  60
Asp Trp Met Gln Ser Ser Asp Ser Tyr Leu Cys Asp Asn Ala Gly Leu
 65                  70                  75                  80
Thr Lys Ala Glu Cys Glu Lys Pro Gly Ala Val Ala Thr Ser Phe His
                 85                  90                  95
Asp Gln Ser Leu Lys Gln Gly Thr Tyr Ser Leu Val Thr Leu Pro Met
            100                 105                 110
Ala Gly Tyr Val Ala Lys Asp Gly Asn Gly Ser Val Gln Glu Ser Glu
        115                 120                 125
Lys Ala Pro Ser Ala Arg Trp Asn Glu Val Val Asn Ala Lys Asn Ala
130                 135                 140
Pro Phe Gln Leu Gln Pro Asp Leu Lys Asp Asn Gln Val Tyr Ala Asp
145                 150                 155                 160
Glu Phe Val Asn Phe Leu Val Lys Lys Tyr Gly Val Ala Ser Thr Lys
                165                 170                 175
Thr Gly Val Lys Gly Tyr Ser Leu Asp Asn Glu Pro Ala Leu Trp Ser
            180                 185                 190
His Thr His Pro Arg Ile His Gly Glu Lys Val Gly Ala Lys Glu Leu
        195                 200                 205
Val Asp Arg Ser Val Ser Leu Ser Lys Ala Ala Lys Ala Val Asp Ala
210                 215                 220
Gly Ala Glu Ile Phe Gly Pro Val Leu Tyr Gly Phe Gly Ala Tyr Lys
225                 230                 235                 240
Asp Leu Gln Thr Ala Pro Asp Trp Asn Ser Val Lys Gly Asn Tyr Ser
                245                 250                 255
Trp Phe Val Asp Tyr Tyr Leu Asp Gln Met Arg Leu Ser Ser Gln Ala
            260                 265                 270
Glu Gly Lys Arg Leu Leu Asp Val Phe Asp Val His Trp Tyr Pro Glu
        275                 280                 285
Ala Met Gly Gly Gly Ile Arg Ile Thr Asn Glu Val Gly Asn Asp Glu
290                 295                 300
Thr Lys Lys Ala Arg Met Gln Pro Arg Thr Leu Trp Asp Pro Thr
305                 310                 315                 320
Tyr Lys Glu Asp Ser Trp Ile Ala Gln Trp Asn Ser Glu Phe Leu Pro
                325                 330                 335
Leu Leu Pro Arg Leu Lys Gln Ser Val Asp Lys Tyr Tyr Pro Gly Thr
            340                 345                 350
Lys Leu Ala Leu Thr Glu Tyr Ser Tyr Gly Gly Glu Asn Asp Ile Ser
        355                 360                 365
Gly Gly Ile Ala Met Ala Asp Val Leu Gly Ile Leu Gly Lys Asn Asp
370                 375                 380
```

```
Val Tyr Met Ala Asn Tyr Trp Lys Leu Lys Asp Gly Ala Asn Asn Tyr
385                 390                 395                 400

Val Ser Ala Ala Tyr Lys Leu Tyr Arg Asn Tyr Asp Gly Lys Ser Ser
            405                 410                 415

Thr Phe Gly Asp Ile Ser Val His Ala Gln Thr Ser Asp Ile Val Asn
        420                 425                 430

Ser Ser Val His Ala Ser Val Thr Asp Ala Ser Tyr Lys Glu Leu His
        435                 440                 445

Leu Val Val Met Asn Lys Ser Met Asp Ser Ala Phe Asp Ala Gln Phe
    450                 455                 460

Asp Leu Ser Gly Glu Thr Thr Tyr Gly Ser Gly Lys Val Trp Gly Phe
465                 470                 475                 480

Asp Lys Asn Ser Ser Gln Ile Lys Glu Ala Ala Pro Ile Thr Gln Ile
            485                 490                 495

Ser Gly Asn Arg Phe Thr Tyr Thr Val Pro Pro Leu Thr Ala Tyr His
        500                 505                 510

Ile Val Leu Thr Ala Gly Asn Asp Thr Pro Val Glu Asn Pro Glu Ser
        515                 520                 525

Phe Ala
    530

<210> SEQ ID NO 6
<211> LENGTH: 1575
<212> TYPE: DNA
<213> ORGANISM: Paenibacillus polymyxa

<400> SEQUENCE: 6
gtggttcacg gtcaaacggc aaagaccgtt accattaaag tcgatacatc caaggatcgt      60
aagcctatta gtccttatat atacggtacg aatcaggatt tggcaggcga tgaaaatctg     120
gctgccagac gacttggtgg caatcgaatg accggataca actgggaaaa taatatgtcc     180
aatgcgggaa gcgattggca gcaatccagc gataactttt tatgcaacaa tggtggcctg     240
acaaaagccg aatgtgaaaa gccgggagca gtgacgactt cgtttcatga tcaatcgctg     300
aagctgggcg cttattcttt agtcacgctg ccgatggccg ttatgtggc caaggatgga      360 aacggaagtg tgcaggaaag cgaacaggct ccttccgctc gttggaatca ggtcgtaaat     420
gccaaaaatg cgccgttcca actacagcct gatctgaatg acaatcaggt atatgcggat     480
gaattcgtca atttttagt gaaaaagtac ggcgctgctt caacaaaggc gggtgtgaaa     540
ggatatgcgc tcgacaatga acccgctctc tggtcgcata cgcatccgcg cattcatggt     600
gaaaaggtcg gagcgaaaga gttggtagac cggtcggtaa gtttatccaa agctgttaaa     660
gcggttgacg cgggtgcaga aattttgggc cggttctttt acggttttgg cgcctataca     720
gatcttcaaa ctgcacctga ttggaactct gtaaaaggca actatagctg gttcgtggac     780
tattacctgg atcaaatgcg cctcaactcg caagccgarg caagagatt gctggaygta      840 ttcgatgtgc actggtatcc cgaagcgatg ggcggaggca tacgaattac aaatgaggta     900
ggcaatgacg aaacgaagaa agccagaatg caggcgcctc gtactttgtg gacccgacc      960 tacaaggaag atagctggat cgctcaatgg aacagcgcat tcttgccttt actgcctcga    1020
ttgaagcagt cggtggacaa gtattacccg ggaaccaagc tggctttgac cgagtatagc    1080
tacggcggcg aaaatgatat ttccggcggt attgctatga ccgatgtgct gggcatcttg    1140
ggcaaaaacg acgtttatat ggcgaactat tggaagttaa aggatggtgc caacaactac    1200
gttagcgccg cttacaagct ttaccgcaat tatgacggaa aaaacgctac tttcggcgat    1260
```

-continued

```
atcagcgtta atgcgcaaac gtcggatatt gttaatagct cggtgcatgc ttccgtaacg    1320
gatgcatcct acaaagaact gcacctcatt gtcatgaata aaagcatgga cagcgcattc    1380
gacgcccaat tcgatctttc cggcgagacg acttacagtt ccggtaaaat atggggcttc    1440
gataaaaata gctcgcaaat taaggcagta gcgccaatca cgcaaatttc aggcaaccgc    1500
tttacctata cagtaccacc tttgacggct tatcacatcg tgttgactgc cgacaatgat    1560
acacctgtgc cataa                                                    1575
```

<210> SEQ ID NO 7
<211> LENGTH: 524
<212> TYPE: PRT
<213> ORGANISM: Paenibacillus polymyxa

<400> SEQUENCE: 7

```
Val Val His Gly Gln Thr Ala Lys Thr Val Thr Ile Lys Val Asp Thr
 1               5                  10                  15

Ser Lys Asp Arg Lys Pro Ile Ser Pro Tyr Ile Tyr Gly Thr Asn Gln
            20                  25                  30

Asp Leu Ala Gly Asp Glu Asn Leu Ala Ala Arg Arg Leu Gly Gly Asn
        35                  40                  45

Arg Met Thr Gly Tyr Asn Trp Glu Asn Asn Met Ser Asn Ala Gly Ser
    50                  55                  60

Asp Trp Gln Gln Ser Ser Asp Asn Phe Leu Cys Asn Asn Gly Gly Leu
65                  70                  75                  80

Thr Lys Ala Glu Cys Glu Lys Pro Gly Ala Val Thr Thr Ser Phe His
                85                  90                  95

Asp Gln Ser Leu Lys Leu Gly Ala Tyr Ser Leu Val Thr Leu Pro Met
           100                 105                 110

Ala Gly Tyr Val Ala Lys Asp Gly Asn Gly Ser Val Gln Glu Ser Glu
       115                 120                 125

Gln Ala Pro Ser Ala Arg Trp Asn Gln Val Val Asn Ala Lys Asn Ala
   130                 135                 140

Pro Phe Gln Leu Gln Pro Asp Leu Asn Asp Asn Gln Val Tyr Ala Asp
145                 150                 155                 160

Glu Phe Val Asn Phe Leu Val Lys Lys Tyr Gly Ala Ala Ser Thr Lys
                165                 170                 175

Ala Gly Val Lys Gly Tyr Ala Leu Asp Asn Glu Pro Ala Leu Trp Ser
           180                 185                 190

His Thr His Pro Arg Ile His Gly Glu Lys Val Gly Ala Lys Glu Leu
       195                 200                 205

Val Asp Arg Ser Val Ser Leu Ser Lys Ala Val Lys Ala Val Asp Ala
   210                 215                 220

Gly Ala Glu Ile Phe Gly Pro Val Leu Tyr Gly Phe Gly Ala Tyr Thr
225                 230                 235                 240

Asp Leu Gln Thr Ala Pro Asp Trp Asn Ser Val Lys Gly Asn Tyr Ser
                245                 250                 255

Trp Phe Val Asp Tyr Tyr Leu Asp Gln Met Arg Leu Asn Ser Gln Ala
           260                 265                 270

Glu Gly Lys Arg Leu Leu Asp Val Phe Asp Val His Trp Tyr Pro Glu
       275                 280                 285

Ala Met Gly Gly Gly Ile Arg Ile Thr Asn Glu Val Gly Asn Asp Glu
   290                 295                 300

Thr Lys Lys Ala Arg Met Gln Ala Pro Arg Thr Leu Trp Asp Pro Thr
305                 310                 315                 320
```

```
Tyr Lys Glu Asp Ser Trp Ile Ala Gln Trp Asn Ser Ala Phe Leu Pro
            325             330             335

Leu Leu Pro Arg Leu Lys Gln Ser Val Asp Lys Tyr Tyr Pro Gly Thr
            340             345             350

Lys Leu Ala Leu Thr Glu Tyr Ser Tyr Gly Gly Glu Asn Asp Ile Ser
            355             360             365

Gly Gly Ile Ala Met Thr Asp Val Leu Gly Ile Leu Gly Lys Asn Asp
        370             375             380

Val Tyr Met Ala Asn Tyr Trp Lys Leu Lys Asp Gly Ala Asn Asn Tyr
385             390             395             400

Val Ser Ala Ala Tyr Lys Leu Tyr Arg Asn Tyr Asp Gly Lys Asn Ala
            405             410             415

Thr Phe Gly Asp Ile Ser Val Asn Ala Gln Thr Ser Asp Ile Val Asn
            420             425             430

Ser Ser Val His Ala Ser Val Thr Asp Ala Ser Tyr Lys Glu Leu His
            435             440             445

Leu Ile Val Met Asn Lys Ser Met Asp Ser Ala Phe Asp Ala Gln Phe
        450             455             460

Asp Leu Ser Gly Glu Thr Thr Tyr Ser Ser Gly Lys Ile Trp Gly Phe
465             470             475             480

Asp Lys Asn Ser Ser Gln Ile Lys Ala Val Ala Pro Ile Thr Gln Ile
            485             490             495

Ser Gly Asn Arg Phe Thr Tyr Thr Val Pro Pro Leu Thr Ala Tyr His
            500             505             510

Ile Val Leu Thr Ala Asp Asn Asp Thr Pro Val Pro
            515             520
```

DETERGENT COMPOSITION COMPRISING A VARIANT OF A FAMILY 44 XYLOGLUCANASE

CROSS REFERENCE TO RELATED APPLICATION(S)

This application claims the benefit of U.S. Provisional Application No. 61/131,227, filed Jun. 6, 2008 and U.S. Provisional Application No. 61/114,519, filed Nov. 14, 2008.

FIELD OF THE INVENTION

The present invention relates to detergent compositions comprising a variant of a xyloglucanase belonging to family 44 of glycosyl hydrolases.

BACKGROUND OF THE INVENTION

Xyloglucan is a major structural polysaccharide in the primary (growing) cell wall of plants. Structurally, xyloglucans consists of a cellulose-like beta-1,4-linked glucose backbone which is frequently substituted with various side chains. Xyloglucan is believed to function in the primary wall of plants by cross-linking cellulose micro fibrils, forming a cellulose-xyloglucan network.

Xyloglucanses are capable of catalyzing the solubilization of xyloglucan to xyloglucan oligosaccharides. Some xyloglucanases only exhibit xyloglucanase activity, whereas others exhibit both xyloglucanase and cellulase activity. Xyloglucanses may be classified in EC 3.2.1.4 or EC. 3.2.1.151. Enzymes with xyloglucanase activity are for example described in Vincken et al. (1997) *Carbohydrate Research* 298(4):299-310, wherein three different endoglucanases EndoI, EndoV and EndoVI from *Trichoderma viride* (similar to *T. reesei*) are characterized. EndoI, EndoV and EndoVI belongs to family 5, 7 and 12 of glycosyl hydrolases, respectively, see Henrissat, B. et al. (1991, 1993). WO 94/14953 discloses a family 12 xyloglucanase (EG II) cloned from the fungus *Aspergillus aculeatus*. WO 99/02663 discloses family 12 and family 5 xyloglucanases cloned from *Bacillus licheniformis* and *Bacillus agaradhaerens*, respectively. WO 01/062903 discloses family 44 xyloglucanases.

In particular WO 99/02663 and WO 01/062903 suggest that xyloglucanases may be used in detergents.

It is an object of the present invention to provide a detergent composition comprising a variant of xyloglucanase belonging to family 44 of glycosyl hydrolases with improved properties compared to its parent enzyme.

SUMMARY OF THE INVENTION

The present invention relates to a detergent composition comprising isolated variants of a parent xyloglucanase, comprising an alteration at one or more (several) positions selected from the group consisting of position number 68, 123, 156, 118, 200, 129, 137, 193, 92, 83, 149, 34, 340, 332, 9, 76, 331, 310, 324, 498, 395, 366, 1, 374, 7, 140, 8, 14, 21, 211, 37, 45, 13, 78, 87, 436, 101, 104, 111, 306, 117, 119, 414, 139, 268, 142, 159, 164, 102, 168, 176, 180, 482, 183, 202, 206, 217, 4, 222, 19, 224, 228, 232, 2, 240, 244, 5, 247, 249, 328, 252, 259, 406, 267, 269, 275, 179, 166, 278, 281, 288, 298, 301, 18, 302, 165, 80, 303, 316, 169, 322, 120, 146, 342, 348, 147, 353, 380, 468, 382, 383, 38, 384, 389, 391, 10, 392, 396, 177, 397, 399, 409, 237, 413, 253, 415, 418, 40, 443, 445, 148, 449, 225, 450, 454, 3, 455, 456, 299, 461, 470, 204, 476, 488, 347, and 507, which position corresponds to a position in amino acid sequence SEQ ID NO:3 and wherein the alteration(s) are independently
i) an insertion of an amino acid downstream of the amino acid which occupies the position,
ii) deletion of the amino acid which occupies the position, or
iii) a substitution of the amino acid which occupies the position with a different amino acid; and
the parent xyloglucanase is a family 44 xyloglucanase; and the variant has xyloglucanase activity.

BRIEF DESCRIPTION OF FIGURES

The invention will be described in more detail below in conjunction with the following Figures, in which:

FIG. 1B represents the remainder of the resulting consensus sequences when an analysis is performed by aligning SEQ ID NO: 3, with SEQ ID NO: 5 and SEQ ID NO: 7 as well as with other sequences from the uniprot database which are 30% identical to the family 44 glycosyl hydrolase region of SEQ ID NO: 3.

DETAILED DESCRIPTION OF THE INVENTION

Figure 1A:
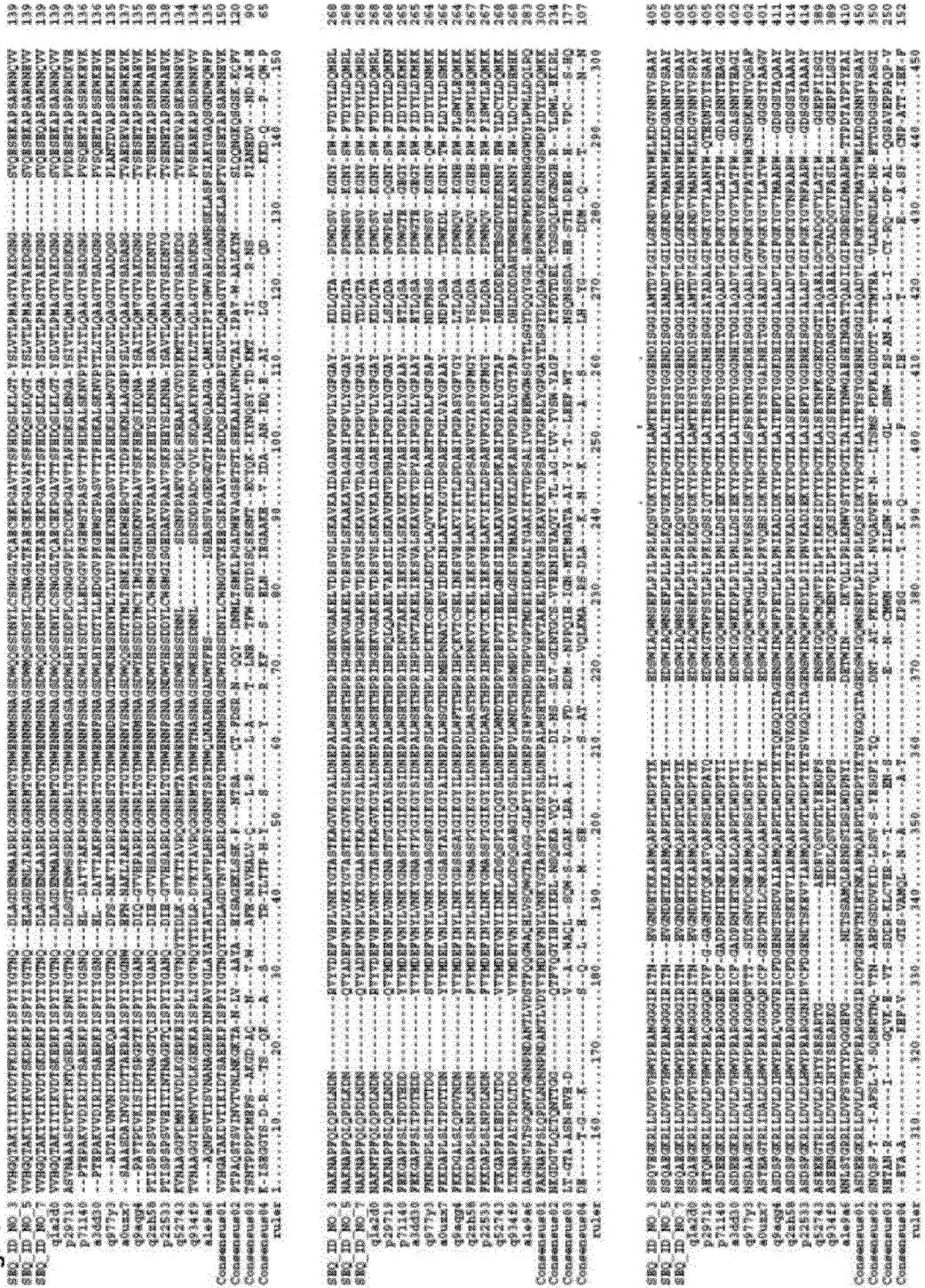
FIG. 1A represents the resulting consensus sequences when an analysis is performed by aligning SEQ ID NO: 3, with SEQ ID NO: 5 and SEQ ID NO: 7 as well as with other sequences from the uniprot database which are 30% identical to the family 44 glycosyl hydrolase region of SEQ ID NO: 3.

The present invention relates to a detergent composition comprising a variant of parent family 44 xyloglucanases, comprising an alteration, preferably in the form of a substitution and/or an insertion and/or a deletion at one or more (several) positions, where the numbering of the positions corresponds to the numbering of the positions of SEQ ID NO:3. The variants of the present invention have xyloglucanase activity and potentially also cellulolytic activity. The variants of the present invention have improved properties compared to the parental xyloglucanase. In one aspect, the variants have improved stability in liquid detergents, especially liquid laundry detergent compositions.

DEFINITIONS

Xyloglucanase activity: The term "xyloglucanase activity" is defined herein as an enzyme catalyzed hydrolysis of xyloglucan. The reaction involves endo hydrolysis of 1,4-beta-D-glucosidic linkages in xyloglucan. For purposes of the present invention, xyloglucanase activity is determined using AZCL-xyloglucan (from Megazyme) as the reaction substrate. The assay can be performed in several ways, e.g. as described in Example 2 of the present application or as described in WO 01/62903. One unit of xyloglucanase activity (XyloU) is defined by reference to the assay method described in WO 01/62903, page 60, lines 3-17.

Cellulase activity: The term "cellulase activity" is defined herein as an enzyme catalyzed hydrolysis of 1,4-beta-D-glucosidic linkages in beta-1,4-glucan (cellulose). For purposes of the present invention, cellulase activity is determined using AZCL-HE-cellulose (from Megazyme) as the reaction substrate.

Variant: The term "variant" is defined herein as a polypeptide having xyloglucanase activity comprising an alteration, such as a substitution, insertion, and/or deletion, of one or more (several) amino acid residues at one or more (several) specific positions which positions correspond to the amino acid positions in SEQ ID NO: 3. The variants of the invention may also have cellulase activity. The altered polypeptide (variant) is obtained through human intervention by modification of the polynucleotide sequence encoding the parental enzyme. The parental enzyme may be encoded by SEQ ID NO: 1, SEQ ID NO: 4 or SEQ ID NO: 6 or a sequence which is at least 75% identical to one of these sequences. The variant polypeptide sequence is preferably one which is not found in nature.

Wild-Type Enzyme: The term "wild-type" xyloglucanase denotes a xyloglucanase expressed by a naturally occurring microorganism, such as bacteria, yeast, or filamentous fungus found in nature. The term wild-type may be used interchangeably with the term "naturally occurring".

Parent Enzyme: The term "parent" xyloglucanase or "parental" xyloglucanase as used herein means a xyloglucanase to which a modification, e.g., substitution(s), insertion(s), deletion(s), and/or truncation(s), is made to produce the enzyme variants of the present invention. This term also refers to the polypeptide with which a variant is compared and aligned. The parent may be a naturally occurring (wild-type) polypeptide such as the enzyme of SEQ ID NO:2 or SEQ ID NO:3 or SEQ ID NO: 5 or SEQ ID NO: 7. The parent polypeptide may, however, also be a variant of a naturally occurring polypeptide which has been modified or altered in the amino acid sequence. A parent may also be an allelic variant, which is a polypeptide encoded by any of two or more alternative forms of a gene occupying the same chromosomal locus.

Isolated variant or polypeptide: The term "isolated variant" or "isolated polypeptide" as used herein refers to a variant or a polypeptide that is isolated from a source, e.g. the host cell from which it is expressed or the enzyme complex it is normally present in. Preferably, the polypeptide is at least 40% pure, more preferably at least 60% pure, even more preferably at least 80% pure, most preferably at least 90% pure, and even most preferably at least 95% pure, as determined by SDS-PAGE.

Substantially pure variant or polypeptide: The term "substantially pure variant" or "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure variant or polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The variants and polypeptides of the present invention are preferably in a substantially pure form. This can be accomplished, for example, by preparing the variant or polypeptide by well-known recombinant methods or by classical purification methods.

Mature polypeptide: The term "mature polypeptide" is defined herein as a polypeptide having xyloglucanase activity that is in its final form following translation and any post-translational modifications, such as N-terminal processing, C-terminal truncation, glycosylation, phosphorylation, etc. For the polypeptide defined by SEQ ID NO: 2, the mature xyloglucanase sequence may in theory start at position 28 of SEQ ID NO: 2. The mature sequence ends at position 551 of SEQ ID NO: 2. The theoretical mature xyloglucanase sequence is show in SEQ ID NO: 3.

Mature polypeptide coding sequence: The term "mature polypeptide coding sequence" is defined herein as a nucleotide sequence that encodes a mature polypeptide having xyloglucanase activity. In one aspect, the mature polypeptide coding sequence is nucleotides 82 to 1653 of SEQ ID NO: 1.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; http://emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Functional fragment: The term "functional fragment of a polypeptide" is used to describe a polypeptide which is derived from a longer polypeptide, e.g., a mature polypeptide, and which has been truncated either in the N-terminal region or the C-terminal region or in both regions to generate a fragment of the parent polypeptide. To be a functional polypeptide the fragment must maintain at least 20%, preferably at least 40%, more preferably at least 50%, more preferably at least 60%, more preferably at least 70%, more preferably at least 80%, even more preferably at least 90%, most preferably at least 95%, and even most preferably at least 100% of the xyloglucanase activity of the full-length/mature polypeptide.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In one aspect, the isolated polynucleotide is at least 40% pure, more preferably at least 60% pure, even more preferably at least 80% pure, and most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered polypeptide production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Host cell: The term "host cell", as used herein, includes any cell type that is susceptible to transformation, transfection, transduction, and the like with a nucleic acid construct or a vector comprising a polynucleotide of the present invention. The term "host cell" encompasses any progeny of a parent cell that is not identical to the parent cell due to mutations that occur during replication.

Improved chemical stability: The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants better able to catalyze a reaction in the presence of such chemicals. In a particular aspect of the invention the improved chemical stability is an improved stability in a detergent, in particular in a liquid detergent. The improved detergent stability is in particular an improved stability of the xyloglucanase activity when a xyloglucanase variant of the present invention is mixed into a liquid detergent formulation and then stored at temperatures between 15 and 50° C.

In the present invention liquid detergents are particular useful as liquid laundry detergents.

Conventions for Designation of Variants

For purposes of the present invention, the amino acid sequence of the xyloglucanase disclosed in SEQ ID NO: 3 is used to determine the corresponding amino acid residue in another xyloglucanase. The amino acid sequence of another xyloglucanase is aligned with the amino acid sequence of the xyloglucanase disclosed in SEQ ID NO: 3, and based on the alignment the amino acid position number corresponding to any amino acid residue in the amino acid sequence of the xyloglucanase disclosed in SEQ ID NO: 3 can be determined.

An alignment of polypeptide sequences may be made, for example, using "ClustalW" (Thompson, J. D., Higgins, D. G. and Gibson, T. J., 1994, CLUSTAL W: Improving the sensitivity of progressive multiple sequence alignment through sequence weighting, positions-specific gap penalties and weight matrix choice, *Nucleic Acids Research* 22: 4673-4680). An alignment of DNA sequences may be done using the polypeptide alignment as a template, replacing the amino acids with the corresponding codon from the DNA sequence.

In describing the various xyloglucanase variants of the present invention, the nomenclature described below is adapted for ease of reference. In all cases, the accepted IUPAC single letter or triple letter amino acid abbreviation is employed.

Substitutions. For an amino acid substitution, the following nomenclature is used: original amino acid,/position/substituted amino acid. Accordingly, the substitution of threonine with alanine at position 226 is designated as "Thr226Ala" or "T226A". Multiple mutations are separated by addition marks ("+"), e.g., "G205R+S411F", representing mutations at positions 205 and 411 substituting glycine (G) with arginine (R), and serine (S) with phenylalanine (F), respectively. Where an original amino acid may be substituted by an amino acid selected from a group it is designated as "K129R,S,A,I,F,Q" representing the substitution of a lysine (K) at position 129 with an amino acid selected from the group consisting of: arginine (R), serine (S), alanine (A), isoleucine (I), phenylalanine (F) and glutamine (Q). Alternatively, "K129R,S,A,I,F,Q" could be written as K129R or K129S, or K129A, or K129I or K129F or K129Q Deletions. For an amino acid deletion, the following nomenclature is used: Original amino acid/position/asterisk (*). Accordingly, the deletion of glycine at position 195 is designated as "Gly195*" or "G195*". Multiple deletions are separated by addition marks ("+"), e.g. G195*+S411*".

Insertions. For an amino acid insertion, the following nomenclature is used: Asterisk (*)/position/lower case letter/inserted amino acid, where the lower case letter indicates the addition of an amino acid down stream of the position number. Accordingly, the insertion of a glutamic acid (E) down stream of position 10 is designated "*10aE". If a second amino acid, e.g. a valine (V), is to be inserted down stream of position 10 after the glutamic acid (E) it is designated "*10aE+*10bV". Additions to the N-terminal of the polypeptide are designated with a 0 (zero). The addition of a glutamic acid (E) and a valine (V) added to the N-terminal amino acid of a polypeptide is designated as *0aE+*0bV.

Parent Xyloglucanases

In the present invention, the parent xyloglucanase is either (a) a xyloglucanase belonging to family 44 of glycosyl hydrolases also termed family 44 xyloglucanases; or (b) a polypeptide selected from the group consisting of SEQ ID NO:3, SEQ ID NO: 5 and SEQ ID NO: 7; or (c) a polypeptide comprising an amino acid sequence having at least 75% identity with the mature polypeptide of SEQ ID NO: 3; or (d) a polypeptide encoded by a polynucleotide that hybridizes under at least medium stringency conditions with (i) the mature polypeptide coding sequence of SEQ ID NO: 1 or SEQ ID NO: 4 or SEQ ID NO: 6, (ii) the genomic DNA sequence comprising the mature polypeptide coding sequence of SEQ ID NO: 1 or SEQ ID NO: 4 or SEQ ID NO: 6 or (iii) a full-length complementary strand of (i) or (ii); or (e) a polypeptide encoded by a polynucleotide comprising a nucleotide sequence having at least 70% identity with the mature polypeptide coding sequence of SEQ ID NO: 1.

In a first aspect, the parent xyloglucanase comprise an amino acid sequence having a degree of identity to the mature polypeptide of SEQ ID NO: 3 of preferably at least at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99%, which have xyloglucanase activity (hereinafter "homologous polypeptides"). In one aspect, the homologous polypeptides have an amino acid sequence that differs by ten amino acids, preferably by nine, more preferably by eight, more preferably by seven, more preferably by six, more preferably by five amino acids, more preferably by four amino acids, even more preferably by three amino acids, most preferably by two amino acids, and even most preferably by one amino acid from the mature polypeptide of SEQ ID NO: 3.

Substantially homologous parent xyloglucanases may have one or more (several) amino acid alterations such as substitutions, deletions and/or insertions. These changes are preferably of a minor nature, that is conservative amino acid substitutions and other substitutions that do not significantly affect the three-dimensional folding or activity of the protein or polypeptide; small deletions, typically of one to about 9 amino acids, preferably from one to about 15 amino acids and most preferably from one to about 30 amino acids; and small amino- or carboxyl-terminal extensions, such as an amino-terminal methionine residue, a small linker peptide of up to about five to ten residues, preferably from 10 to 15 residues and most preferably from 20 to 25 residues, or a small extension that facilitates purification (an affinity tag), such as a poly-histidine tract, or protein A (Nilsson et al., 1985, *EMBO J.* 4: 1075; Nilsson et al., 1991, *Methods Enzymol.* 198: 3. See, also, in general, Ford et al., 1991, *Protein Expression and Purification* 2: 95-107.

Although the changes described above preferably are of a minor nature, such changes may also be of a substantive nature such as fusion of larger polypeptides of up to 300 amino acids or more both as amino- or carboxyl-terminal extensions.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by Neurath and Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in the xyloglucanase polypeptides of the present invention can be identified according to procedures known in the art, such as site-directed mutagenesis or alanine-scanning mutagenesis (Cunningham and Wells, Science 244: 1081-1085, 1989). In the latter technique, single alanine mutations are introduced at every residue in the molecule, and the resultant mutant molecules are tested for biological activity (i.e. xyloglucanase activity) to identify amino acid residues that are critical to the activity of the molecule. See also, Hilton et al., J. Biol. Chem. 271:4699-4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-312, 1992; Smith et al., J. Mol. Biol. 224:899-904, 1992; Wlodaver et al., FEBS Lett. 309:59-64, 1992. The identities of essential amino acids can also be inferred from analysis of homologies with polypeptides which are related to a polypeptide according to the invention. The crystal structure of an enzyme belonging to the family 44 glycosyl hydrolases has been published by Kitago et. al, J. Biol. Chem. Vol. 282: 35703-35711, 2007. Based on this structure it is possible to generate a three dimensional structure of the parent xyloglucanase (SEQ ID NO: 3) in silico. Based on comparison with the published structure the following residues in SEQ ID NO: 3 have been identified as critical for the enzymatic function E187 (Catalytic-Acid/Base), E358 (Catalytic-Nucleophile), E56 (Carboxylate group coordinating Ca2+) and D154 (Carboxylate group coordinating Ca2+). These positions should, therefore, preferably not be mutated in the parent enzyme.

The parent xyloglucanase preferably comprises the amino acid sequence of SEQ ID NO: 3 or an allelic variant thereof; or a fragment thereof having xyloglucanases activity. In one aspect, the parent xyloglucanase comprises the amino acid sequence of SEQ ID NO: 2. In another aspect, the parent xyloglucanase comprises the mature polypeptide of SEQ ID NO: 2. In another aspect, the parent xyloglucanase consists of the amino acid sequence of SEQ ID NO: 3 or an allelic variant thereof; or a fragment thereof having xyloglucanase activity. In another aspect, the parent xyloglucanase comprises the amino acid sequence of SEQ ID NO: 5, or an allelic variant thereof; or a fragment thereof having xyloglucanase activity. In another aspect, the parent xyloglucanase comprises the amino acid sequence of SEQ ID NO: 7, or an allelic variant thereof; or a fragment thereof having xyloglucanase activity.

A fragment of the mature polypeptide of SEQ ID NO: 3 is a polypeptide having one or more (several) amino acids deleted from the amino- and/or carboxyl-terminus of this amino acid sequence and still maintaining xyloglucanase activity.

In a second aspect, the parent xyloglucanases are encoded by polynucleotides that hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1 or SEQ ID NO: 4 or SEQ ID NO: 6, (ii) the genomic DNA sequence comprising the mature polypeptide coding sequence of SEQ ID NO: 1 or SEQ ID NO: 4 or SEQ ID NO: 6, (iii) a subsequence of (i) or (ii), or (iv) a full-length complementary strand of (i), (ii), or (iii) (J. Sambrook, E. F. Fritsch, and T. Maniatis, 1989, *Molecular*

*Cloning, A Laboratory Manual,* 2d edition, Cold Spring Harbor, N.Y.). The subsequence may encode a polypeptide fragment having xyloglucanase activity. In one aspect, the complementary strand is the full-length complementary strand of the mature polypeptide coding sequence of SEQ ID NO: 1 or SEQ ID NO: 4 or SEQ ID NO: 6.

A subsequence of the mature polypeptide coding sequence of SEQ ID NO: 1 or SEQ ID NO: 4 or SEQ ID NO: 6, or a homolog thereof, is a nucleotide sequence where one or more (several) nucleotides have been deleted from the 5'- and/or 3'-end, where the polypeptide encoded by the subsequence possess xyloglucanase activity.

The parent enzymes may also be allelic variants of the polypeptides that have xyloglucanase activity.

The polynucleotide of SEQ ID NO: 1 or SEQ ID NO: 4 or SEQ ID NO: 6; or a subsequence thereof; as well as the amino acid sequence of SEQ ID NO: 3 or SEQ ID NO: 5 or SEQ ID NO: 7; or a fragment thereof; may be used to design nucleic acid probes to identify and clone DNA encoding parent xyloglucanases from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, preferably at least 900 nucleotides in length, preferably at least 1000 nucleotides in length, preferably at least 1100 nucleotides in length, preferably at least 1200 nucleotides in length, preferably at least 1300 nucleotides in length, preferably at least 1400 nucleotides in length, preferably at least 1500 nucleotides in length or most preferably at least 1600 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA library prepared from other organisms may be screened for DNA that hybridizes with the probes described above and encodes a parent xyloglucanase. Genomic or other DNA from other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is used in a Southern blot. For purposes of the present invention, hybridization indicates that the polynucleotide hybridizes to a labeled nucleotide probe corresponding to the polynucleotide shown in SEQ ID NO: 1, its complementary strand, or a subsequence thereof, under low to very high stringency conditions. Molecules to which the probe hybridizes can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 82 to 1653 of SEQ ID NO: 1. In another aspect, the nucleic acid probe is a polynucleotide sequence that encodes the polypeptide of SEQ ID NO: 2, or a subsequence thereof. In another aspect, the nucleic acid probe is SEQ ID NO: 1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the parent xyloglucanase is encoded by a polynucleotide comprising or consisting of a nucleotide sequence having a degree of identity to the mature polypeptide coding sequence of SEQ ID NO: 1 of preferably at least 65%, more preferably at least 70%, more preferably at least 75%, more preferably at least 80%, more preferably at least 85%, even more preferably at least 90%, most preferably at least 95%, and even most preferably 96%, 97%, 98%, or 99%, which encode an active polypeptide. In one aspect, the mature polypeptide coding sequence is nucleotides 82 to 1653 of SEQ ID NO: 1.

The parent xyloglucanase may be obtained from microorganisms of any genus. In one aspect, the parent xyloglucanase is secreted extracellularly.

In a further aspect the parent xyloglucanase may be a bacterial xyloglucanase. For example, the xyloglucanase may be a Gram positive bacterial polypeptide such as a *Bacillus*, preferably from the *Bacillus/Lactobacillus* subdivision, preferably a species from the genus *Paenibacillus*, especially *Paenibacillus polymyxa*, e.g. *Paenibacillus polymyxa*, ATCC 832, preferably the xyloglucanase is a family 44 xyloglucanse, e.g. as described in WO 01/62903, more preferably the xyloglucanase of SEQ ID NO: 5, more preferably the xyloglucanase of SEQ ID NO: 7, and most preferably the xyloglucanase of SEQ ID NO: 2 or the mature polypeptide thereof.

Generation of Variants

Variants of a parent xyloglucanase can be prepared according to any mutagenesis procedure known in the art, such as random and/or site-directed mutagenesis, synthetic gene construction, semi-synthetic gene construction, random mutagenesis, shuffling, etc.

Synthetic gene construction entails in vitro synthesis of a designed polynucleotide molecule to encode a polypeptide molecule of interest. Gene synthesis can be performed utilizing a number of techniques, such as the multiplex microchip-based technology described by Tian, et. al., (Tian, et. al., Nature 432:1050-1054) and similar technologies wherein oligonucleotides are synthesized and assembled upon photo-programmable microfluidic chips.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide fragments may then be shuffled.

Site-directed mutagenesis is a technique in which one or several mutations are created at a defined site in a polynucleotide molecule encoding the parent xyloglucanase. The technique can be performed in vitro or in vivo.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent xyloglucanase and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. For further description of suitable techniques reference is made to Sambrook et al. (1989), Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990), and WO 96/34946; Scherer and Davis, 1979, *Proc. Natl. Acad. Sci. USA* 76: 4949-4955; and Barton et al., 1990, *Nucleic Acids Research* 18: 7349-4966.

After the ligase reaction the ligation mixture may be used to transform a host cell, for cloning purposes *E. coli* cells are often used as described in Ausubel, F. M. et al. The transformed *E. coli* cells can be propagated in liquid media or on solid agar plates, plasmids can be rescued from the transformed cells and used to transform *B. subtilis* cells. Suitable competent *Bacillus* cells, such as MB1510, an 168-derivative (e.g. available from BGSC with accession no. 1A1 168 trpC2), may be transformed as described in WO 03/095658. An *E. coli* plasmid-borne integration cassette for library construction may be used for *Bacillus* transformation. The method is described in detail in WO 03/095658. Alternatively, an in vitro amplified PCR-SOE-product (Melnikov and Youngman, Nucleic Acid Research 27, 1056) may be used.

Site-directed mutagenesis can be accomplished in vivo by methods known in the art. See, for example, U.S. Patent Application Publication 2004/0171154; Storici et al., 2001, *Nature Biotechnology* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants of a parent xyloglucanases.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223, 409; WO 92/06204) and region-directed mutagenesis (Derbyshire et al., 1986, *Gene* 46:145; Ner et al., 1988, *DNA* 7:127).

Mutagenesis/shuffling methods as described above can be combined with high-throughput, automated screening methods to detect the activity of cloned, mutagenized polypeptides expressed by host cells, e.g. *Bacillus* as described above. Mutagenized DNA molecules that encode polypeptides weith xyloglucanase activity can be recovered from the host cells and rapidly sequenced using standard methods in the art.

Variants

In the present invention, the isolated variants of a parent xyloglucanase comprise an alteration at one or more (several) positions selected from the group consisting of positions number 68, 123, 156, 118, 200, 129, 137, 193, 92, 83, 149, 34, 340, 332, 9, 76, 331, 310, 324, 498, 395, 366, 1, 374, 7, 140, 8, 14, 21, 211, 37, 45, 13, 78, 87, 436, 101, 104, 111, 306, 117, 119, 414, 139, 268, 142, 159, 164, 102, 168, 176, 180, 482, 183, 202, 206, 217, 4, 222, 19, 224, 228, 232, 2, 240, 244, 5, 247, 249, 328, 252, 259, 406, 267, 269, 275, 179, 166, 278, 281, 288, 298, 301, 18, 302, 165, 80, 303, 316, 169, 322, 120, 146, 342, 348, 147, 353, 380, 468, 382, 383, 38, 384, 389, 391, 10, 392, 396, 177, 397, 399, 409, 237, 413, 253, 415, 418, 40, 443, 445, 148, 449, 225, 450, 454, 3, 455, 456, 299, 461, 470, 204, 476, 488, 347, and 507, wherein the variant having xyloglucanase activity comprises an amino acid sequence having a degree of identity of at least 70%, more preferably at least 75%, more preferably at least 80%, more preferably at least 85%, even more preferably at least 90%, more preferably at least 95%, more preferably at least about 97%, most preferably at least 98% and even more preferably 99% to the amino acid sequence of the parent xyloglucanase. The numbering of the positions are relative to the amino acid sequence of SEQ ID NO: 3. Preferably, the variants comprising alterations at one or more of the above identified positions have an increased stability in detergent, preferably in liquid detergent as compared to the parent xyloglucanase.

In a preferred embodiment the variant comprises one or more (several) of the following combinations of alterations:

V1*+V2*+H3*;
V1Q+*1aE+*1bV;
H3A;
H3A+H436A;
K8A,Q,S;
T9D;
T9D+L34F+A83E+Q149E+H193T+S332P+R340T;
I10V+D33E+M40L+A41T+Q67M+Y73F+S76D+G78A+Q82K+T92A+L102Q+Q137E+I222V+V228I+D249N+S269N+V272A+E333A+I337L+M356L+T374A+S416A+D444Y+A469E+K470T+I473G+T517A+S522*;
I10V+F17S+D33E+M40L+A41T+Q67M+N72S+S76D+G78A+Q82K+Q137E+V219A+D249N+V272A+I337L+M356L+V397A+S416A+T421I+S424N+N441D+D444Y+V450I+K470T+I473S+V477I;

I10V+F17S+D33E+M40L+Q67M+N72S+S76D+G78A+
Q82K+T92A+L102Q+Q137E+H164N+N168K+T172A+
V219A+I222V+V228I+D249N+S269N+V272A+E333A+
I337L+M356L+N415S+T421I+S424H+N441D+D444Y+
S522P+P523V+V524E;
I10V+F17S+D33E+M40L+Q67M+N72S+S76D+G78A+
Q82K+T92A+L102Q+Q137E+I222V+V228I+D249N+
V272A+I337L+M356L+T374A+V397A+S416A+T421I+
S424N+N441D+D444Y+V450I+A469E+K470T+I473G+
T517A+S 522P+P523V+V524E;
I10V+F17S+D33E+Q67M+N72S+S76D+G78A+Q82K+
T92A+L102Q+Q137E+N168K+T172A+I222V+V228I+
D249N+V272A+E333A+I337L+M356L+V397A+S416A+
T421I+S424H+

T104A+P111Q+A117S+K129A+R156Y;
P111Q;
K118A+K129A;
K118A+K129A+F146L+R156Y+G200P+N331F;
K118A+K129A+Q137E+R156Y+G200P+N331F;
K118A+K129A+R156Y;
K118A+K129A+R156Y+A224P;
K118A+K129A+R156Y+G200P;
K118A+K129A+R156Y+G200P+M310V+N331F;
K118A+K129A+R156Y+G200P+N331F;
K118A+K129A+R156Y+G200P+N331F+N399I;
K118A+K129A+R156Y+K169A+G200P+N331F;
K118A+K129A+R156Y+K470T;
K118A,R;
K118A+R156Y;
K118A+R156Y+G200P;
D119L;
G120A;
S123P,T;
S123T+K129A+R156Y;
K129A,F,I,K,R,S,T;
K129A+K169A;
K129A+K176P;
K129A+K275Q;
K129A+K445S;
K129A+K470T;
K129A+Q137E+R156Y;
K129A+Q137E+R156Y+G200P;
K129A+Q137E+R156Y+K470T;
K129A+Q137E+V139K+N140F+Q147S+R156Y;
K129A+R156Y;
K129A+R156Y+A177T+V179I+A183S;
K129A+R156Y+A328G;
K129A+R156Y+D247G;
K129A+R156Y+D249G,N,S;
K129A+R156Y+D303I,K,S,V;
K129A+R156Y+D324N;
K129A+R156Y+D366H+T374A;
K129A+R156Y+D461N,Q,T;
K129A+R156Y+E288Q;
K129A+R156Y+G200P;
K129A+R156Y+G200P+G204T+R211K;
K129A+R156Y+H164N;
K129A+R156Y+H436Y;
K129A+R156Y+I10V+V14I+D19E;
K129A+R156Y+I222V+A224P+V228I+V232A;
K129A+R156Y+K176P,S;
K129A+R156Y+K275T;
K129A+R156Y+K322I+K454Q;
K129A+R156Y+K406N+N415G;
K129A+R156Y+K454Q;
K129A+R156Y+L380F+N383Y+D384G+N389T;
K129A+R156Y+N298F+E299N+G301T;
K129A+R156Y+N302K+D303L,S;
K129A+R156Y+N331F;
K129A+R156Y+P507A;
K129A+R156Y+R267H;
K129A+R156Y+R409L,T;
K129A+R156Y+S443D+K445S+L449I+V450I+S455N+M456Y;
K129A+R156Y+T244D;
K129A+R156Y+V159M+H164N+F165Y;
K129A+R156Y+V259I+R267K+L268K+S269A;
Q137D,E;
N140F;
K142A,Q,R;
F146C+H164C;
F146K,L;
F146L+K322I;
L148K+N168D;
Q149E;
R156A,D,E,F,I,K,L,M,N,P,Q,R,S,T,V,W,Y;
R156Y+N331F;
V159M;
H164A,N;
L166I;
N168D;
K169A,Q,R;
K176P;
A177E,T;
K180R;
H193A,D,S,T;
R197A,L;
H199A;
G200A,C,D,E,F,H,I,K,L,M,N,P,Q,R,S,T,V,W,Y;
G200P+A224P;
K202N,Q,R;
S214E;
K217A;
A221K;
G225S;
V232A;
G237A,S,V;
K240A,Q,R;
K252A,Q,R;
G253A;
R267A;
L268I;
K275A,Q,R;
L278I;
F281L;
M290R;
R295A;
K306A,R;
K307Q;
M310I,L,V;
M310V+N399I;
R314A;
G316I;
K322A,R;
D324N;
N331A,C,D,E,F,G,H,I,K,L,M,P,Q,R,S,T,V,W,Y;
S332M,P;
S332P+V397I;
R340A,N,T;
K342A;
V345I;
K347A,Q,R;
D348G;
K353Q,R;
D366H;
M373Q;
T374A;
L380F;
K382A;
N383Y;
N389A,F,N,V;
W391V;
K392G,Q;
D395G;
G396P;
V397S;
N399I;
K406N;

G413A,S;
K414A;
N415S;
T417K;
F418I;
V431E;
H436A;
N441G+A442E+S443D;
S443E,K,Q;
K445A,R,S;
K445C+K470C;
H448A;
K454R;
S467R+G468S+A469T;
G468S,Y;
K470P,R,T;
I473T;
K476Q;
K482A,Q,R;
K488A,Q,R,T;
A490R;
G498A,D,S;
R500A,T,V;
H512A;
T517A+G518D; or
G518D;

In one aspect, the number of amino acid alterations in the variants of the present invention comprise preferably the total number of 55, preferably 52, more preferably 50, more preferably 40, more preferably 30, more preferably 20, more preferably 15, more preferably ten, more preferably nine, more preferably eight, even more preferably seven, even more preferably six, even more preferably five, even more preferably four, even more preferably three, and most preferably two alterations, and most preferably one alteration. In another aspect the total number of alterations is one, preferably two, more preferably three, even more preferably four, even more preferably five, even more preferably six, even more preferably seven, even more preferably eight, even more preferably nine, most preferably ten. The alteration may be in the form of i) an insertion of an amino acid downstream of the amino acid which occupies the position; ii) deletion of the amino acid which occupies the position, or iii) a substitution of the amino acid which occupies the position with a different amino acid. The alterations may be made independently of each other, for example in one position there may be an insertion while there is a substitution at a second position and a deletion at a third position as compared to the parental xyloglucanase. In a preferred embodiment the variant only comprises substitutions.

In one aspect of the invention positions to be mutated are identified based on consensus sequence analysis. The analysis is performed by aligning SEQ ID NO: 3, with SEQ ID NO: 5 and SEQ ID NO: 7 as well as with other sequences from the uniprot database which are 30% identical to the family 44 glycosyl hydrolase region of SEQ ID NO: 3. The resulting consensus sequences are shown in FIG. 1. Consensus sequence 1 is the sequence comprising the most abundant amino acid at a given position from the alignment, consensus sequence 2 is the sequence with the 2$^{nd}$ most abundant amino acid at a given position and so forth. In one aspect of the invention, one or more (several) residues of SEQ ID NO: 3 are replaced by the corresponding residue from Consensus sequence 1 or Consensus sequence 2 or Consensus sequence 3 or Consensus sequence 4. In one aspect of the present invention the variants comprise an alteration at one or more (several) of the positions selected from the group of 52 positions identified by the consensus sequence analysis consisting of position number 10, 19, 68, 80, 89, 104, 111, 117, 123, 129, 137, 139, 140, 147, 156, 159, 164, 165, 177, 179, 183, 200, 204, 211, 222, 224, 225, 228, 232, 259, 267, 268, 269, 281, 328, 345, 366, 374, 380, 383, 384, 406, 415, 436, 443, 445, 449, 450, 455, 456, 488 and 507. In a preferred embodiment the alteration is a substitution, or several substitutions, selected from the group consisting of: I10V, D19E, Q68H, L80V, G89A, T104A, P111Q, A117S, S123P, K129T, Q137E, V139K, N140F, Q147S, R156Y, V159M, H164N, F165Y, A177T, V179I, A183S, G200P, G204T, R211K, I222V, A224P, G225S, V228I, V232A, V259I, R267K, L268K, S269A, F281L, A328G, V345I, D366H, T374A, L380F, N383Y, D384G, K406N, N415G, H436Y, S443D, K445S, L449I, V450I, S455N, M456Y, K488T and P507A.

In another aspect of the invention the variant is generated by changing those amino acids in the parental peptide which have a positive charges and are situated within 20 Å of the calcium ion to neutral or negative charged amino acids. Preferred variants of the present invention comprise variants in which the overall charge within 20 Å from the calcium ion has been made more negative. In such variants positively charged amino acids may have been replaced with amino acids that are neutral or negatively charged under the application conditions. In accordance herewith, preferred variants may have an amino acid residue which is partly or fully positively charged under the "chemical stability" or application conditions, i.e. a Lys, Arg or His replaced by a negative or neutral amino acid. Preferred replacement amino acids may be negatively charged amino acids as Asp and Glu or neutral amino acids as Ala, Asn, Gln, Tyr, Trp and Phe. A preferred variant of the present invention comprises an alteration at one or more of the positions selected form the group consisting of position number 49, 87, 118, 129, 134, 142, 156, 169 and 197. In a preferred embodiment the alterations are substitutions at one or more of the positions selected form the group consisting of position number 87, 118, 129, 134, 142, 156, and 169. In a preferred embodiment the substitution is selected from the group consisting of: K87A; K129A,S,F,I; K118A; K142A,Q, R156Y,F,V,I,K,W,L,M and K169Q,A.

In one aspect, a variant of a parent xyloglucanase comprises an alteration at one or more (several) positions corresponding to positions 68 or 123 or 156 or 118 or 200 or 129 or 137 or 193 or 92 or 76 or 331. Preferably, the variant comprises substitution at position 68 and one or more substitutions at one or more additional positions, selected from the group consisting of position number 123, 156, 118, 200, 129, 137, 193, 92, 83, 149, 34, 340, 332, 9, 76, 331, 310, 324, 498, 395 and 366.

In another aspect, a variant comprises a substitution at position 156 and one or more substitutions at one or more additional positions selected from the group consisting of position number 10, 13, 14, 19, 37, 68, 78, 92, 118, 123, 129, 137, 139, 140, 147, 159, 164, 165, 169, 176, 177, 179, 183, 200, 204, 211, 222, 224, 244, 247, 249, 259, 267, 268, 269, 275, 288, 299, 301, 302, 303, 310, 324, 328, 331, 366, 380, 383, 384, 389, 406, 409, 415, 436, 443, 445, 449, 450, 454, 455, 456, 461, 470 and 507.

In another aspect, a variant of a parent xyloglucanase comprises alterations at two or more (several) positions corresponding to positions 68 or 123 or 156 or 118 or 200 or 129 or 137 or 193 or 92 or 76 or 331. Preferably, the variant comprises a substitution at position 68 or 123 or 156 or 118 or 200 or 129. Even more preferably the variant comprises a substitution at position 129 and position 156.

In another aspect, a variant of a parent xyloglucanase comprises alterations at three or more (several) positions corresponding to positions 68 or 123 or 156 or 118 or 200 or 129 or 137 or 193 or 92 or 76 or 331.

In another aspect, a variant of a parent xyloglucanase comprises alterations at four or more (several) positions corresponding to positions 68 or 123 or 156 or 118 or 200 or 129 or 137 or 193 or 92 or 76 or 331.

In another aspect, a variant of a parent xyloglucanase comprises alterations at five or more (several) positions corresponding to positions 68 or 123 or 156 or 118 or 200 or 129 or 137 or 193 or 92 or 76 or 331.

In another aspect, a variant of a parent xyloglucanase comprises alterations at six or more (several) positions corresponding to positions 68 or 123 or 156 or 118 or 200 or 129 or 137 or 193 or 92 or 76 or 331.

In another aspect, a variant of a parent xyloglucanase comprises alterations at seven or more (several) positions corresponding to positions 68 or 123 or 156 or 118 or 200 or 129 or 137 or 193 or 92 or 76 or 331.

In another aspect, a variant of a parent xyloglucanase comprises alterations at the positions corresponding to positions 129 and 156 and 331 and 200 and 118.

In another aspect, a variant of a parent xyloglucanase comprises alterations at the positions corresponding to positions 68 and 129 and 156 and 331 and 200 and 118.

In another aspect, a variant of a parent xyloglucanase comprises alterations at the positions corresponding to positions 68 and 92 and 129 and 156 and 331 and 200 and 118.

In another aspect the variant comprises one or more (several) substitutions selected from the group consisting of: Q68H,N,L; S123P,T; R156Y,F,V,I,K,W,L,M; K118A,R; G200P,E,S,D; K129T,A,S; Q137E; H193T,S,D; T92V,I,A,S; A83E; Q149E; L34F,I,V; R340T,N; S332P; T9D; S76W,V,I, K,R,T; N331F,C; M310I,V,L; D324N; G498A,D; D395G and D366H. Preferably, the substitutions are selected from the group consisting of Q68H; S123P; R156Y,F; K118A; G200P,E; K129T,A; Q137E; H193T; T92V and N331F. More preferably, the substitutions are selected from the group consisting of Q68H; S123P; R156Y,F; K118A; G200P,E; K129T, A; Q137E; T92V and N331F. More preferably, the variant contains a substitution in nine or eight, seven or six or five or four or three or two or one position(s), where the substitutions are selected from the group consisting of Q68H; S123P; R156Y,F; K118A; G200P,E; K129T,A; Q137E; T92V and N331F.

In a further aspect the variant comprises one or more (several) of the following combinations of substitutions:
Q68H
S123P
R156Y
Q68H+R156Y
K129A+R156Y
S123T+K129A+R156Y
K129A+R156Y+G200P
Q68H+K118R+R156F
Q68H+R156Y+H193T
Q68H+R156F+G200P+N331F
Q68H+T92V+K118A+R156Y
K118A+K129A+R156Y+G200P+N331F
G78A+T92V+K118A+K129A+R156Y
Q68H+K129T+R156K+G200P+N331F
K118A+K129A+R156Y+K169A+G200P+N331F
T92V+K118A+K129A+R156Y+G200P+N331F
G78A+K118A+K129A+R156Y+G200P+N331F
G78A+T92V+K118A+K129A+R156Y+K169A
Q68H+T92V+Q137E+R156Y+G200P+N331F
Q68H+T92V+K118A+Q137E+R156Y+N331F
Q68H+T92V+R156Y+G200P+M310V+N331F
Q68H+K118A+K129A+R156Y+G200P+N331F
Q68H+T92V+K118A+K129A+R156Y+G200P+N331F
Q68H+T92V+K118A+Q137E+R156Y+G200P+N331F
Q68H+T92V+K118A+K129A+R156Y+H193T+D366H
Q68H+T92V+K118A+K129A+Q137E+R156Y+H193T+D366H
Q68H+T92V+K118A+K129A+Q137E+R156Y+G200P+N331F
Q68H+T92V+K118A+S123P,T+K129A+Q137E+R156Y+G200P+N331F
Q68H+T92V+K118A+K129A+Q137E+R156Y+G200P+A224P+N331F In a preferred embodiment all the variants described in the above are variants of a parent xyloglucanase which belong to family 44 of glycosyl hydrolases, more preferred the parent xyloglucanase is selected from a xyloglucanase having at least 75% identity to the amino acid sequence of SEQ ID NO: 3, more preferred the parent xyloglucanase is selected from the group consisting of SEQ ID NO: 2, SEQ ID NO: 3, SEQ ID NO: 5 and SEQ ID NO: 7 and most preferred the parent xyloglucanases consists of SEQ ID NO: 3.

Compositions

The present invention also relates to compositions comprising a variant xyloglucanase or a polypeptide having xyloglucanase activity of the present invention. Preferably, the compositions are enriched in such a variant or polypeptide. The term "enriched" indicates that the xyloglucanase activity of the composition has been increased, e.g., with an enrichment factor of 1.1 or more. Preferably the compositions are formulated to provide desirable characteristics such as low color, low odor and acceptable storage stability.

The composition may comprise a variant or polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The polypeptide compositions may be prepared in accordance with methods known in the art and may be in the form of a liquid or a dry formulation. For instance, the polypeptide may be formulated in the form of a granulate or a microgranulate. The variant or polypeptide to be included in the composition may be stabilized in accordance with methods known in the art. In a preferred embodiment the variant xyloglucanase is formulated in a liquid composition.

Uses

The present invention is also directed to methods for using the xyloglucanase variants.

The variant xyloglucanases are preferably incorporated into and/or used together with detergent compositions, for example in laundry detergent compositions, for example household laundry detergent compositions, especially liquid laundry detergent compositions. The detergent composition typically comprises conventional detergent ingredients such as surfactants (anionic, cationic, nonionic, zwitterionic, amphoteric), builders, bleaches, polymers, other enzymes and other ingredients, e.g. as described in WO2007/130562 and WO2007/149806, which are hereby incorporated by reference in its entirety.

The detergent composition can be in any form, such as a solid, liquid, gel or any combination thereof, preferably the composition is in a liquid form, preferably a liquid laundry detergent composition.

An aspect of the invention is the use of a xyloglucanase variant or of a xyloglucanase variant composition of the invention together with a detergent composition in order to impart de-pilling and/or fabric-softness and/or colour clarification and/or soil removal and/or soil anti-redeposition and/or dye transfer inhibition benefits to a fabric or garment.

Furthermore, the invention relates to a process for laundering of fabrics comprising treating fabrics with a washing solution containing a detergent composition and a xyloglucanase variant or a xyloglucanase variant composition of the invention. The laundering treatment can for example be carried out in a machine washing process or in a manual washing process. The washing solution can for example be an aqueous washing solution containing the detergent composition and with a pH between 3 and 12.

During washing and use, the surface of fabrics or garment will conventionally become contaminated with broken or loosed fibre fragments which can give the fabric a faded and worn appearance. Removal of these surface fibres from the fabric will partly restore the original colours and looks of the fabric, resulting in colour clarification and enhanced appearance. A xyloglucanase variant or xyloglucanase variant composition of the invention may be used to provide colour clarification and/or enhanced appearance by use in single or in multiple (repeated) washing cycles.

Furthermore, microfibrils protruding from the surface of the textile can gather into little balls, so-called pills or fluffs that stick to the surface and disturb the appearance of the fabric. A xyloglucanase variant or xyloglucanase variant composition of the invention may be used to remove such pills, an effect that is termed de-pilling.

Colour-clarification and de-pilling can be assessed by visual inspection using a test group panel. The effects may also be measured by light reflection or by determination of cotton fluffs by means of optical measurements. These methods are generally known in the art and briefly described in *Enzymes in Detergency*, 1997, published by Marcel Dekker, page 139 to page 140.

Especially with an increasing number of wash cycles, deposits, which can include particulate soils, soluble soils, dyes and pigments and insoluble salts, build up on the textile fibre surfaces. This can leads to a visible deterioration of the perceived cleaning performance of the washing treatments for example leading to a greyish or yellowish appearance of the fabric. This may be prevented using a xyloglucanase variant or xyloglucanase variant composition of the invention in the wash cycles. This effect is termed anti-redeposition or dye transfer inhibition or soil removal and may be assessed by optical measurements.

Soil or insoluble salt particles trapped on the surface of the fabric and between the fibers can lead to stiffening of the fabric. By including a xyloglucanase variant or xyloglucanase variant composition of the invention in the wash cycles the fabric may be softened.

The fabrics subjected to the methods of the present invention may be conventional washable laundry, for example household laundry. Preferably, the major part of the laundry is garments and fabrics, including knits, wovens, denims, yarns, and towelling, made from cotton, cotton blends or natural or manmade cellulosics (e.g. originating from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell).

It is recognized that the treatment of fabrics and/or garments with a detergent solution containing the xyloglucanase variant or xyloglucanase variant composition of the invention can be particularly relevant in connection with, for example, production of new fibers and/or fabrics and/or garments, and also during laundering of used fabrics and/or garments for example during household laundering processes or in institutional laundering processes.

The dosage of the xyloglucanase variant or the xyloglucanase variant composition of the present invention and other conditions, under which the composition is used, including the composition and concentration of the detergent solution, may be determined on the basis of methods known in the art.

The xyloglucanases can be used in the compositions of the present invention to effect removal of soils containing derivatives of cellulose or hemicellulose, enhance anti-redeposition and improve soil release. The xyloglucanses can also be used in the compositions of the present invention to impart soil release benefits to cotton during a subsequent laundering process. The soil release benefit is observed on cotton fabric and on all types of fabric that comprise a significant amount of cotton, such as cotton-synthetic (e.g. polyester, polyamide such as Nylon™, and elastane) blends.

Laundry Detergent Composition

The laundry detergent composition of the present invention comprises an isolated variant of a parent xyloglucanase. The isolated variant of a parent xyloglucanase is described in more detail above. The composition preferably comprises a specific amphiphilic alkoxylated grease cleaning polymer. The composition preferably comprises detersive surfactant, preferably low levels of detersive surfactant. The specific amphilic alkoxylated grease cleaning polymer is described in more detail below. The detersive surfactant is described in more detail below. The composition preferably comprises a random graft co-polymer. Suitable random graft co-polymers are described in more detail below.

Preferably, the composition comprises a compound having the following general structure: bis($(C_2H_5O)(C_2H_4O)n$)($CH_3$)—$N^+$—$C_xH_{2x}$—$N^+$—($CH_3$)-bis($(C_2H_5O)n$), wherein n=from 20 to 30, and x=from 3 to 8, or sulphated or sulphonated variants thereof.

Preferably, the composition comprises perfume microcapsules, preferably, the perfume is encapsulated in a film of melamine-formaldehyde.

The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch.

The laundry detergent composition can be in any form, such as a solid, liquid, gel or any combination thereof. The composition may be in the form of a tablet or pouch, including multi-compartment pouches. The composition can be in the form of a free-flowing powder, such as an agglomerate, spray-dried powder, encapsulate, extrudate, needle, noodle, flake, or any combination thereof. However, the composition is preferably in the form of a liquid. Additionally, the composition is in either isotropic or anisotropic form. Preferably, the composition, or at least part thereof, is in a lamellar phase.

The composition preferably comprises low levels of water, such as from 0.01 wt % to 10 wt %, preferably to 5 wt %, preferably to 4 wt %, or to 3 wt %, or to 2 wt %, or even to 1 wt %. This is especially preferred if the composition is in the form of a pouch, typically being at least partially, preferably completely enclosed by a water-soluble film. The water-soluble film preferably comprises polyvinyl alcohol.

The composition may comprise a structurant, such as a hydrogenated castor oil. One suitable type of structuring agent which is especially useful in the compositions of the present invention comprises non-polymeric (except for conventional alkoxylation) crystalline hydroxy-functional materials. These structurant materials typically form an associated inter-molecular thread-like network throughout the liquid matrix, typically being crystallized within the matrix in situ. Preferred structurants are crystalline, hydroxyl-containing fatty acids, fatty esters or fatty waxes. Suitable structurants will typically be selected from those having the following formula:

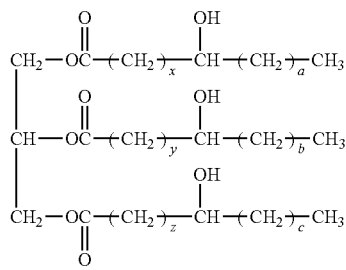

wherein:
(x+a) is from between 11 and 17;
(y+b) is from between 11 and 17; and
(z+c) is from between 11 and 17.
Preferably, in this formula $x=y=z=10$ and/or $a=b=c=5$.

Specific examples of preferred crystalline, hydroxyl-containing structurants include castor oil and its derivatives. Especially preferred are hydrogenated castor oil derivatives such as hydrogenated castor oil and hydrogenated castor wax. Commercially available, castor oil-based, crystalline, hydroxyl-containing structurants include THIXCIN from Rheox, Inc. (now Elementis).

The composition also preferably comprises alkanolamine to neutralize acidic components. Examples of suitable alkanolamines are triethanolamine and monoethanolamine. This is especially preferred when the composition comprises protease stabilizers such as boric acid or derivatives thereof such as boronic acid. Examples of suitable boronic acid derivatives are phenyl boronic acid derivatives of the following formula:

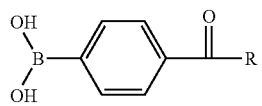

wherein R is selected from the group consisting of hydrogen, hydroxy, $C_1$-$C_6$ alkyl, substituted $C_1$-$C_6$ alkyl, $C_1$-$C_6$ alkenyl and substituted $C_1$-$C_6$ alkenyl.

A highly preferred protease stabilizer is 4-formyl-phenyl-boronic acid. Further suitable boronic acid derivatives suitable as protease stabilizers are described in U.S. Pat. No. 4,963,655, U.S. Pat. No. 5,159,060, WO 95/12655, WO 95/29223, WO 92/19707, WO 94/04653, WO 94/04654, U.S. Pat. No. 5,442,100, U.S. Pat. No. 5,488,157 and U.S. Pat. No. 5,472,628.

The composition may comprise a reversible peptide protease inhibitor. Preferably, the reversible peptide protease inhibitor is a tripeptide enzyme inhibitor. Illustrative non-limiting examples of suitable tripeptide enzyme inhibitor include:

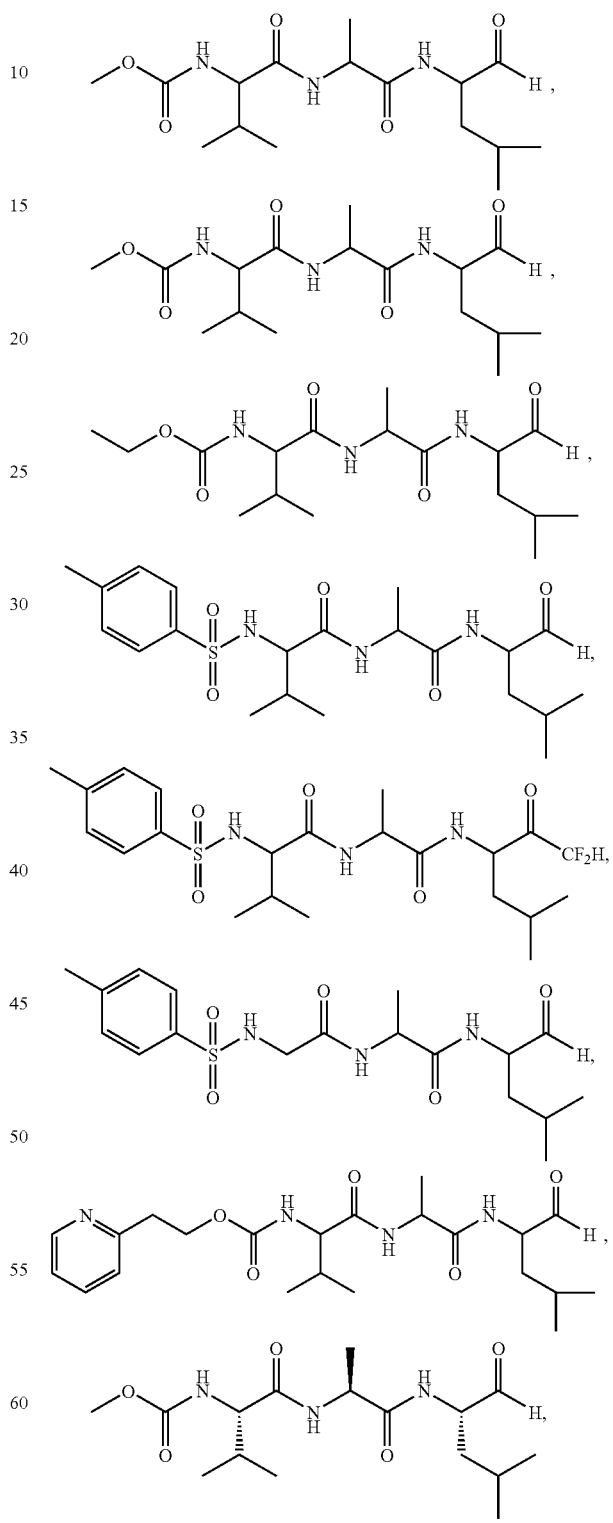

and mixtures thereof.

The reversible peptide protease inhibitor may be made in any suitable manner. Illustrative non-limiting examples of suitable processes for the manufacture of the reversible peptide protease inhibitor may be found in U.S. Pat. No. 6,165,966.

In one embodiment, the composition comprises from about 0.00001% to about 5%, specifically from about 0.00001% to about 3%, more specifically from about 0.00001% to about 1%, by weight of the composition, of the reversible peptide protease inhibitor.

The composition preferably comprises a solvent. The solvent is typically water or an organic solvent or a mixture thereof. Preferably, the solvent is a mixture of water and an organic solvent. If the composition is in the form of a unit dose pouch, then preferably the composition comprises an organic solvent and less than 10 wt %, or 5 wt %, or 4 wt % or 3 wt % free water, and may even be anhydrous, typically comprising no deliberately added free water. Free water is typically measured using Karl Fischer titration. 2 g of the laundry detergent composition is extracted into 50 ml dry methanol at room temperature for 20 minutes and analyse 1 ml of the methanol by Karl Fischer titration.

The composition may comprise from above 0 wt % to 25 wt %, or from above 0 wt % to 20 wt %, or from above 0 wt % to 15 wt %, or from above 0 wt % to 10 wt %, or from above 0 wt % to 8 wt %, preferably from above 0 wt % to 5 wt %, most preferably from above 0 wt % to 3 wt % organic solvent. Suitable solvents include $C_4$-$C_{14}$ ethers and diethers, glycols, alkoxylated glycols, $C_6$-$C_{16}$ glycol ethers, alkoxylated aromatic alcohols, aromatic alcohols, aliphatic branched alcohols, alkoxylated aliphatic branched alcohols, alkoxylated linear $C_1$-$C_5$ alcohols, linear $C_1$-$C_5$ alcohols, amines, $C_8$-$C_{14}$ alkyl and cycloalkyl hydrocarbons and halohydrocarbons, and mixtures thereof.

Preferred solvents are selected from methoxy octadecanol, 2-(2-ethoxyethoxy)ethanol, benzyl alcohol, 2-ethylbutanol and/or 2-methylbutanol, 1-methylpropoxyethanol and/or 2-methylbutoxyethanol, linear $C_1$-$C_5$ alcohols such as methanol, ethanol, propanol, butyl diglycol ether (BDGE), butyltriglycol ether, tert-amyl alcohol, glycerol, isopropanol and mixtures thereof. Particularly preferred solvents which can be used herein are butoxy propoxy propanol, butyl diglycol ether, benzyl alcohol, butoxypropanol, propylene glycol, glycerol, ethanol, methanol, isopropanol and mixtures thereof. Other suitable solvents include propylene glycol and diethylene glycol and mixtures thereof.

The composition preferably comprises from about 0.1% to about 5% by weight of the composition, of a calcium sequestrant having a conditional stability constant at pH 8 of greater than about 4. In one embodiment, the composition, preferably in liquid form, may contain a calcium sequestrant having a conditional stability constant at pH 8 of greater than about 4. The calcium sequestrant with a conditional stability constant at pH 8 of greater than about 4 is able to form soluble complexes with Ca ions. In one embodiment, the calcium sequestrant is selected from selected from 1-Hydroxy Ethylidene 1,1 Di Phosphonic acid (HEDP), Di Ethylene Triamine Penta Acetic acid (DTPA), nitrilotriacetic acid (NTA) and combinations thereof. Additional information on calcium sequestrants and their stability constants can be found in "Keys to Chelation with Versene Chelating Agents" published by the Dow Company see tables 4.4, 4.5, 4.6, 4.7.", and Monsanto Technical Bulletin 53-39(E) ME-2.

Solid Laundry Detergent Composition

In one embodiment of the present invention, the composition is a solid laundry detergent composition, preferably a solid laundry powder detergent composition.

The composition preferably comprises from 0 wt % to 10 wt %, or even to 5 wt % zeolite builder. The composition also preferably comprises from 0 wt % to 10 wt %, or even to 5 wt % phosphate builder.

The composition typically comprises anionic detersive surfactant, preferably linear alkyl benzene sulphonate, preferably in combination with a co-surfactant. Preferred co-surfactants are alkyl ethoxylated sulphates having an average degree of ethoxylation of from 1 to 10, preferably from 1 to 3, and/or ethoxylated alcohols having an average degree of ethoxylation of from 1 to 10, preferably from 3 to 7.

The composition preferably comprises chelant, preferably the composition comprises from 0.3 wt % to 2.0 wt % chelant. A suitable chelant is ethylenediamine-N,N'-disuccinic acid (EDDS).

The composition may comprise cellulose polymers, such as sodium or potassium salts of carboxymethyl cellulose, carboxyethyl cellulose, sulfoethyl cellulose, sulfopropyl cellulose, cellulose sulfate, phosphorylated cellulose, carboxymethyl hydroxyethyl cellulose, carboxymethyl hydroxypropyl cellulose, sulfoethyl hydroxyethyl cellulose, sulfoethyl hydroxypropyl cellulose, carboxymethyl methyl hydroxyethyl cellulose, carboxymethyl methyl cellulose, sulfoethyl methyl hydroxyethyl cellulose, sulfoethyl methyl cellulose, carboxymethyl ethyl hydroxyethyl cellulose, carboxymethyl ethyl cellulose, sulfoethyl ethyl hydroxyethyl cellulose, sulfoethyl ethyl cellulose, carboxymethyl methyl hydroxypropyl cellulose, sulfoethyl methyl hydroxypropyl cellulose, carboxymethyl dodecyl cellulose, carboxymethyl dodecoyl cellulose, carboxymethyl cyanoethyl cellulose, and sulfoethyl cyanoethyl cellulose. The cellulose may be a substituted cellulose substituted by two or more different substituents, such as methyl and hydroxyethyl cellulose.

The composition may comprise soil release polymers, such as Repel-o-Tex™. Other suitable soil release polymers are anionic soil release polymers. Suitable soil release polymers are described in more detail in WO05123835A1, WO07079850A1 and WO08110318A2.

The composition may comprise a spray-dried powder. The spray-dried powder may comprise a silicate salt, such as sodium silicate.

Amphiphilic Alkoxylated Grease Cleaning Polymer

Amphiphilic alkoxylated grease cleaning polymers of the present invention refer to any alkoxylated polymers having balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure.

The core structure may comprise a polyalkylenimine structure comprising, in condensed form, repeating units of formulae (I), (II), (III) and (IV):

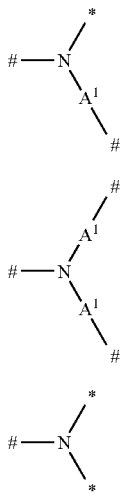

(II)

(III)

(IV)

wherein # in each case denotes one-half of a bond between a nitrogen atom and the free binding position of a group $A^1$ of two adjacent repeating units of formulae (I), (II), (III) or (IV); * in each case denotes one-half of a bond to one of the alkoxylate groups; and $A^1$ is independently selected from linear or branched $C_2$-$C_6$-alkylene; wherein the polyalkylenimine structure consists of 1 repeating unit of formula (I), x repeating units of formula (II), y repeating units of formula (III) and y+1 repeating units of formula (IV), wherein x and y in each case have a value in the range of from 0 to about 150; where the average weight average molecular weight, Mw, of the polyalkylenimine core structure is a value in the range of from about 60 to about 10,000 g/mol.

The core structure may alternatively comprise a polyalkanolamine structure of the condensation products of at least one compound selected from N-(hydroxyalkyl)amines of formulae (I.a) and/or (I.b),

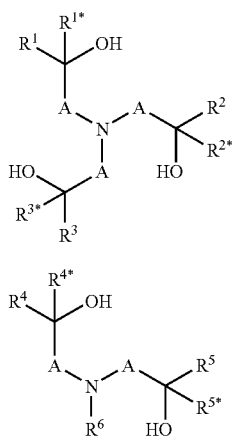

wherein A are independently selected from $C_1$-$C_6$-alkylene; $R^1$, $R^{1*}$, $R^2$, $R^{2*}$, $R^3$, $R^{3*}$, $R^{4*}$, $R^5$ and $R^{5*}$ are independently selected from hydrogen, alkyl, cycloalkyl or aryl, wherein the last three mentioned radicals may be optionally substituted; and $R^6$ is selected from hydrogen, alkyl, cycloalkyl or aryl, wherein the last three mentioned radicals may be optionally substituted.

The plurality of alkylenoxy groups attached to the core structure are independently selected from alkylenoxy units of the formula (V)

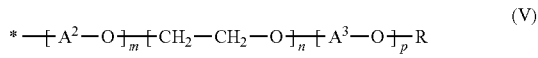

(V)

wherein * in each case denotes one-half of a bond to the nitrogen atom of the repeating unit of formula (I), (II) or (IV); $A^2$ is in each case independently selected from 1,2-propylene, 1,2-butylene and 1,2-isobutylene; $A^3$ is 1,2-propylene; R is in each case independently selected from hydrogen and $C_1$-$C_4$-alkyl; m has an average value in the range of from 0 to about 2; n has an average value in the range of from about 20 to about 50; and p has an average value in the range of from about 10 to about 50.

Specific embodiments of the amphiphilic alkoxylated grease cleaning polymers may be selected from alkoxylated polyalkylenimines having an inner polyethylene oxide block and an outer polypropylene oxide block, the degree of ethoxylation and the degree of propoxylation not going above or below specific limiting values. Specific embodiments of the alkoxylated polyalkylenimines according to the present invention have a minimum ratio of polyethylene blocks to polypropylene blocks (n/p) of about 0.6 and a maximum of about 1.5 $(x+2y+1)^{1/2}$. Alkoxykated polyalkyenimines having an n/p ratio of from about 0.8 to about 1.2 $(x+2y+1)^{1/2}$ have been found to have especially beneficial properties.

The alkoxylated polyalkylenimines according to the present invention have a backbone which consists of primary, secondary and tertiary amine nitrogen atoms which are attached to one another by alkylene radicals A and are randomly arranged. Primary amino moieties which start or terminate the main chain and the side chains of the polyalkylenimine backbone and whose remaining hydrogen atoms are subsequently replaced by alkylenoxy units are referred to as repeating units of formulae (I) or (IV), respectively. Secondary amino moieties whose remaining hydrogen atom is subsequently replaced by alkylenoxy units are referred to as repeating units of formula (II). Tertiary amino moieties which branch the main chain and the side chains are referred to as repeating units of formula (III).

Since cyclization can occur in the formation of the polyalkylenimine backbone, it is also possible for cyclic amino moieties to be present to a small extent in the backbone. Such polyalkylenimines containing cyclic amino moieties are of course alkoxylated in the same way as those consisting of the noncyclic primary and secondary amino moieties.

The polyalkylenimine backbone consisting of the nitrogen atoms and the groups $A^1$, has an average molecular weight Mw of from about 60 to about 10,000 g/mole, preferably from about 100 to about 8,000 g/mole and more preferably from about 500 to about 6,000 g/mole.

The sum (x+2y+1) corresponds to the total number of alkylenimine units present in one individual polyalkylenimine backbone and thus is directly related to the molecular weight of the polyalkylenimine backbone. The values given in the specification however relate to the number average of all polyalkylenimines present in the mixture. The sum (x+2y+2) corresponds to the total number amino groups present in one individual polyalkylenimine backbone.

The radicals $A^1$ connecting the amino nitrogen atoms may be identical or different, linear or branched $C_2$-$C_6$-alkylene radicals, such as 1,2-ethylene, 1,2-propylene, 1,2-butylene, 1,2-isobutylene, 1,2-pentanediyl, 1,2-hexanediyl or hexamethylen. A preferred branched alkylene is 1,2-propylene. Preferred linear alkylene are ethylene and hexamethylene. A more preferred alkylene is 1,2-ethylene.

The hydrogen atoms of the primary and secondary amino groups of the polyalkylenimine backbone are replaced by alkylenoxy units of the formula (V).

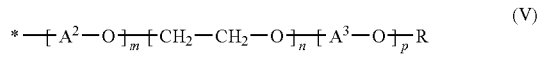
(V)

In this formula, the variables preferably have one of the meanings given below:

$A^2$ in each case is selected from 1,2-propylene, 1,2-butylene and 1,2-isobutylene; preferably $A^2$ is 1,2-propylene. $A^3$ is 1,2-propylene; R in each case is selected from hydrogen and $C_1$-$C_4$-alkyl, such as methyl, ethyl, n-propyl, isopropyl, n-butyl, isobutyl and tert.-butyl; preferably R is hydrogen. The index m in each case has a value of 0 to about 2; preferably m is 0 or approximately 1; more preferably m is 0. The index n has an average value in the range of from about 20 to about 50, preferably in the range of from about 22 to about 40, and more preferably in the range of from about 24 to about 30. The index p has an average value in the range of from about 10 to about 50, preferably in the range of from about 11 to about 40, and more preferably in the range of from about 12 to about 30.

Preferably the alkylenoxy unit of formula (V) is a non-random sequence of alkoxylate blocks. By non-random sequence it is meant that the $[-A^2O—]_m$ is added first (i.e., closest to the bond to the nitrgen atom of the repeating unit of formula (I), (II), or (III)), the $[—CH_2—CH_2—O—]_n$ is added second, and the $[-A^3-O—]_p$ is added third. This orientation provides the alkoxylated polyalkylenimine with an inner polyethylene oxide block and an outer polypropylene oxide block.

The substantial part of these alkylenoxy units of formula (V) is formed by the ethylenoxy units —[$CH_2$—$CH_2$—O]$_n$— and the propylenoxy units —[$CH_2$—$CH_2(CH_3)$—O]$_p$—. The alkylenoxy units may additionally also have a small proportion of propylenoxy or butylenoxy units -[$A^2$-O]$_m$—, i.e. the polyalkylenimine backbone saturated with hydrogen atoms may be reacted initially with small amounts of up to about 2 mol, especially from about 0.5 to about 1.5 mol, in particular from about 0.8 to about 1.2 mol, of propylene oxide or butylene oxide per mole of NH-moieties present, i.e. incipiently alkoxylated.

This initial modification of the polyalkylenimine backbone allows, if necessary, the viscosity of the reaction mixture in the alkoxylation to be lowered. However, the modification generally does not influence the performance properties of the alkoxylated polyalkylenimine and therefore does not constitute a preferred measure.

The amphiphilic alkoxylated grease cleaning polymers are present in the detergent and cleaning compositions of the present invention at levels ranging from about 0.05% to 10% by weight of the composition. Embodiments of the compositions may comprise from about 0.1% to about 5% by weight. More specifically, the embodiments may comprise from about 0.25 to about 2.5% of the grease cleaning polymer.

Detersive Surfactant

The composition comprises detersive surfactant. The detersive surfactant can be anionic, non-ionic, cationic and/or zwitterionic. Preferably, the detersive surfactant is anionic. The compositions preferably comprise from 2% to 50% surfactant, more preferably from 5% to 30%, most preferably from 7% to 20% detersive surfactant. The composition may comprise from 2% to 6% detersive surfactant. The composition preferably comprises detersive surfactant in an amount to provide from 100 ppm to 5,000 ppm detersive surfactant in the wash liquor during the laundering process. This is especially preferred when from 10 g to 125 g of liquid laundry detergent composition is dosed into the wash liquor during the laundering process. The composition upon contact with water typically forms a wash liquor comprising from 0.5 g/l to 10 g/l detergent composition.

Random Graft Co-Polymer

The random graft co-polymer comprises: (i) hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and (ii) hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof.

The polymer preferably has the general formula:

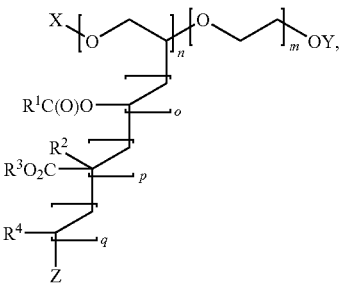

wherein X, Y and Z are capping units independently selected from H or a $C_{1-6}$ alkyl; each $R^1$ is independently selected from methyl and ethyl; each $R^2$ is independently selected from H and methyl; each $R^3$ is independently a $C_{1-4}$ alkyl; and each $R^4$ is independently selected from pyrrolidone and phenyl groups. The weight average molecular weight of the polyethylene oxide backbone is typically from about 1,000 g/mol to about 18,000 g/mol, or from about 3,000 g/mol to about 13,500 g/mol, or from about 4,000 g/mol to about 9,000 g/mol. The value of m, n, o, p and q is selected such that the pendant groups comprise, by weight of the polymer at least 50%, or from about 50% to about 98%, or from about 55% to about 95%, or from about 60% to about 90%. The polymer useful herein typically has a weight average molecular weight of from about 1,000 to about 100,000 g/mol, or preferably from about 2,500 g/mol to about 45,000 g/mol, or from about 7,500 g/mol to about 33,800 g/mol, or from about 10,000 g/mol to about 22,500 g/mol.

Suitable graft co-polymers are described in more detail in WO07/138054, WO06/108856 and WO06/113314.

Suitable Fabric Hueing Agents

Fluorescent optical brighteners emit at least some visible light. In contrast, fabric hueing agents can alter the tint of a surface as they absorb at least a portion of the visible light spectrum. Suitable fabric hueing agents include dyes, dye-clay conjugates, and pigments that satisfy the requirements of Test Method 1 in the Test Method Section of the present specification. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example:

(1) Tris-Azo Direct Blue Dyes of the Formula

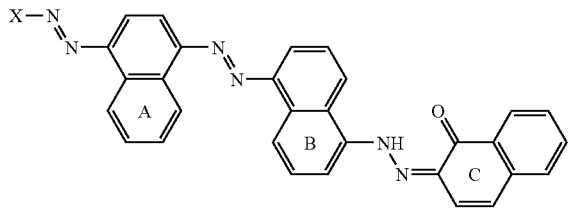

where at least two of the A, B and C napthyl rings are substituted by a sulfonate group, the C ring may be substituted at the 5 position by an NH₂ or NHPh group, X is a benzyl or naphthyl ring substituted with up to 2 sulfonate groups and may be substituted at the 2 position with an OH group and may also be substituted with an NH₂ or NHPh group.

(2) Bis-Azo Direct Violet Dyes of the Formula:

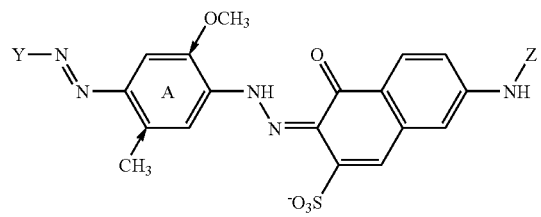

where Z is H or phenyl, the A ring is preferably substituted by a methyl and methoxy group at the positions indicated by arrows, the A ring may also be a naphthyl ring, the Y group is a benzyl or naphthyl ring, which is substituted by sulfate group and may be mono or disubstituted by methyl groups.

(3) Blue or Red Acid Dyes of the Formula

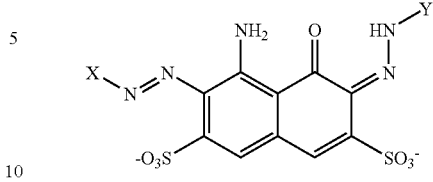

where at least one of X and Y must be an aromatic group. In one aspect, both the aromatic groups may be a substituted benzyl or naphthyl group, which may be substituted with non water-solubilising groups such as alkyl or alkyloxy or aryloxy groups, X and Y may not be substituted with water solubilising groups such as sulfonates or carboxylates. In another aspect, X is a nitro substituted benzyl group and Y is a benzyl group (4) Red Acid Dyes of the Structure

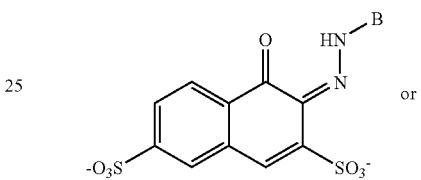

or

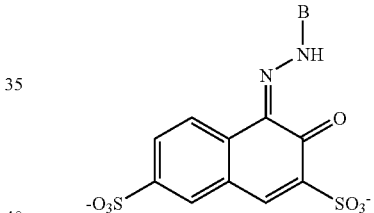

where B is a naphthyl or benzyl group that may be substituted with non water solubilising groups such as alkyl or alkyloxy or aryloxy groups, B may not be substituted with water solubilising groups such as sulfonates or carboxylates.

(5) Dis-Azo Dyes of the Structure

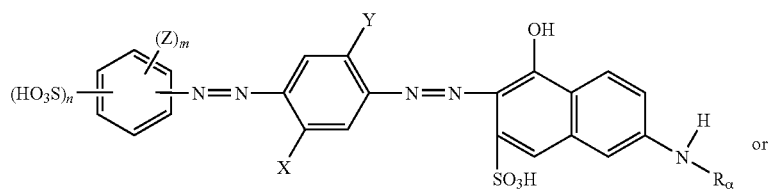

or

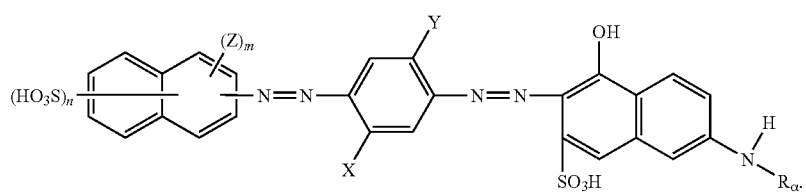

wherein X and Y, independently of one another, are each hydrogen, $C_1$-$C_4$ alkyl or $C_1$-$C_4$-alkoxy, R is hydrogen or aryl, Z is $C_1$-$C_4$ alkyl; $C_1$-$C_4$-alkoxy; halogen; hydroxyl or carboxyl, n is 1 or 2 and m is 0, 1 or 2, as well as corresponding salts thereof and mixtures thereof
(6) Triphenylmethane Dyes of the Following Structures
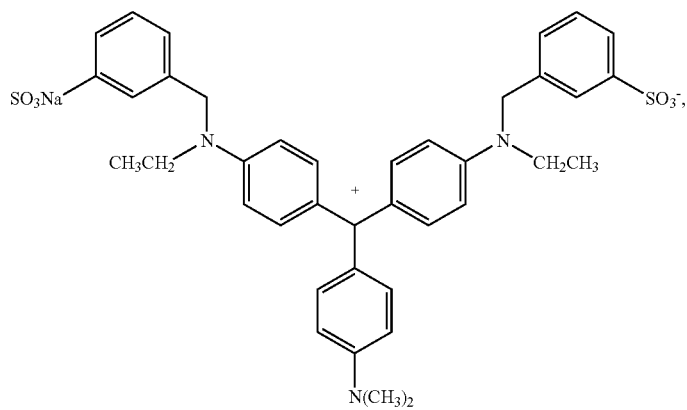
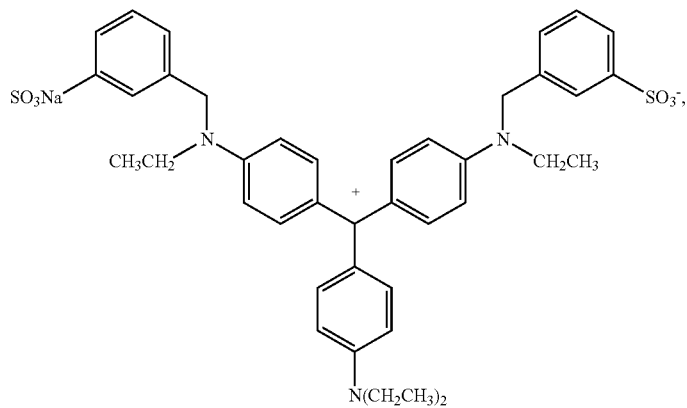
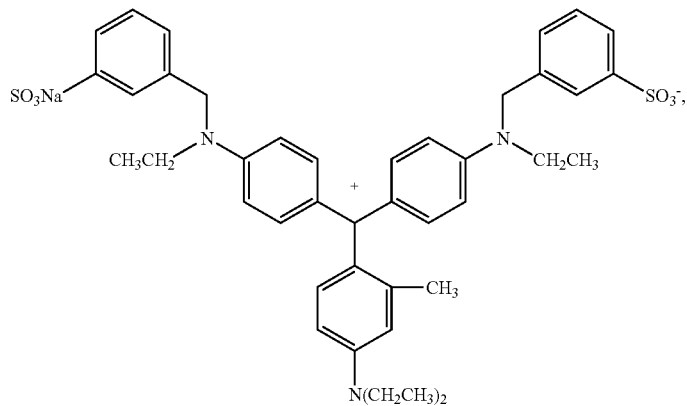

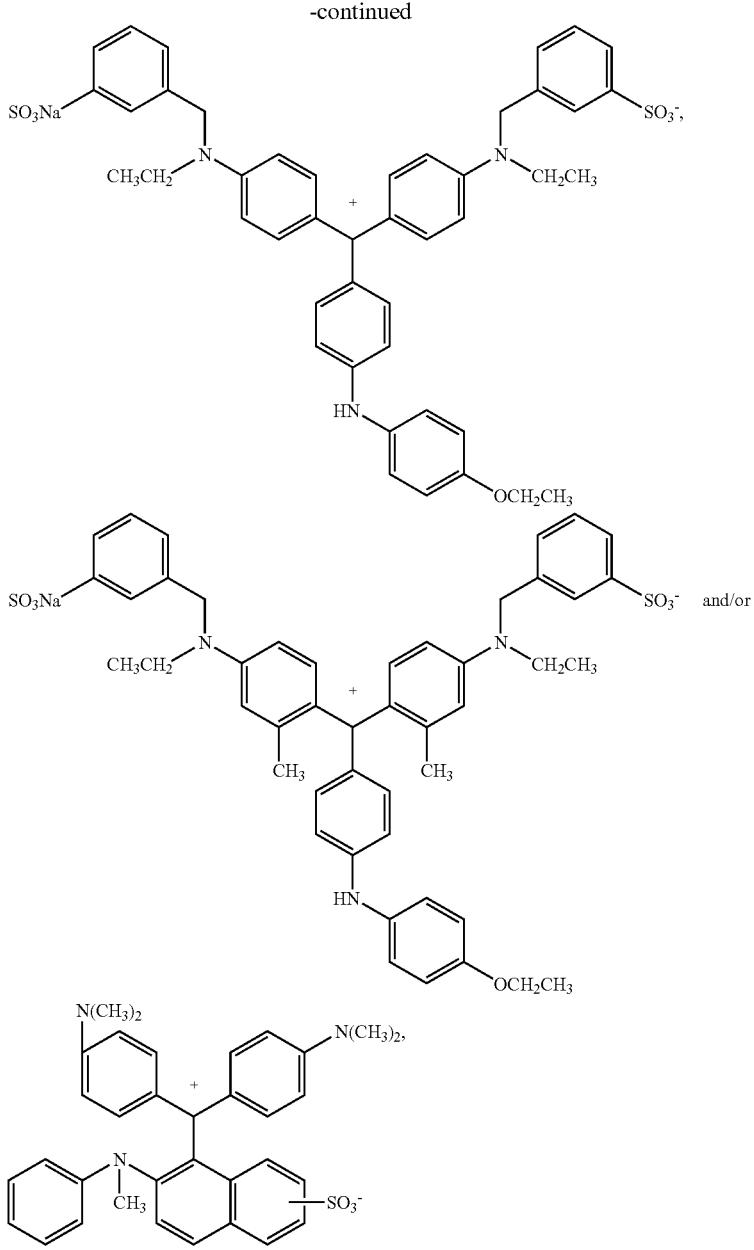

and mixtures thereof. In another aspect, suitable small molecule dyes include small molecule dyes selected from the group consisting of Colour Index (Society of Dyers and Colourists, Bradford, UK) numbers Direct Violet 9, Direct Violet 35, Direct Violet 48, Direct Violet 51, Direct Violet 66, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof. In another aspect, suitable small molecule dyes include small molecule dyes selected from the group consisting of Colour Index (Society of Dyers and Colourists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71, Direct Violet 51 and mixtures thereof. In another aspect, suitable small molecule dyes include small molecule dyes selected from the group consisting of Colour Index (Society of Dyers and Colourists, Bradford, UK) numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable fabric hueing agents can be purchased from Aldrich, Milwaukee, Wis., USA; Ciba Specialty Chemicals, Basel, Switzerland; BASF, Ludwigshafen, Germany; Dayglo Color Corporation, Mumbai, India; Organic Dyestuffs Corp., East Providence, R.I., USA; Dystar, Frankfurt, Germany; Lanxess, Leverkusen, Germany; Megazyme, Wicklow, Ireland; Clariant, Muttenz, Switzerland; Avecia, Manchester, UK and/or made in accordance with the examples contained herein.

Suitable hueing agents are described in more detail in U.S. Pat. No. 7,208,459 B2.

Adjunct Ingredients

Suitable adjunct materials include, but are not limited to, surfactants, builders, chelating agents, dye transfer inhibiting agents, dispersants, additional enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents and/or pigments. In addition to the disclosure below, suitable examples of such other adjuncts and levels of use are found in U.S. Pat. Nos. 5,576,282, 6,306,812 and 6,326,348.

The present invention is further described by the following examples that should not be construed as limiting the scope of the invention.

EXAMPLES

Example 1

Production and Purification of Xyloglucanase Variants

The xyloglucanase variants of the present invention were prepared by standard procedures, in brief: Introducing random and/or site-directed mutations into the gene, transforming *Bacillus subtilis* host cells with the mutated genes, fermenting the transformed host cells, and obtaining the xyloglucanase variant from the fermentation broth. The reference xyloglucanase (SEQ ID NO: 3) was produced recombinantly in *Bacillus subtilis* in a similar manner.

Fermentation was carried out in shake flask cultures at 37° C. for 4 days shaking of 100 ml PS-1 medium containing one CaCO3 tablet (0.5 g) in a baffled 500 ml Erlenmeyer flask. The PS-1 medium composition contains 100 g/L sucrose, 40 g/L Soymeal Meal, 10 g/L $Na_2HPO_4*12H_2O$, 0.1 ml/L Dowfax 63N10 and antibiotic in the form of 6 μg/ml chloramphenicol.

After fermentation the culture broth was harvested by centrifugation (26000×g, 20 min). A small volume of the supernatant was sterile filtered through a 0.45 μm filter, and stored frozen. The samples were allowed to thaw immediately before the stability assays described below were started.

In some cases the enzyme samples were purified before they were used for the stability test.

For enzyme purification the supernatants were filtered through a NALGENE 0.2 μm Filtration unit (cat. no. 569-0020) in order to remove the rest of the host cells. The pH of the 0.2 μm filtrate was adjusted to pH 5.0 with 20% $CH_3COOH$ and the filtrate was applied to an XpressLine ProA column (UpFront chromatography A/S) equilibrated in 50 mM succinic acid/NaOH, 1 mM $CaCl_2$, pH 5.0. After washing the XpressLine ProA column extensively with the equilibration buffer, the xyloglucanase was eluted by a step-elution with 50 mM Tris/HCl, pH 9.0. Fractions were collected during elution. Fractions from the column were analysed for xyloglucanase activity (Example 2) and fractions with activity were pooled. The pH of the pool was adjusted to pH 9.0 with 3M Tris base and the pool was diluted with demineralised water to the same (or lower) conductivity as 50 mM Tris/HCl, pH 9.0. The adjusted solution was applied to a SOURCE Q column (GE Healthcare) equilibrated in 50 mM Tris/HCl, pH 9.0. After washing the SOURCE Q column extensively with the equilibration buffer, the enzyme was eluted with a linear NaCl gradient (0→0.5M) in the same buffer over five column volumes. Fractions from the column were again analysed for xyloglucanase activity and active fractions were further analysed by SDS-PAGE. Fractions, where only one band was seen on the Coomassie stained SDS-PAGE gel, were pooled as the purified preparation.

Example 2

Xyloglucanase Assay

The xyloglucanase activity of enzyme samples, e.g. from purification, were measured in an AZCL-xyloglucan assay.

AZCL-xyloglucan (Megazyme) was incubated with the xyloglucanase and the liberated blue colour was measured at 650 nm. The xyloglucanase activity was calculated as the increase in blue colour during incubation after subtraction of the proper blank value.

AZCL-xyloglucan substrate: 4 mg/ml AZCL-xyloglucan (Megazyme) homogeneously suspended in 0.01% Triton X-100 by stirring.
Assay temperature: 37° C.
Assay buffer: 50 mM succinic acid/NaOH, 0.01% Triton X-100, pH 5.0.

500 µl AZCL-xyloglucan substrate suspension was placed on ice in an Eppendorf tube. 500 µl Assay buffer was added and the mixture was allowed to become ice-cold. 20 µl enzyme sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm). The incubation was stopped by transferring the tube back to the ice bath. When the tube had become ice-cold, the tube was centrifuged shortly in an ice-cold centrifuge to precipitate unreacted substrate. 200 µl supernatant was transferred to a microtiter plate and $A_{650}$ was read. A buffer blank (20 µl 0.01% Triton X-100 instead of enzyme) was included in the assay and the difference in $A_{650}$ between enzyme sample and buffer blank was a measure of the xyloglucanase activity.

Example 3

Stability of Xyloglucanase Variants

The detergent stability of the xyloglucanase variants of the present invention was assessed by measuring the activity of the variants after incubation in a liquid detergent.

The stability test was performed by adding an enzyme sample into the liquid detergent and storing it at elevated temperatures, e.g. 35° C. or 40° C. After the prescribed storage time the enzyme activity was determined and compared with the activity of an equivalent sample stored at approximately −18° C. for the same time period. The result of the stability test is the activity found in the sample stored at elevated temperature expressed as % of the activity found in the cold stored sample.

The results for the xyloglucanase variants were compared to the result for the parental xyloglucanase (SEQ ID NO:3), tested under the same conditions. The ratio between these two stability results is the Stability Improvement Factor (SIF).

Variants having a SIF>1 are more stable under the test conditions than the parental xyloglucanase. Preferred variants are those that have high SIF in this test.

Detergent

The liquid detergent used for the stability tests has the following composition

| | |
|---|---|
| Alkylethoxy sulfate | 20.1% |
| alkylbenzene sulfonate | 2.7% |
| alkyl sulfate | 6.5% |
| alkyl ethoxylate | 0.8% |
| citric acid | 3.8% |
| fatty acid | 2.0% |
| Borax | 3.0% |
| Na & Ca formate | 0.2% |
| amine ethoxylate polymers | 3.4% |
| diethylenetriaminepentaacetic acid | 0.4% |
| Tinopal AMS-GX | 0.2% |
| Ethanol | 2.6% |
| Propylene glycol | 4.6% |
| Diethylene glycol | 3.0% |
| polyethylene glycol | 0.2% |
| Monoethanolamine | 2.7% |
| NaOH | To pH 8.3 |
| Minor ingredients (protease, amylase, perfume, dye) | 2.3% |
| Water | balance |

Storage Test

The enzyme samples prepared according to Example 1 were allowed to thaw immediately before starting the storage stability test.

The enzyme samples were diluted to a concentration of approximately 0.25 mg enzyme protein per ml.

The liquid detergent was dispensed into glass bottles with a volume of approximately 12 ml, providing 1.0±0.05 gram of detergent in each glass.

For each enzyme sample two duplicate bottles were prepared. 50 µl diluted enzyme and a small magnetic stirrer bar was added to the bottles and they were closed tightly (to prevent evaporation during storage). The contents were mixed with help of the magnetic stirrer bar for about 5 minutes. One bottle of the pair was placed in a freezer at approximately −18° C. The other bottle was placed in a suitable incubator oven at the prescribed elevated temperature, e.g. 35° C. or 40° C., to be tested. After the prescribed storage time the bottles in the incubator oven are transferred into the freezer.

Activity Assay

The activity of the enzyme samples after storage in detergent was measured using the following procedure.

Materials and Reagents:
1M phosphate buffer pH7:
  Dissolve 138 grams of $NaH_2PO_4.H_2O$ in about 750 ml water. Add 4N NaOH to give pH 7.0. Then make the final volume to 1000 ml.
Assay buffer (50 mM phosphate pH7):
  Mix 950 ml water, 50 ml 1M phosphate buffer pH7 and 5 ml of Berol 537 (nonionic surfactant supplied by Akzo Nobel). Adjust the final pH to 7.00±0.02.
Substrate:
  Cellazyme C tablets, supplied by Megazyme International Ireland Ltd, catalogue number T-CCZ. The tablets contain cross-linked dyed HE cellulose.

Procedure

About 30 minutes prior to starting the assay the bottles were transferred from the freezer into a refrigerator at approximately 4° C. Immediately before starting the assay the bottles were taken out of the refrigerator and placed on the laboratory bench top and opened.

10 ml assay buffer (room temperature) was added to each open bottle. The bottles were then transferred into a 30° C. water bath equipped with a submerged multipoint magnetic stirrer. The contents were stirred gently for about 5 minutes.

One Cellazyme C tablet was added to each bottle. Stirring was continued using a stirrer speed which is just adequate to keep the substrate particles in movement and avoid sedimentation. The bottles were removed from the water bath 30 minutes after addition of the tablet and were then allowed to stand at room temperature with no stirring for 15 minutes.

With a pipette approximately 1 ml of the practically clear supernatant from the top of each bottle was transferred into a semi-micro spectrophotometer cuvette. Absorbance at 590 nm was then measured using a suitable spectrophotometer. All measurements were finished within 15 minutes.

Blank samples, i.e. equivalent detergent samples but containing no added xyloglucanase enzyme, were included in the assay.

Calculation

For each enzyme sample there are two Abs590 measurements:

A590f, which is the Abs590 value of the sample stored at −18° C.

A590w, which is the Abs590 value of the sample stored at elevated temperature.

Subtract the blank value (A590b) from both A590f (giving A590f−A590b) and from A590w (giving A590w−A590b).

The stability was calculated as:

% Stability=((A590w−A590b)/(A590f−A590b))× 100%.

For each enzyme the results for (A590f−A590b) must be in the range 0.1-1.2. If the value is outside this range the result for that enzyme must be regarded as being unreliable and the test should be repeated with a different dilution of the enzyme sample.

Finally the Stability Improvement Factor (SIF) for each enzyme variant is calculated as follows:

SIF=% stability of enzyme sample/% stability of parent enzyme (SEQ ID NO: 3)

Results

Below are the stability results of xyloglucanase variants tested under different conditions.

TABLE 1

Sterile filtered enzyme samples stored for 18 hours at 40° C.

| Mutations | SIF |
|---|---|
| K8Q | 1.1 |
| K8A | 1.2 |
| K13A | 1.1 |
| K18R | 1.1 |
| K87Q | 1.1 |
| K129A | 1.7 |
| K169Q | 1.3 |
| K169R | 1.4 |
| K169A | 1.3 |
| N140F | 1.2 |
| G316I | 1.1 |
| F418I | 1.1 |
| L34I | 1.1 |

TABLE 1-continued

Sterile filtered enzyme samples stored for 18 hours at 40° C.

| Mutations | SIF |
|---|---|
| L166I | 1.1 |
| L268I | 1.1 |
| L278I | 1.3 |
| V1* + V2* + H3* | 1.2 |
| *0aE + *0bV | 1.3 |
| F146L | 1.2 |
| Q137E | 1.6 |
| R156Y | 2.2 |
| R156Q | 1.5 |
| K8S | 1.2 |
| K21T | 1.4 |
| K176P | 1.1 |
| K445S | 1.4 |
| K470T | 1.2 |

TABLE 2

Purified enzyme samples stored for 18 hours at 40° C.

| Mutations | SIF |
|---|---|
| K87Q | 1.1 |
| K129A | 1.8 |
| K169A | 1.1 |
| A7T + G200P + A224P + G225K + R267K + L268K + S269A | 1.3 |
| H164N + V179I + G200A + R267K | 1.2 |
| H164N + V179I + G200A + R211K + G225D + F281L | 1.5 |
| H164N + G200A + G225N + R267K | 1.2 |

TABLE 3

Sterile filtered enzyme samples stored for 24 hours at 40° C.

| Mutations | SIF |
|---|---|
| K101R + L102I | 1.1 |
| K217A | 1.1 |
| L380F | 1.1 |
| N383Y | 1.2 |
| G78A | 1.2 |
| M310V | 1.2 |
| N399I | 1.1 |
| G498S | 1.1 |
| F146L | 1.1 |
| Q137E | 1.4 |
| R156Y | 2.0 |
| V1* + V2* + H3* + G4* + Q5* | 1.1 |
| N331F | 1.2 |
| K8S | 1.1 |
| T92V | 1.3 |
| K176P | 1.2 |
| G253A | 1.1 |
| K445S | 1.3 |
| K470T | 1.2 |

TABLE 4

Purified enzyme samples stored for 24 hours at 40° C.

| Mutations | SIF |
|---|---|
| T92V | 1.2 |
| Q137E | 1.5 |
| R156Y | 1.7 |
| R156Q | 1.2 |

TABLE 5

Sterile filtered enzyme samples stored for 30 hours at 40° C.

| Mutations | SIF |
|---|---|
| K118R | 1.1 |
| K118A | 1.7 |
| K129A + K169A | 1.6 |
| G200P | 1.5 |
| K129A + R156Y | 2.0 |
| K129A + Q137E + R156Y | 2.2 |
| K129A + R156Y + H164N | 2.1 |

TABLE 6

Purified enzyme samples stored for 30 hours at 40° C.

| Mutations | SIF |
|---|---|
| T92V | 1.3 |
| R156Y | 1.9 |
| K129A + R156Y | 2.1 |

TABLE 7

Sterile filtered enzyme samples stored for 48 hours at 40° C.

| Mutations | SIF |
|---|---|
| K118A | 3.0 |
| K252Q | 1.1 |
| K252R | 1.2 |
| K252A | 1.1 |
| K275Q | 1.1 |
| K275R | 1.2 |
| K275A | 1.1 |
| K306R | 1.1 |
| K306A | 1.1 |
| K347Q | 1.1 |
| K347R | 1.1 |
| K347A | 1.1 |
| K382A | 1.1 |
| K414A | 1.2 |
| K445R | 1.3 |
| K454R | 1.1 |
| K476Q | 1.1 |
| K482Q | 1.1 |
| K482A | 1.1 |
| K488Q | 1.1 |
| K488R | 1.1 |
| K488A | 1.1 |
| M40V | 1.4 |
| R156Y | 2.9 |
| G200P | 1.8 |
| K129A + R156Y | 3.5 |
| K129A + Q137E + R156Y + K470T | 3.7 |
| K406N | 1.1 |
| K445S | 1.2 |
| K488T | 1.2 |
| T92V + K129A + R156Y | 3.7 |
| K118A + K129A + R156Y | 3.8 |
| T92V + K118A + K129A + R156Y | 3.9 |
| K129A + R156Y + P507A | 3.2 |
| K129A + R156Y + S443D + K445S + L449I + V450I + S455N + M456Y | 3.8 |
| K129A + R156Y + H436Y | 3.9 |
| K129A + R156Y + K406N + N415G | 3.5 |
| K129A + R156Y + L380F + N383Y + D384G + N389T | 3.5 |
| K129A + R156Y + D366H + T374A | 3.4 |
| K129A + R156Y + A328G | 3.5 |
| K129A + R156Y + V259I + R267K + L268K + S269A | 3.5 |
| K129A + R156Y + T244D | 3.4 |
| K129A + R156Y + I222V + A224P + V228I + V232A | 2.0 |
| K129A + R156Y + G200P + G204T + R211K | 3.6 |
| K129A + R156Y + A177T + V179I + A183S | 2.9 |
| K129A + R156Y + V159M + H164N + F165Y | 2.8 |

TABLE 7-continued

Sterile filtered enzyme samples stored for 48 hours at 40° C.

| Mutations | SIF |
|---|---|
| K129A + R156Y + I10V + V14I + D19E | 4.0 |
| T104A + P111Q + A117S + K129A + R156Y | 2.1 |
| S123T + K129A + R156Y | 3.8 |
| K129A + Q137E + V139K + N140F + Q147S + R156Y | 2.9 |
| K129A + R156Y + D324N | 3.4 |
| K129A + R156Y + K176P | 3.2 |
| K129A + R156Y + D249N | 3.2 |
| K129A + R156Y + D249G | 3.3 |
| K129A + R156Y + D249S | 3.1 |
| K129A + R156Y + D461N | 3.6 |
| K129A + R156Y + D461T | 3.9 |
| K129A + R156Y + D461Q | 4.0 |
| K129A + R156Y + R409T | 3.8 |
| K129A + R156Y + R409L | 3.6 |
| K129A + R156Y + D247G | 1.4 |
| K129A + R156Y + E288Q | 2.7 |
| D37G + K129A + R156Y | 3.9 |
| D37N + K129A + R156Y | 3.6 |
| K129A + R156Y + R267H | 3.8 |
| K129A + R156Y + D303I | 4.1 |
| K129A + R156Y + D303K | 3.7 |
| K129A + R156Y + K275T | 3.5 |
| K129A + R156Y + G200P | 3.9 |
| K129A + R156Y + N331F | 3.8 |
| R156Y + N331F | 3.2 |
| K118A + K129A + R156Y + K470T | 4.4 |
| K470R | 1.1 |
| K470P | 1.2 |
| G413A | 1.1 |
| K118A + K129A + R156Y + A224P | 3.9 |
| D119L | 1.3 |
| K87V + K129A + K169A | 1.9 |
| K129A + K445S | 1.8 |
| K118A + K129A + R156Y + G200P | 3.8 |
| K118A + K129A + R156Y + G200P + N331F | 4.2 |
| G78A + K118A + K129A + R156Y | 3.8 |
| G78A + T92V + K118A + K129A + R156Y | 3.8 |
| T92V + K118A + K129A + R156Y | 3.7 |
| M310V + N399I | 1.7 |
| L34I + K129A | 1.9 |
| K101A + K129A | 1.8 |
| K13A + K129A | 2.0 |
| K129A + K470T | 1.8 |
| K129A + K176P | 1.9 |
| G78A + T92V + K118A + K129A + R156Y + K169A | 4.8 |
| K118A + K129A + R156Y + K169A + G200P + N331F | 4.7 |
| K118A + K129A + R156Y + G200P + M310V + N331F | 4.7 |
| K129A + R156Y + K454Q | 3.8 |
| G78A + K118A + K129A + R156Y + G200P + N331F | 4.2 |
| T92V + K118A + K129A + R156Y + G200P + N331F | 4.3 |
| K129A + R156Y + N302K + D303S | 2.9 |
| K129A + R156Y + N302K + D303L | 2.7 |
| S332P + V397I | 1.1 |
| K129A + R156Y + K322I + K454Q | 2.3 |
| Q68H + K118A + K129A + R156Y + G200P + N331F | 4.1 |
| Q68H + T92S + K118A + K129A + R156Y + G200P + N331F | 5.2 |
| Q68H + T92A + K118A + K129A + R156Y + G200P + N331F | 4.7 |
| Q68H + K118A + K129A + R156Y + G200P + N331F | 5.0 |
| Q68H + K118A + K129A + R156Y + G200P + N331F | 5.7 |
| Q68H + T92D + K118A + K129A + R156Y + G200P + N331F | 3.3 |
| Q68H + T92I + K118A + K129A + R156Y + G200P + N331F | 4.4 |
| Q68H + K118A + K129A + R156Y + G200P + N331F | 4.4 |
| Q68H + T92V + K118A + K129A + R156Y + G200P + N331F | 4.2 |
| K129S | 1.1 |
| K129A | 1.5 |
| R156M | 1.3 |
| R156F | 2.3 |
| R156W | 1.6 |
| R156L | 1.4 |
| R156V | 2.2 |
| G396P | 1.3 |
| G413S | 1.1 |
| A177T | 1.1 |
| E38I | 1.1 |
| E38V | 1.2 |
| G36V + D37A + E38* + N39* | 1.2 |

TABLE 7-continued

Sterile filtered enzyme samples stored for 48 hours at 40° C.

| Mutations | SIF |
|---|---|
| T104A | 1.2 |
| L102A + T104V + *104P | 1.3 |
| Q68L | 1.3 |
| Q68H | 3.6 |
| N389A | 1.1 |
| G468Y | 1.1 |
| G237V | 1.1 |

TABLE 8

Purified enzyme samples stored for 48 hours at 40° C.

| Mutations | SIF |
|---|---|
| K118A | 2.3 |
| R156Y | 2.5 |
| K129A + K169A | 1.7 |
| G200P | 1.5 |
| K129A + R156Y | 1.7 |
| K129A + Q137E + R156Y | 3.7 |
| K129A + R156Y + H164N | 3.5 |
| K129A + Q137E + R156Y + K470T | 4.2 |
| T92V + K129A + R156Y | 4.5 |
| K118A + K129A + R156Y | 3.8 |
| K129A + R156Y + G200P | 4.8 |
| K129A + R156Y + N331F | 4.1 |
| R156Y + N331F | 3.5 |
| K118A + K129A + R156Y + G200P, | 4.2 |
| K118A + K129A + R156Y + G200P + N331F | 4.5 |
| G78A + K118A, + K129A + R156Y | 4.0 |
| G78A + T92V + K118A + K129A + R156Y | 4.3 |
| Q68H | 3.7 |

TABLE 9

Sterile filtered enzyme samples stored for 72 hours at 40° C.

| Mutations | SIF |
|---|---|
| K13R | 1.3 |
| K206Q | 1.1 |
| K129A + R156Y | 5.1 |
| K129A + Q137E + R156Y + K470T | 6.4 |
| T92V + K129A + R156Y | 6.6 |
| K118A + K129A + R156Y | 7.2 |
| K129A + R156Y + G200P | 7.7 |
| K129A + R156Y + N331F | 5.9 |
| R156Y + N331F | 5.3 |

TABLE 10

Sterile filtered enzyme samples stored for one week at 35° C.

| Mutations | SIF |
|---|---|
| K8Q | 1.4 |
| K8A | 1.1 |
| K13Q | 1.1 |
| K18Q | 1.1 |
| K18A | 1.4 |
| K21Q | 1.4 |
| K21R | 1.4 |
| K21A | 1.4 |
| K87Q | 1.3 |
| K101R | 1.3 |
| K101A | 1.6 |
| K118R | 1.4 |
| K118A | 2.3 |
| K101R + L102I | 1.1 |
| K129A | 2.1 |
| K169Q | 1.4 |
| K169R | 1.5 |
| K169A | 1.5 |
| K220Q | 1.3 |
| K220A | 1.2 |
| K252Q | 1.1 |
| K252R | 1.1 |
| K275Q | 1.1 |
| K275R | 1.1 |
| K275A | 1.1 |
| K306R | 1.1 |
| K306A | 1.1 |
| K307Q | 1.2 |
| K307R | 1.1 |
| K454Q | 1.6 |
| K454R | 1.2 |
| K476Q | 1.3 |
| K476R | 1.3 |
| K476A | 1.2 |
| K482Q | 1.2 |
| K482A | 1.2 |
| K488Q | 1.2 |
| K488R | 1.2 |
| K488A | 1.1 |
| N140F | 1.7 |
| G78A | 1.2 |
| M310V | 1.3 |
| G316I | 1.1 |
| W391V | 1.1 |
| N399I | 1.4 |
| L34I | 1.3 |
| L268I | 1.1 |
| L278I | 1.2 |
| G498S | 1.2 |
| *0aE + *0bV | 1.4 |
| F146L | 2.3 |
| Q137E | 2.0 |
| R156Y | 3.2 |
| R156Q | 1.7 |
| N331F | 1.5 |
| K8S | 1.3 |
| K21T | 1.5 |
| K176P | 1.2 |
| G253A | 1.1 |
| K445S | 1.5 |
| K470T | 1.6 |
| F146C | 1.3 |
| K129A + K169A | 1.8 |
| G200P | 1.7 |
| A224P | 1.1 |
| K129A + R156Y | 2.6 |
| K129A + Q137E + R156Y | 2.6 |
| K129A + R156Y + H164N | 2.6 |
| K406N | 1.3 |
| K445S | 1.2 |
| K488T | 1.2 |
| K129R | 1.1 |
| R156F | 2.0 |

TABLE 11

Purified enzyme samples stored for one week at 35° C.

| Mutations | SIF |
|---|---|
| K101R | 1.1 |
| K101A | 1.1 |
| K118A | 2.3 |
| K129A | 1.8 |
| K169R | 1.2 |
| K169A | 1.1 |
| T92V | 2.0 |

TABLE 11-continued

Purified enzyme samples stored for one week at 35° C.

| Mutations | SIF |
|---|---|
| F418I | 1.1 |
| del(V1-Q5) | 1.2 |
| Q137E | 1.6 |
| R156Y | 2.5 |
| R156Q | 1.2 |
| K21T | 1.1 |
| G200P | 1.7 |
| K129A + R156Y | 2.7 |
| K129A + Q137E + R156Y | 3.0 |
| K129A + R156Y + H164N | 3.1 |
| A7T + G200P + A224P + G225K + R267K + L268K + S269A | 1.3 |
| H164N + V179I + G200A + R267K | 1.3 |
| H164N + V179I + G200A + R211K + G225D + F281L | 1.8 |
| H164N + G200A + G225N + R267K | 1.6 |

TABLE 12

Purified enzyme samples stored for 16 hours at 44° C.

| Mutation | SIF |
|---|---|
| Q68H | 5.8 |
| S123P | 4.4 |
| R156Y | 4.0 |
| K118A | 2.9 |
| G200P | 2.6 |
| K129A | 2.4 |
| Q137E | 2.4 |
| H193T | 2.1 |
| T92V | 2.0 |
| S76W | 1.7 |

Example 4

Stability of Xyloglucanase Variants

The detergent stability of the xyloglucanase variants of the present example was assessed by measuring the activity of the variants after incubation in a liquid detergent.

The stability test was performed by adding an enzyme sample into the liquid detergent and storing it at elevated temperatures, e.g. 35° C. or 46° C. After the prescribed storage time the enzyme activity was determined and compared with the activity of an identical sample that had been stored cold at approximately +5° C. for the same time period. The result of the stability test is the activity found in the sample stored at elevated temperature (the stressed sample) expressed as % of the activity found in the equivalent cold-stored sample (the unstressed sample).

The results for the xyloglucanase variants were compared to the result for the parental xyloglucanase (SEQ ID NO:3), tested under the same conditions.

Detergent

The liquid detergent used for the stability tests has the following composition

| Alkylethoxy sulfate | 20.1% |
|---|---|
| alkylbenzene sulfonate | 2.7% |
| alkyl sulfate | 6.5% |
| alkyl ethoxylate | 0.8% |
| citric acid | 3.8% |
| fatty acid | 2.0% |
| Borax | 3.0% |
| Na & Ca formate | 0.2% |
| amine ethoxylate polymers | 3.4% |
| diethylenetriaminepentaacetic acid | 0.4% |
| Tinopal AMS-GX | 0.2% |
| Ethanol | 2.6% |
| Propylene glycol | 4.6% |
| Diethylene glycol | 3.0% |
| polyethylene glycol | 0.2% |
| Monoethanolamine | 2.7% |
| NaOH | to pH 8.3 |
| Minor ingredients (protease, amylase, perfume, dye) | 2.3% |
| Water | balance |

Storage Test

The enzyme samples prepared according to Example 1 were allowed to thaw immediately before starting the storage stability test.

The enzyme samples were used without further dilution.

The liquid detergent was dispensed into a round-bottom polystyrene 96-well microtiter plate (Plate 1) providing 190 µl of detergent per well.

Ten µl enzyme sample and a small magnetic stirrer bar was added to each well and the plate was closed tightly (to prevent evaporation) using adhesive aluminium foil lids (Beckman Coulter). The contents were mixed with the magnetic stirrer bars for about 30 minutes.

From each well of Plate 1, 20 µl detergent-enzyme mixture was then transferred into a new empty identical plate (Plate 2). Both plates were then sealed.

The original plate (Plate 1) was placed in an incubator oven at the prescribed elevated temperature, e.g. 35° C. or 46° C., to be tested. The other plate (Plate 2) was placed in a refrigerator at approximately 5° C.

Following incubation for the prescribed period, the plates were removed from the refrigerator and the incubator oven. The plates were placed on the laboratory bench for at least half an hour to allow all wells to reach room-temperature.

Then 20 µl from each well of Plate 1 was transferred into a new empty round bottom 96-well plate (Plate 1a).

Plate 1a now contains 20 µl stressed samples and Plate 2 contains 20 µl unstressed samples.

Activity Assay

The activity of the enzyme samples after storage in detergent was measured using the following procedure at room temperature.

Assay Principle:

Para-nitrophenol-beta-D-cellotetraoside (pNP-beta-D-cellotetraoside) is a synthetic substrate that is hydrolysed by the catalytic action of certain xyloglucanase enzymes.

The substrate itself is colourless; however upon hydrolysis of the terminal reducing end glycoside bond, para-nitrophenol is released which is yellow in a pH8 buffer due to a strong absorbance at 405 nm.

pNP-beta-D-cellotetraoside itself is very stable under the given assay conditions. Thus increasing absorbance at 405 nm is an attribute of enzymatic activity.

We found that the parental xyloglucanase (SEQ ID NO:3) accepted pNP-beta-D-cellotetraoside as substrate, as evidenced by the strong absorbance increase at 405 nm.

Materials and Reagents:

Assay Buffer: 100 mM EPPS; 0.01% Tween 20; pH 8.0.

pNP-beta-D-cellotetraoside (CAS-#: 129411-62-7; Toronto Research Chemicals; Canada)

Substrate solution: 1 mM pNP-beta-D-cellotetraoside in assay buffer.

Procedure:

Plate 1a contains 20 μl stressed samples and Plate 2 contains 20 μl unstressed samples.

The samples were diluted by adding 50 μl assay buffer to all wells in Plate 1a and Plate 2, and mixed for one hour using a microtiter plate shaker. Then an additional 50 μl assay buffer was added to all wells and the shaking was continued for an additional 10 minutes.

20 μl of the factor 6 diluted samples were transferred to a transparent 384 well polystyrene microtiter plate, and 20 μl substrate solution was added to all wells. The samples were mixed by shaking the microtiter plate briefly. The kinetic measurement of enzymatic activity was initiated immediately by observing the rate of increasing absorbance at 405 nm using a 384-well spectrophotometric reader.

The initial velocity (Abs/min) of the reaction was determined. The initial velocity of the reaction was a measure of the enzymatic activity in the sample as verified by a linear standard curve within relevant enzyme concentrations.

Calculation:

% residual activity was calculated as enzymatic activity in the stressed sample divided by enzymatic activity in the identical unstressed sample.

% residual activity="Abs/min(stressed sample)"/"Abs/min(not stressed sample)"*100%.

Results

Below are the stability results of xyloglucanase variants tested under different conditions.

TABLE 13

Sterile filtered enzyme samples stored for 16 hours at +44° C.

| Mutations | % Residual Activity |
| --- | --- |
| SEQ ID NO: 3 | 7 |
| K118A | 24 |
| R156Y | 36 |
| K129A + K169A | 19 |
| G200P | 26 |
| K129A + R156Y | 51 |
| K129A + Q137E + R156Y | 72 |
| K129A + R156Y + H164N | 63 |

TABLE 14

Sterile filtered enzyme samples stored for 16 hours at +47° C.

| Mutations | % Residual Activity |
| --- | --- |
| SEQ ID NO: 3 | <5 |
| Q68H + T92S + K118A + K129A + R156Y + G200P + N331F | 77 |
| Q68H + T92A + K118A + K129A + R156Y + G200P + N331F | 83 |
| Q68H + K118A + K129A + R156Y + G200P + N331F | 91 |
| Q68H + T92D + K118A + K129A + R156Y + G200P + N331F | 49 |
| Q68H + T92Y + K118A + K129A + R156Y + G200P + N331F | 78 |
| Q68H + T92I + K118A + K129A + R156Y + G200P + N331F | 89 |
| Q68H + T92V + K118A + K129A + R156Y + G200P + N331F | 95 |
| Q68H + T92S + K118A + K129A + R156Y + G200P + G274D + N331F | 67 |
| Q68H + T92N + D97N + K118A + K129A + R156Y + G200P + N331F | 81 |
| Q68H | 52 |
| K118A + K129A + R156Y | 52 |
| T92V + K118A + K129A + R156Y | 88 |

TABLE 14-continued

Sterile filtered enzyme samples stored for 16 hours at +47° C.

| Mutations | % Residual Activity |
| --- | --- |
| K129A + R156Y + G200P + G204T + R211K | 68 |
| S123T + K129A + R156Y | 65 |
| K129A + R156Y + G200P | 73 |
| K118A + K129A + R156Y + G200P + N331F | 90 |
| G78A + K118A + K129A + R156Y + G200P + N331F | 98 |
| T92V + K118A + K129A + R156Y + G200P + N331F | 95 |

TABLE 15

Sterile filtered enzyme samples stored for 16 hours at +44° C.

| Mutations | % Residual Activity |
| --- | --- |
| SEQ ID NO: 3 | 22 |
| R156Y | 59 |
| K13R | 34 |
| K307Q | 31 |
| K414A | 34 |
| G253A | 33 |
| G498S | 31 |
| M310V | 38 |
| N399I | 30 |
| V1* + V2* + H3* + G4* + Q5* | 31 |
| F146L | 34 |
| K445S | 30 |
| K470T | 30 |

TABLE 16

Sterile filtered enzyme samples stored for 16 hours at +45° C.

| Mutations | % Residual Activity |
| --- | --- |
| SEQ ID NO: 3 | 6 |
| R156Y | 34 |
| K129A + R156Y | 55 |
| K101R + L102I | 12 |
| K118A + K129A + R156Y | 72 |
| K129A + R156Y + P507A | 57 |
| K129A + R156Y + D366H + T374A | 44 |
| K129A + R156Y + V259I + R267K + L268K + S269A | 40 |
| K129A + R156Y + G200P + G204T + R211K | 49 |
| K129A + R156Y + V159M + H164N + F165Y | 30 |
| T104A + P111Q + A117S + K129A + R156Y | 39 |
| S123T + K129A + R156Y | 70 |
| K129A + R156Y + D324N | 60 |
| K129A + R156Y + D461N | 59 |
| K129A + R156Y + D461T | 61 |
| K129A + R156Y + D461Q | 59 |
| D37G + K129A + R156Y | 60 |
| D37N + K129A + R156Y | 64 |
| K129A + R156Y + R267H | 64 |
| K129A + R156Y + D303I | 62 |
| K129A + R156Y + D303K | 65 |
| K129A + R156Y + K275T | 68 |
| K129A + R156Y + G200P | 92 |
| K118A + K129A + R156Y + K470T | 80 |
| H164N | <5 |
| K129A + R156Y + N302K + D303S | 66 |
| K129A + R156Y + N302K + D303L | 64 |

TABLE 17

Sterile filtered enzyme samples stored for 16 hours at +44° C.

| Mutations | % Residual Activity |
|---|---|
| SEQ ID NO: 3 | 26 |
| R156Y | 58 |
| K118A + R156Y + G200P | 84 |
| K118A + K129A + Q137E + R156Y + G200P + N331F | 92 |
| K445C + K470C | 32 |
| F281L | 32 |
| D366H | 35 |
| K392G | 26 |
| D395G | 35 |
| S76W | 47 |
| G498D | 32 |
| G498A | 36 |
| D324N | 39 |
| S123T | 36 |
| Q68Y | 6 |
| Q68C | 13 |
| K129A + R156Y | 89 |
| K118A + K129A + R156Y + G200P + N331F | 100 |

TABLE 18

Sterile filtered enzyme samples stored for 16 hours at +44° C.

| Mutations | % Residual Activity |
|---|---|
| SEQ ID NO: 3 | 34 |
| R156Y | 66 |
| R156M | 39 |
| R156F | 63 |
| R156W | 44 |
| R156L | 34 |
| R156P | <5 |
| R156V | 50 |
| R156T | 35 |
| R156S | 27 |
| R156A | 36 |
| R156D | 34 |
| R156K | 52 |
| R156N | 29 |
| R156I | 50 |
| T92I | 39 |
| R156Q | 34 |

TABLE 19

Sterile filtered enzyme samples stored for 16 hours at +44° C.

| Mutations | % Residual Activity |
|---|---|
| SEQ ID NO: 3 | 25 |
| R156Y | 70 |
| R156E | 66 |
| R156F | 65 |
| T92V | 43 |
| R156P | <5 |
| R156V | 53 |
| R156K | 38 |
| R156I | 31 |

TABLE 20

Sterile filtered enzyme samples stored for 16 hours at +44° C.

| Mutations | % Residual Activity |
|---|---|
| SEQ ID NO: 3 | 31 |
| R156Y | 65 |
| N415S | 34 |
| S443E | 33 |
| S443K | 32 |
| S443Q | 35 |
| K129T | 46 |
| K129A | 50 |
| G468Y | 32 |
| G237A | 34 |
| G237S | 34 |
| G237V | 25 |
| G468S | 32 |

TABLE 21

Sterile filtered enzyme samples stored for 16 hours at +44° C.

| Mutations | % Residual Activity |
|---|---|
| SEQ ID NO: 3 | 21 |
| R156Y | 45 |
| S332P | 41 |
| K129A + R156Y + K176S | 73 |
| K129A + R156Y + D303V | 77 |
| K129A + R156Y + D303S | 81 |
| R197L | 20 |
| R340N | 41 |
| R340T | 43 |
| H193S | 51 |
| H193D | 49 |
| H193T | 66 |
| L34F | 43 |
| Q137D | 24 |
| Q149E | 48 |
| T9D | 40 |
| A83E | 49 |
| S214E | 25 |
| K129A + R156Y | 98 |
| T92V | 49 |
| T92I | 36 |

TABLE 22

Sterile filtered enzyme samples stored for 16 hours at +47° C.

| Mutations | % Residual Activity |
|---|---|
| SEQ ID NO: 3 | <5 |
| R156Y | 29 |
| Q68H + R156V + G200P + N331F | 93 |
| Q68H + R156F + G200P + N331F | Approx. 100 |
| Q68H + G200P + N331F | Approx. 100 |
| Q68H + T92V + R156V + G200P + M3310V | 86 |
| Q68H + T92V + R156Y + G200P + M310V | 86 |
| Q68H + T92V + R156F + G200P + M310V | 91 |
| Q68H + T92V + R156F + G200P + M310V + S484C | 82 |
| Q68H + T92V + G200P + M310V | 82 |
| Q68H + T92V + R156V + G200P + M310V + N331F | Approx. 100 |
| Q68H + T92V + R156Y + G200P + M310V + N331F | Approx. 100 |
| Q68H + T92V + R156F + G200P + M310V + N331F | 86 |
| Q68H + T92V + G200P + M310V + N331F | 80 |
| D366H | <5 |
| K118A + K129A + R156Y + G200P + N331F | 81 |
| Q68H + K118A + K129A + R156Y + G200P + N331F | 87 |

TABLE 22-continued

Sterile filtered enzyme samples stored for 16 hours at +47° C.

| Mutations | % Residual Activity |
|---|---|
| Q68H T92V K118A K129A R156Y G200P N331F | 80 |
| M40L + A41T + Q67M + N72S + S76D + G78A + Q82K + Q137E + N153K + H164N + D249N + V272A + I337L + M356L + V397A + N415S + T421I + S424N + N441D + V450I + E489A + A490V + T517A + S522* | 41 |
| I10V + F17S + D33E + M40L + Q67M + N72S + S76D + G78A + Q82K + T92A + L102Q + Q137E + I222V + V228I + D249N + V272A + I337L + M356L + T374A + V397A + S416A + T421I + S424N + N441D + D444Y + V450I + A469E + K470T + I473G + T517A + S522P + P523V + V524E | 52 |
| Q32H + M40L + R49G + D65E + Q67M + N72S + S76D + G78A + Q82K + 92A + L102Q + T104A + Q137E + H164N + K202E + I222V + V228I + D249N + M356L + T374A | 41 |
| I10V + F17S + Y53H + Q67M + N72S + S76D + G78A + Q82K + T92A + L102Q + Q137E + T172V + A177T + I222V + V228I + D249N + S269N + I337L + M356LV397A + S416A + T421I + S424H + N441D + D444Y + A469E + K470T + I473G + T517A + S522* | 26 |

TABLE 23

Sterile filtered enzyme samples stored for 64 hours at +46° C.

| Mutations | % Residual Activity |
|---|---|
| SEQ ID NO: 3 | <5 |
| R156Y | <5 |
| Q68H + R156V + G200P + N331F | 80 |
| Q68H + R156F + G200P + N331F | 84 |
| Q68H + G200P + N331F | 63 |
| Q68H + T92V + R156V + G200P + M310V | 52 |
| Q68H + T92V + R156Y + G200P + M310V | 67 |
| Q68H + T92V + R156F + G200P + M310V | 63 |
| Q68H + T92V + R156F + G200P + M310V + S484C | 68 |
| Q68H + T92V + G200P + M310V | 48 |
| Q68H + T92V + R156V + G200P + M310V + N331F | 93 |
| Q68H + T92V + R156Y + G200P + M310V + N331F | 100 |
| Q68H + T92V + R156F + G200P + M310V + N331F | 91 |
| Q68H + T92V + G200P + M310V + N331F | 80 |
| K118A + K129A + R156Y + G200P + N331F | 56 |
| Q68H + K118A + K129A + R156Y + G200P + N331F | 86 |
| Q68H + T92V + K118A + K129A + R156Y + G200P + N331F | 88 |

TABLE 24

Sterile filtered enzyme samples stored for 16 hours at +44° C.

| Mutations | % Residual Activity |
|---|---|
| SEQ ID NO: 3 | 16 |
| R156Y | 52 |
| T374A | 27 |
| F146L + K322I | 24 |
| K129A + Q137E + R156Y + G200P | 87 |
| Q68S | 14 |
| Q68T | <5 |
| K129A + R156Y | 71 |

TABLE 24-continued

Sterile filtered enzyme samples stored for 16 hours at +44° C.

| Mutations | % Residual Activity |
|---|---|
| F146L | 26 |
| K129A + R156Y + G200P | 82 |
| Q68H | 77 |

TABLE 25

Sterile filtered enzyme samples stored for 16 hours at +44° C.

| Mutations | % Residual Activity |
|---|---|
| SEQ ID NO: 3 | 19 |
| R156Y | 53 |
| K101A + K129A | 47 |
| K129A + K470T | 46 |
| S332P | 29 |
| G413A | 30 |
| K118A + K129A + R156Y + A224P | 81 |
| K129A + K176P | 50 |
| K118A + K129A + R156Y + K169A + G200P + N331F | 89 |
| K118A + K129A + R156Y + G200P + M310V + N331F | 86 |
| K129A + R156Y + K454Q | 86 |
| K13A + K129A | 49 |
| G78A + T92V + K118A + K129A + R156Y + K169A | 93 |
| K129A + R156Y + K322I + K454Q | 76 |
| K129A | 47 |
| K129A + R156Y | 74 |
| K118A + K129A + R156Y | 77 |
| K118A + K129A + R156Y + G200P + N331F | Approx. 100 |
| G78A + T92V + K118A + K129A + R156Y | 93 |

TABLE 26

Sterile filtered enzyme samples stored for 6 days at +46° C.

| Mutations | % Residual Activity |
|---|---|
| SEQ ID NO: 3 | <5 |
| R156Y | <5 |
| Q68H + R156V + G200P + N331F | 50 |
| Q68H + R156Y + G200P + N331F | 60 |
| Q68H + R156F + G200P + N331F | 64 |
| Q68H + G200P + N331F | 40 |
| Q68H + T92V + R156V + G200P + M310V | 32 |
| Q68H + T92V + R156Y + G200P + M310V | 42 |
| Q68H + T92V + R156F + G200P + M310V | 43 |
| Q68H + T92V + R156F + G200P + M310V + S484C | 34 |
| Q68H + T92V + G200P + M310V | 27 |
| Q68H + T92V + R156F + G200P + M310V + N331F | 93 |
| Q68H + T92V + G200P + M310V + N331F | 58 |
| K118A + K129A + R156Y + G200P + N331F | 27 |
| Q68H + K118A + K129A + R156Y + G200P + N331F | 75 |
| Q68H + T92V + K118A + K129A + R156Y + G200P + N331F | 70 |

TABLE 27

Sterile filtered enzyme samples stored for 64 hours at +44° C.

| Mutations | % Residual Activity |
|---|---|
| SEQ ID NO: 3 | <5 |
| R156Y | 9 |
| K101A + K129A | 6 |
| K129A + K470T | 4 |
| S332P | <5 |

TABLE 27-continued

Sterile filtered enzyme samples stored for 64 hours at +44° C.

| Mutations | % Residual Activity |
|---|---|
| G413A | <5 |
| K118A + K129A + R156Y + A224P | 51 |
| K129A + K176P | 6 |
| K118A + K129A + R156Y + K169A + G200P + N331F | 67 |
| K118A + K129A + R156Y + G200P + M310V + N331F | 63 |
| K129A + R156Y + K454Q | 52 |
| K13A + K129A | 5 |
| G78A + T92V + K118A + K129A + R156Y + K169A | 72 |
| K129A | 5 |
| K129A + R156Y | 32 |
| K118A + K129A + R156Y | 30 |
| K118A + K129A + R156Y + G200P + N331F | 63 |
| G78A + T92V + K118A + K129A + R156Y | 72 |

TABLE 28

Sterile filtered enzyme samples stored for 64 hours at +46° C.

| Mutations | % Residual Activity |
|---|---|
| SEQ ID NO: 3 | <5 |
| R156Y | 4 |
| G78A + T92V + K118A + K129A + R156Y + G200P + N331F | 71 |
| K118A + K129A + R156Y + G200P + N331F + N399I | 59 |
| K118A + K129A + F146L + R156Y + G200P + N331F | 62 |
| T92V + K118A + K129A + Q137E + R156Y + G200P + N331F | 74 |
| T92V + K118A + K129A + R156Y + H164N + G200P + N331F | 70 |
| Q68H + T92V + K118A + K129A + Q137E + R156Y + G200P + N331F | 87 |
| Q68H + T92V + K118A + S123T + K129A + Q137E + R156Y + G200P + N331F | 90 |
| T92V + K118A + K129A + R156Y + G200P + N331F | 66 |
| K118A + K129A + R156Y + G200P + N331F | 68 |
| Q68H T92V K118A K129A R156Y G200P N331F | 83 |

TABLE 29

Sterile filtered enzyme samples stored for 16 hours at +44° C.

| Mutations | % Residual Activity |
|---|---|
| SEQ ID NO: 3 | 19 |
| R156Y | 51 |
| S123P | 69 |
| V159M | 21 |
| V345I | 34 |
| G225S | 30 |
| V232A | <10 |

TABLE 30

Sterile filtered enzyme samples stored for 10 days at +46° C.

| Mutations | % Residual Activity |
|---|---|
| SEQ ID NO: 3 | <5 |
| R156Y | <5 |
| G78A + T92V + K118A + K129A + R156Y + G200P + N331F | 32 |
| K118A + K129A + R156Y + G200P + N331F + N399I | 16 |
| K118A + K129A + F146L + R156Y + G200P + N331F | 23 |

TABLE 30-continued

Sterile filtered enzyme samples stored for 10 days at +46° C.

| Mutations | % Residual Activity |
|---|---|
| T92V + K118A + K129A + Q137E + R156Y + G200P + N331F | 34 |
| T92V + K118A + K129A + R156Y + H164N + G200P + N331F | 31 |
| Q68H + T92V + K118A + K129A + Q137E + R156Y + G200P + N331F | 67 |
| Q68H + T92V + K118A + S123T + K129A + Q137E + R156Y + G200P + N331F | 81 |
| T92V + K118A + K129A + R156Y + G200P + N331F | 23 |
| K118A + K129A + R156Y + G200P + N331F | 25 |
| Q68H T92V K118A K129A R156Y G200P N331F | 61 |

TABLE 31

Sterile filtered enzyme samples stored for 16 hours at +44° C.

| Mutations | % Residual Activity |
|---|---|
| SEQ ID NO: 3 | 15 |
| R156Y | 51 |
| Q68F | <5 |
| Q68N | 69 |
| Q68Y | <5 |
| Q68D | <10 |
| Q68C | <10 |
| Q68G | <10 |
| Q68S | <10 |
| Q68E | <5 |
| Q68A | <5 |
| Q68M | 27 |
| Q68W | <10 |
| Q68H | 82 |

TABLE 32

Sterile filtered enzyme samples stored for 7 days at +46° C.

| Mutations | % Residual Activity |
|---|---|
| SEQ ID NO: 3 | <5 |
| R156Y | <5 |
| Q68H + T92V + K118A + K129A + Q137E + R156Y + G200P + A224P + N331F | 81 |
| Q68H + T92V + K118A + Q137E + R156Y + G200P + N331F | 74 |
| Q68H + T92V + Q137E + R156Y + G200P + N331F | 80 |
| Q68H + T92V + K118A + Q137E + G200P + N331F | 65 |
| Q68H + T92V + K118A + Q137E + R156Y + N331F | 80 |
| Q68H + T92V + K118A + Q137E + R156Y + G200P | 67 |
| G78A + K118A + K129A + R156Y + K169A | 14 |
| Q68H + T92V + K118A + K129A + Q137E + R156Y + G200P + N331F | 73 |
| K129A + R156Y | <5 |
| G78A + K118A + K129A + R156Y | 7 |

TABLE 33

Sterile filtered enzyme samples stored for 48 hours at +46° C.

| Mutations | % Residual Activity |
|---|---|
| SEQ ID NO: 3 | <5 |
| R156Y | 9 |
| K118A + K129A + R156Y + G200P + N331F | 67 |
| Q68H + K118A + K129A + R156Y + G200P + N331F | 79 |

TABLE 33-continued

Sterile filtered enzyme samples stored for 48 hours at +46° C.

| Mutations | % Residual Activity |
| --- | --- |
| Q68H + T92V + K118A + K129A + R156Y + G200P + N331F | 85 |
| Q68H + T92V + K118A + K129A + R156Y + H193T + D366H | 73 |
| Q68H + T92V + K118A + K129A + Q137E + R156Y + H193T + D366H | 72 |
| Q68H + T92V + R156Y + H193T + D366H | 78 |
| Q68H + T92V + R156F + H193T + D366H | 78 |
| Q68H + R156Y + H193T + D366H | 68 |
| Q68H + T92V + K118A + K129A + R156Y + H193T | 67 |
| Q68H + T92V + K118A + K129A + Q137E + R156Y + H193T | 80 |
| Q68H + T92V + R156Y + H193T | 84 |
| Q68H + T92V + R156F + H193T | 66 |
| Q68H + R156Y + H193T | 66 |
| Q68H + R156Y + H193T + G200P + M310V | 93 |
| Q68H + T92V + R156F + H193T + G200P + M310V | 82 |
| Q68H + T92V + K118A + K129A + Q137E + R156Y + H193T + G200P + M310V + E446K | 76 |
| Q68H + T92V + R156Y + H193T + G200P + M310V | 73 |
| Q68H + T92V + K118A + K129A + R156Y + H193T + G200P + M310V | 89 |
| Q68H + K129T + R156K + G200P + N331F | 95 |
| Q68H + K129A + R156K + G200P + N331F | 86 |
| Q68H + K118A + R156V + G200P + N331F | 81 |
| Q68H + K118S + R156F + G200P + G274D + N331F | 68 |

TABLE 34

Sterile filtered enzyme samples stored for 16 hours at +44° C.

| Mutations | % Residual Activity |
| --- | --- |
| SEQ ID NO: 3 | 22 |
| R156Y | 61 |
| S123T + K129A + R156Y | 83 |
| H193T | 44 |
| G78A + T92V + K118A + K129A + R156Y | 91 |
| S123T | 55 |
| S123P | 73 |
| V232A | <10 |
| K129A + R156Y | 64 |
| K118A + K129A + R156Y | 68 |

TABLE 35

Sterile filtered enzyme samples stored for 16 hours at +44° C.

| Mutations | % Residual Activity |
| --- | --- |
| SEQ ID NO: 3 | 17 |
| R156Y | 60 |
| N140F | 25 |
| H164A | 7 |
| H193A | 23 |
| R500T | 30 |
| R500A | 33 |
| R500V | 29 |
| H199A | <10 |
| H3A | 26 |
| H436A | 26 |
| H448A | <10 |
| H512A | 25 |
| H96A | 14 |
| H3A + H436A | 27 |

TABLE 36

Sterile filtered enzyme samples stored for 16 hours at +44° C.

| Mutations | % Residual Activity |
| --- | --- |
| SEQ ID NO: 3 | 27 |
| R156Y | 66 |
| N399I | 33 |
| L34F | 35 |
| Q149E | 35 |
| S332P | 36 |
| K129A | 50 |
| K21Q + K129A | 54 |
| K129A + K275Q | 56 |
| Q68F | 6 |
| T9D + L34F + A83E + Q149E + H193T + S332P + R340T | 53 |

TABLE 37

Sterile filtered enzyme samples stored for 12 days at +37° C.

| Mutations | % Residual Activity |
| --- | --- |
| SEQ ID NO: 3 | <5 |
| R156Y | 8 |
| K118A + K129A + R156Y + G200P + N331F | 52 |
| Q68H + K118A + K129A + R156Y + G200P + N331F | 47 |
| Q68H + T92V + K118A + K129A + R156Y + G200P + N331F | 67 |
| Q68H + R156Y + G200P + N331F | 47 |
| Q68H + R156F + G200P + N331F | 66 |
| Q68H + T92V + R156Y + G200P + M310V | 41 |
| Q68H + T92V + K118A + K129A + R156Y + H193T + D366H | 54 |
| Q68H + T92V + K118A + K129A + Q137E + R156Y + H193T + D366H | 44 |
| Q68H + T92V + R156Y + H193T + D366H | 44 |
| Q68H + T92V + R156F + H193T + D366H | 37 |
| Q68H + R156Y + H193T + D366H | 36 |
| Q68H + T92V + K118A + K129A + R156Y + H193T | 50 |
| Q68H + T92V + K118A + K129A + Q137E + R156Y + H193T | 56 |
| Q68H + T92V + R156Y + H193T | 37 |
| Q68H + T92V + R156F + H193T | 37 |
| Q68H + R156Y + H193T | 44 |
| Q68H + R156Y + H193T + G200P + M310V | 34 |
| Q68H + T92V + R156F + H193T + G200P + M310V | 28 |
| Q68H + T92V + K118A + K129A + Q137E + R156Y + H193T + G200P + M310V + E446K | 47 |
| Q68H + T92V + R156Y + H193T + G200P + M310V | 47 |
| Q68H + T92V + K118A + K129A + R156Y + H193T + G200P + M310V | 56 |

TABLE 38

Sterile filtered enzyme samples stored for 16 hours at +44° C.

| Mutations | % Residual Activity |
| --- | --- |
| SEQ ID NO: 3 | 19 |
| R156Y | 49 |
| G200S | 28 |
| G200D | 25 |
| G200Y | 12 |
| G200L | <5 |
| G200P | 37 |
| G200W | <5 |
| G200I | <5 |
| G200N | 9 |
| G200F | <5 |
| G200V | 9 |

TABLE 38-continued

Sterile filtered enzyme samples stored for 16 hours at +44° C.

| Mutations | % Residual Activity |
|---|---|
| G200H | 12 |
| G200Q | 19 |
| G200C | 17 |
| G200A | 24 |
| G200M | 6 |
| G200K | 11 |
| G200E | 48 |
| G200R | <5 |
| G200T | 5 |

TABLE 39

Sterile filtered enzyme samples stored for 16 hours at +44° C.

| Mutations | % Residual Activity |
|---|---|
| SEQ ID NO: 3 | 13 |
| R156Y | 45 |
| K21Q + K129A | 34 |
| K129A + K275Q | 39 |
| T9D + L34F + A83E + Q149E + H193T + S332P + R340T | 43 |
| N399I | 24 |
| L34F | 22 |
| Q149E | 23 |
| S332P | 24 |
| K129A | 58 |
| G518D | 19 |
| K118A + K129A | 73 |
| K118A | 48 |
| K129A + K169A | 40 |

TABLE 40

Purified enzyme samples stored for 5 days at +46° C.

| Mutations | % Residual Activity |
|---|---|
| SEQ ID NO: 3 | <5 |
| R156Y | <5 |
| Q68H + T92V + K118A + K129A + Q137E + R156Y + H193T + D366H | 73 |
| Q68H + R156Y + H193T | 63 |
| Q68H | 13 |
| Q68H + T92V + K118A + Q137E + R156Y + N331F | 70 |
| G78A + T92V + K118A + K129A + R156Y | 44 |
| K118A + K129A + R156Y + G200P + N331F | 46 |
| Q68H + T92V + K118A + K129A + R156Y + G200P + N331F | 83 |
| Q68H + K129T + R156K + G200P + N331F | 77 |
| Q68H + T92V + K118A + K129A + R156Y + H193T + D366H | 85 |

TABLE 41

Sterile filtered enzyme samples stored for 5 days at +46° C.

| Mutations | % Residual Activity |
|---|---|
| SEQ ID NO: 3 | <5 |
| R156Y | <5 |
| Q68H + T92V + K118A + K129A + Q137E + R156Y + H193T + N331K | 70 |
| Q68H + T92V + K118A + K129A + Q137E + R156Y + H193T + N331H | 42 |

TABLE 41-continued

Sterile filtered enzyme samples stored for 5 days at +46° C.

| Mutations | % Residual Activity |
|---|---|
| Q68H + T92V + K118A + K129A + Q137E + R156Y + H193T + N331Q | 24 |
| Q68H + T92V + K118A + K129A + Q137E + R156Y + H193T | 33 |
| Q68H + K118A + Q137E + R156Y + G200P + N331F | 74 |
| Q68H + S76W + T92V + K118A + Q137E + R156Y + G200P + N331F | 87 |
| K13A + Q68H + T92V + K118A + Q137E + R156Y + G200P | 54 |
| Q68H + T92V + K118A + Q137E + R156Y + G200P + D324N | 53 |
| Q68H + T92V + K118A + Q137E + R156Y + G200P + K470T | 69 |
| Q68H + T92V + K118A + Q137E + R156Y + G200P + N331F | 75 |
| Q68H + T92V + K118A + Q137E + R156Y + G200P | 52 |

TABLE 42

Sterile filtered enzyme samples stored for 16 hours at +44° C.

| Mutations | % Residual Activity |
|---|---|
| SEQ ID NO: 3 | 13 |
| R156Y | 43 |
| S76M | 21 |
| S76I | 36 |
| S76E | 19 |
| S76R | 26 |
| S76K | 27 |
| S76V | 39 |
| S76R | 24 |

TABLE 43

Sterile filtered enzyme samples stored for 16 hours at +44° C.

| Mutations | % Residual Activity |
|---|---|
| SEQ ID NO: 3 | 20 |
| R156Y | 51 |
| K118A + R156Y | 62 |
| R197A | <5 |
| R20A | 26 |
| R267A | 26 |
| R295A | 23 |
| R314A | <10 |
| R340A | 23 |
| A221K | 25 |
| M290R | 23 |
| M373Q | 25 |
| V397S | 25 |
| T417K | 27 |
| N441G + A442E + S443D | 30 |
| S467R + G468S + A469T | 29 |
| I473T | 24 |
| A490R | 32 |
| T517A + G518D | 31 |
| V431E | 29 |
| S76W + G200P + A224P | 58 |
| S76W + G200P | 59 |
| G200P + A224P | 56 |
| S76T | 42 |
| M310V | 31 |
| G200P | 47 |
| G200E | 59 |
| M310V + N399I | <10 |
| Q68W | <5 |

TABLE 44

Sterile filtered enzyme samples stored for 16 hours at +46° C.

| Mutations | % Residual Activity |
|---|---|
| SEQ ID NO: 3 | 8 |
| R156Y | 40 |
| Q68H + T92V + K118A + Q137E + N140F + R156Y + G200P + K470T | 89 |
| Q68H + T92V + K118A + S123P + K129A + Q137E + R156Y + G200P + N331F | 88 |
| T92V + K118A + Q137E + R156Y + G200P + N331F | 88 |
| S76W + G200P + A224P | 44 |
| S76W + G200P | 45 |
| G200P + A224P | 48 |
| S76T | 26 |
| Q68H + T92V + K118A + Q137E + R156Y + G200P + M310L | 91 |
| Q68H + T92V + K118A + K129A + Q137E + R156Y + G200P + N331F | 95 |
| G200P | 39 |

TABLE 45

Sterile filtered enzyme samples stored for 9 days at +46° C.

| Mutations | % Residual Activity |
|---|---|
| SEQ ID NO: 3 | <5 |
| R156Y | <5 |
| Q68H + T92V + K118A + K129A + Q137E + R156Y + H193T + N331K | 46 |
| Q68H + T92V + K118A + K129A + Q137E + R156Y + H193T + N331H | 19 |
| Q68H + T92V + K118A + K129A + Q137E + R156Y + H193T + N331Q | 9 |
| Q68H + T92V + K118A + K129A + Q137E + R156Y + H193T | 17 |
| Q68H + K118A + Q137E + R156Y + G200P + N331F | 48 |
| Q68H + S76W + T92V + K118A + Q137E + R156Y + G200P + N331F | 65 |
| K13A + Q68H + T92V + K118A + Q137E + R156Y + G200P | 31 |
| 68H + T92V + K118A + Q137E + R156Y + G200P + D324N | 30 |
| Q68H + T92V + K118A + Q137E + R156Y + G200P + K470T | 41 |
| Q68H + T92V + K118A + Q137E + R156Y + G200P + N331F | 50 |
| Q68H + T92V + K118A + Q137E + R156Y + G200P | 30 |

TABLE 46

Purified enzyme samples stored for 9 days at +46° C.

| Mutations | % Residual Activity |
|---|---|
| SEQ ID NO: 3 | <5 |
| R156Y | <5 |
| Q68H + T92V + K118A + K129A + Q137E + R156Y + H193T + D366H | 52 |
| Q68H + R156Y + H193T | 34 |
| Q68H + T92V + K118A + Q137E + R156Y + N331F | 45 |
| G78A + T92V + K118A + K129A + R156Y | 14 |
| K118A + K129A + R156Y + G200P + N331F | 18 |
| Q68H + T92V + K118A + K129A + R156Y + G200P + N331F | 56 |
| Q68H + K129T + R156K + G200P + N331F | 47 |
| Q68H + T92V + K118A + K129A + R156Y + H193T + D366H | 52 |
| Q68H + R156Y + H193T | 31 |

TABLE 47

Sterile filtered enzyme samples stored for 30 days at +37° C.

| Mutations | % Residual Activity |
|---|---|
| SEQ ID NO: 3 | <5 |
| R156Y | <5 |
| K118A + K129A + R156Y + G200P + N331F | 33 |
| Q68H + K118A + K129A + R156Y + G200P + N331F | 42 |
| Q68H + T92V + K118A + K129A + R156Y + G200P + N331F | 52 |
| Q68H + R156Y + G200P + N331F | 41 |
| Q68H + R156F + G200P + N331F | 58 |
| Q68H + T92V + R156Y + G200P + M310V | 41 |
| Q68H + T92V + R156F + G200P + M310V | 42 |
| Q68H + T92V + K118A + K129A + R156Y + H193T + D366H | 50 |
| Q68H + T92V + K118A + K129A + Q137E + R156Y + H193T + D366H | 32 |
| Q68H + T92V + R156Y + H193T + D366H | 33 |
| Q68H + T92V + R156F + H193T + D366H | 28 |
| Q68H + R156Y + H193T + D366H | 25 |
| Q68H + T92V + K118A + K129A + R156Y + H193T | 41 |
| Q68H + T92V + K118A + K129A + Q137E + R156Y + H193T | 43 |
| Q68H + T92V + R156Y + H193T | 27 |
| Q68H + T92V + R156F + H193T | 23 |
| Q68H + R156Y + H193T | 33 |
| Q68H + R156Y + H193T + G200P + M310V | 28 |
| Q68H + T92V + R156F + H193T + G200P + M310V | 21 |
| Q68H + T92V + K118A + K129A + Q137E + R156Y + H193T + G200P + M310V + E446K | 35 |
| Q68H + T92V + R156Y + H193T + G200P + M310V | 35 |
| Q68H + T92V + K118A + K129A + R156Y + H193T + G200P + M310V | 46 |

TABLE 48

Sterile filtered enzyme samples stored for 16 hours at +44° C.

| Mutations | % Residual Activity |
|---|---|
| SEQ ID NO: 3 | 15 |
| R156Y | 49 |
| A83S | 15 |
| A83N | 9 |
| A83Y | 10 |
| A83H | 14 |
| A83I | 8 |
| A83L | 10 |
| A83R | 16 |
| A83D | 17 |
| A83T | 12 |
| A83E | 31 |
| L34V | 22 |
| L34M | 19 |
| L34I | 24 |
| M310I | 21 |
| M310V | 20 |
| M310L | 18 |

TABLE 49

Sterile filtered enzyme samples stored for 3 days at +35° C.

| Mutations | % Residual Activity |
|---|---|
| SEQ ID NO: 3 | 61 |
| R156Y | 89 |
| N331K | 57 |
| N331R | 54 |
| N331L | 39 |
| N331H | 62 |
| N331G | 59 |
| N331M | 70 |
| N331W | 55 |
| N331S | 58 |
| N331V | 57 |
| N331T | 46 |
| N331Y | 55 |
| N331I | 47 |
| N331A | 87 |
| N331Q | 82 |
| N331C | 70 |
| N331E | 58 |
| N331D | 63 |
| N331P | 26 |
| N331F | 51 |

TABLE 51

Sterile filtered enzyme samples stored for 2 days at +44° C.

| Mutations | % Residual Activity |
|---|---|
| SEQ ID NO: 3 | <5 |
| R156Y | 20 |
| Q68H + R156Y | 61 |
| Q68H + T92V + K118A + R156Y | 66 |
| Q68H + T92V + R156Y | 68 |
| Q68H + K118A + R156Y + H193T + D366H | 74 |
| Q68H + T92V + K118R + R156Y + H193T + D366H | 65 |
| Q68H + T92V + K118R + R156F | 63 |
| Q68H + K118R + R156Y | 68 |
| Q68H + T92V + R156Y + H193T + D366H | 69 |
| Q68H + K118R + R156Y + G200P | 74 |
| Q68H + K118R + R156F | 66 |
| K118A + K129A + R156Y + G200P + N331F | 79 |
| Q68H + T92V + K118A + K129A + R156Y + G200P + N331F | 91 |
| Q68H | 55 |
| D33V + Q68H + N168H + V450I | 70 |
| S123T | 10 |
| K129A | 10 |

TABLE 50

Sterile filtered enzyme samples stored for 16 hours at +44° C.

| Mutations | % Residual Activity |
|---|---|
| SEQ ID NO: 3 | 20 |
| R156Y | 58 |
| I10V + F17S + Q67M + N72S + S76D + G78A + Q82K + T104A + Q137E + N153K + R156Q + V219A + I222V + V228I + D249N + S269N + V272A + E333A + I337L + M356L + V397A + N415S + D420G + T421I + S424H + N441D + D444Y + V450I + A469E + K470T + I473G + T517A + S522* | 72 |
| I10V + D33E + M40L + A41T + Q67M + Y73F + S76D + G78A + Q82K + T92A + L102Q + Q137E + I222V + V228I + D249N + S269N + V272A + E333A + I337L + M356L + T374A + S416A + D444Y + A469E + K470T + I473G + T517A + S522* | 71 |
| I10V + F17S + D33E + M40L + Q67M + N72S + S76D + G78A + Q82K + T92A + L102Q + Q137E + H164N + N168K + T172A + V219A + I222V + V228I + D249N + S269N + V272A + E333A + I337L + M356L + N415S + T421I + S424H + N441D + D444Y + S522P + P523V + V524E | 78 |
| I10V + F17S + D33E + Q67M + N72S + S76D + G78A + Q82K + T92A + L102Q + Q137E + N168K + T172A + I222V + V228I + D249N + V272A + E333A + I337L + M356L + V397A + S416A + T421I + S424H + N441D + D444Y + A469E + K470T + I473S + V477I + E489A + A490V + T517A + S522* | 74 |
| I10V + F17S + M40L + Q67M + N72S + S76D + G78A + Q82K + T92A + L102Q + Q137E + I222V + V228I + D249N + S269N + V272A + T320A + I337L + M356L + T374A + V397A + N415S + T421I + S424H + N441D + D444Y + A469E + K470T + I473S + V477I + T517A + S522P + P523V + V524E | 73 |
| I10V + F17S + D33E + M40L + A41T + Q67M + N72S + S76D + G78A + Q82K + Q137E + V219A + D249N + V272A + I337L + M356L + V397A + S416A + T421I + S424N + N441D + D444Y + V450I + K470T + I473S + V477I | 64 |
| I10V + F17S + Q67M + N72S + S76D + G78A + Q82K + T92A + T104A + Q137E + R156Q + V159A + H164N + N168K + T172A + I222V + V228I + D249N + V272A | 66 |
| K118A + K129A + R156Y + G200P + N331F | 98 |
| Q68H + T92V + K118A + K129A + R156Y + G200P + N331F | Approx 100 |

Liquid Laundry Detergent Compositions

Compositions 1-8: Liquid laundry detergent compositions suitable for front-loading automatic washing machines.

| Ingredient | Composition (wt % of composition) | | | | | | | |
|---|---|---|---|---|---|---|---|---|
| | 1 | 2 | 3 | 4 | 5 | 6 | 7 | 8 |
| Alkylbenzene sulfonic acid | 7 | 11 | 4.5 | 1.2 | 1.5 | 16.3 | 5.2 | 4 |
| Sodium $C_{12-44}$ alkyl ethoxy 3 sulfate | 2.3 | 3.5 | 4.5 | 4.5 | 7 | 15 | 1.8 | 2 |
| $C_{14-15}$ alkyl 8-ethoxylate | 5 | 8 | 2.5 | 2.6 | 4.5 | 4 | 3.7 | 2 |
| $C_{12}$ alkyl dimethyl amine oxide | — | — | 0.2 | — | — | — | — | — |
| $C_{12-14}$ alkyl hydroxyethyl dimethyl ammonium chloride | — | — | — | 0.5 | — | — | — | — |
| $C_{12-18}$ Fatty acid | 2.6 | 4 | 4 | 2.6 | 2.8 | 7.2 | 2.6 | 1.5 |
| Citric acid | 2.6 | 3 | 1.5 | 2 | 2.5 | 4.1 | 2.6 | 2 |
| Protease (Purafect ® Prime) | 0.5 | 0.7 | 0.6 | 0.3 | 0.5 | 2 | 0.5 | 0.6 |
| Amylase (Natalase ®) | 0.1 | 0.2 | 0.15 | — | 0.05 | 0.5 | 0.1 | 0.2 |
| Mannanase (Mannaway ®) | 0.05 | 0.1 | 0.05 | — | — | 0.1 | 0.04 | — |
| Xyloglucanase* (mg aep/100 g detergent) | 1 | 4 | 3 | 3 | 2 | 8 | 2.5 | 4 |
| Random graft co-polymer[1] | 1 | 0.2 | 1 | 0.4 | 0.5 | 0.3 | 0.3 | 1 |
| A compound having the following general structure: bis(($C_2H_5O$)($C_2H_4O$)$n$)($CH_3$)—$N^+$—$C_xH_{2x}$—$N^+$—($CH_3$)-bis(($C_2H_5O$)($C_2H_4O$)$n$), wherein n = from 20 to 30, and x = from 3 to 8, or sulphated or sulphonated variants thereof | 0.4 | 2 | 0.4 | 0.2 | 1.5 | 0.2 | 0.7 | 0.3 |
| Ethoxylated Hexamethylene Diamine dimethyl quat | — | — | — | 0.4 | — | — | — | — |
| Ethoxylated Polyethylenimine[2] | — | — | — | — | — | 3 | — | — |
| Amphiphilic alkoxylated grease cleaning polymer[3] | 0.1 | 0.2 | 0.1 | 0.2 | 0.3 | 0.3 | 0.2 | 0.3 |
| Diethoxylated poly (1,2 propylene terephthalate short block soil release polymer. | — | — | — | — | — | — | 0.3 | — |
| Diethylenetriaminepenta(methylenephosphonic) acid | 0.2 | 0.3 | — | — | 0.2 | — | 0.2 | 0.3 |
| Hydroxyethane diphosphonic acid | — | — | 0.45 | — | — | 1.6 | — | 0.1 |
| FWA | 0.1 | 0.2 | 0.1 | — | — | 0.2 | 0.05 | 0.1 |
| Solvents (1,2 propanediol, ethanol), stabilizers | 3 | 4 | 1.5 | 1.5 | 2 | 1.9 | 2 | 1.5 |
| Hydrogenated castor oil derivative structurant | 0.4 | 0.4 | 0.3 | 0.1 | 0.3 | — | 0.4 | 0.5 |
| Boric acid | 1.5 | 2.5 | 2 | 1.5 | 1.5 | 0.5 | 1.5 | 1.5 |
| Na formate | — | — | — | 1 | — | — | — | — |
| Reversible protease inhibitor[4] | — | — | 0.002 | — | — | — | — | — |
| Perfume | 0.5 | 0.7 | 0.5 | 0.5 | 0.8 | 1.7 | 0.5 | 0.8 |
| Perfume MicroCapsules slurry (30% am) | 0.2 | 0.3 | 0.7 | 0.2 | 0.05 | — | 0.9 | 0.7 |
| Ethoxylated thiophene Hueing Dye | | | | | | | 0.007 | 0.008 |
| Buffers (sodium hydroxide, Monoethanolamine) | To pH 8.2 | | | | | | | |
| Water and minors (antifoam, aesthetics) | To 100% | | | | | | | |

Compositions 9-16: Liquid laundry detergent compositions suitable for top-loading automatic washing machines.

| Ingredient | Composition (wt % of composition) | | | |
|---|---|---|---|---|
| | 9 | 10 | 11 | 12 |
| $C_{12-15}$ Alkylethoxy(1.8)sulfate | 20.1 | 15.1 | 20.0 | 15.1 |
| $C_{11.8}$ Alkylbenzene sulfonate | 2.7 | 2.0 | 1.0 | 2.0 |
| $C_{16-17}$ Branched alkyl sulfate | 6.5 | 4.9 | | 4.9 |
| $C_{12-14}$ Alkyl-9-ethoxylate | 0.8 | 0.8 | 0.8 | 0.8 |
| $C_{12}$ dimethylamine oxide | | | 0.9 | |
| Citric acid | 3.8 | 3.8 | 3.8 | 3.8 |

-continued

| Ingredients | | | | |
|---|---|---|---|---|
| $C_{12-18}$ fatty acid | 2.0 | 1.5 | 2.0 | 1.5 |
| Protease (Purafect ® Prime) | 1.5 | 1.5 | 0.5 | 1.5 |
| Amylase (Natalase ®) | 0.3 | 0.3 | 0.3 | 0.3 |
| Amylase (Stainzyme ®) | | | | |
| Mannanase (Mannaway ®) | 0.1 | | | |
| Pectate Lyase (Pectawash ®) | 0.1 | | | |
| Xyloglucanase* (mg aep/100 g detergent) | 5 | 13 | 2 | 5 |
| Borax | 3.0 | 3.0 | | |
| Na & Ca formate | 0.2 | 0.2 | | 0.2 |
| A compound having the following general structure: bis(($C_2H_5O$)($C_2H_4O$)$n$)($CH_3$)—$N^+$—$C_xH_{2x}$—$N^+$—($CH_3$)-bis(($C_2H_5O$)($C_2H_4O$)$n$), wherein n = from 20 to 30, and x = from 3 to 8, or sulphated or sulphonated variants thereof | 1.6 | 1.6 | 3.0 | 1.6 |
| Random graft co-polymer[1] | 0.4 | 0.2 | 1.0 | 0.5 |
| Diethylene triamine pentaacetic acid | 0.4 | 0.4 | 0.4 | 0.4 |
| Tinopal AMS-GX | 0.2 | 0.2 | 0.2 | 0.2 |
| Tinopal CBS-X | | | | |
| Amphiphilic alkoxylated grease cleaning polymer[3] | 1.0 | 1.3 | 1.3 | 1.4 |
| Texcare 240N (Clariant) | | | | 1.0 |
| Ethanol | 2.6 | 2.6 | 2.6 | 2.6 |
| Propylene Glycol | 4.6 | 4.6 | 4.6 | 4.6 |
| Diethylene glycol | 3.0 | 3.0 | 3.0 | 3.0 |
| Polyethylene glycol | 0.2 | 0.2 | 0.2 | 0.2 |
| Monoethanolamine | 2.7 | 2.7 | 2.7 | 2.7 |
| Triethanolamine | | | | |
| NaOH | to pH 8.3 | to pH 8.3 | to pH 8.3 | to pH 8.3 |
| Suds suppressor | | | | |
| Dye | 0.01 | 0.01 | 0.01 | |
| Perfume | 0.5 | 0.5 | 0.5 | 0.5 |
| Perfume MicroCapsules slurry (30% am) | 0.2 | 0.5 | 0.2 | 0.3 |
| Ethoxylated thiophene Hueing Dye | | | | |
| Water | balance | balance | balance | balance |

| Ingredients | Composition (wt % of composition) | | | |
|---|---|---|---|---|
| | 13 | 14 | 15 | 16 |
| $C_{12-15}$ Alkylethoxy(1.8)sulfate | 13.7 | 16.7 | 10.0 | 9.9 |
| $C_{11.8}$ Alkylbenzene sulfonate | 5.5 | 5.6 | 3.0 | 3.9 |
| $C_{16-17}$ Branched alkyl sulfate | 3.0 | 9.0 | 2.0 | |
| $C_{12-14}$ Alkyl-9-ethoxylate | 8.0 | 1.5 | 0.3 | 11.5 |
| $C_{12}$ dimethylamine oxide | | | | |
| Citric acid | 3.5 | 3.5 | 2.0 | 2.1 |
| $C_{12-18}$ fatty acid | 4.5 | 2.3 | | 0.9 |
| Protease (Purafect ® Prime) | 1.0 | 1.8 | 0.5 | 0.5 |
| Amylase (Natalase ®) | 0.2 | 0.4 | | |
| Amylase (Stainzyme ®) | | | | 1.1 |
| Mannanase (Mannaway ®) | | 0.1 | | |
| Pectate Lyase (Pectawash ®) | | 0.2 | | |
| Xyloglucanase* (mg aep/100 g detergent) | 20 | 1 | 2 | 3 |
| Borax | 2.0 | 3.0 | 3.0 | 3.3 |
| Na & Ca formate | 0.2 | | 0.7 | |
| A compound having the following general structure: bis(($C_2H_5O$)($C_2H_4O$)$n$)($CH_3$)—$N^+$—$C_xH_{2x}$—$N^+$—($CH_3$)-bis(($C_2H_5O$)($C_2H_4O$)$n$), wherein n = from 20 to 30, and x = from 3 to 8, or sulphated or sulphonated variants thereof | 2.0 | 1.6 | 1.3 | 1.2 |
| Random graft co-polymer[1] | 0.6 | 1.0 | 0.8 | 1.0 |
| Diethylene triamine pentaacetic acid | 0.2 | 0.3 | 0.8 | |
| Tinopal AMS-GX | 0.2 | 0.3 | 0.1 | |
| Tinopal CBS-X | | 0.1 | | 0.2 |
| Amphiphilic alkoxylated grease cleaning polymer[3] | 1.0 | 1.1 | 1.0 | 1.0 |
| Texcare 240N (Clariant) | | | | |

| | | | | |
|---|---|---|---|---|
| Ethanol | 1.8 | 3.0 | 1.3 | |
| Propylene Glycol | 3.0 | 4.0 | 2.5 | |
| Diethylene glycol | 3.0 | 2.7 | 3.6 | |
| Polyethylene glycol | 0.1 | 0.3 | 0.1 | 1.4 |
| Monoethanolamine | 4.7 | 3.3 | 1.7 | 0.4 |
| Triethanolamine | | | | 0.9 |
| NaOH | to pH 8.3 | to pH 8.3 | to pH 8.3 | to pH 8.5 |
| Suds suppressor | | | | |
| Dye | 0.01 | 0.01 | 0.01 | 0.0 |
| Perfume | 0.7 | 0.7 | 0.8 | 0.6 |
| Perfume MicroCapsules slurry (30% am) | 0.1 | 0.3 | 0.9 | 1.0 |
| Ethoxylated thiophene Hueing Dye | 0.002 | 0.004 | | |
| Water | balance | balance | balance | balance |

Composition 17: liquid laundry detergent composition in the form of a pouch, being encapsulated by a film of polyvinyl alcohol.

| Ingredient | Composition 17 (wt % of composition) |
|---|---|
| Alkylbenzene sulfonic acid | 21.0 |
| $C_{14-15}$ alkyl 8-ethoxylate | 18.0 |
| $C_{12-18}$ Fatty acid | 15.0 |
| Protease (Purafect ® Prime) | 1.5 |
| Amylase (Natalase ®) | 0.2 |
| Mannanase (Mannaway ®) | 0.1 |
| Xyloglucanase* (mg aep/100 g detergent) | 7 |
| A compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, or sulphated or sulphonated variants thereof | 2.0 |
| Ethoxylated Polyethylenimine[2] | 0.8 |
| Hydroxyethane diphosphonic acid | 0.8 |
| FWA | 0.2 |
| Solvents (1,2 propanediol, ethanol), stabilizers | 15.0 |
| Hydrogenated castor oil derivative structurant | 0.1 |
| Perfume | 1.6 |
| Ethoxylated thiophene Hueing Dye | 0.004 |
| Buffers (sodium hydroxide, Monoethanolamine) | To pH 8.2 |
| Water and minors (antifoam, aesthetics) | To 100% |

Examples 18-29

The following are granular detergent compositions produced in accordance with the invention suitable for laundering fabrics.

| | 18 | 19 | 20 | 21 | 22 | 23 |
|---|---|---|---|---|---|---|
| Linear alkylbenzenesulfonate with aliphatic carbon chain length $C_{11}$—$C_{12}$ | 15 | 12 | 20 | 10 | 12 | 13 |
| Other surfactants | 1.6 | 1.2 | 1.9 | 3.2 | 0.5 | 1.2 |
| Phosphate builder(s) | 2 | 25 | 4 | 3 | 2 | — |
| Zeolite | | 1 | | 1 | 4 | 1 |
| Silicate | 4 | 5 | 2 | 3 | 3 | 5 |
| Sodium Carbonate | 9 | 20 | 10 | 17 | 5 | 23 |
| Polyacrylate (MW 4500) | 1 | 0.6 | 1 | 1 | 1.5 | 1 |
| Amphiphilic alkoxylated grease cleaning polymer[3] | 0.2 | — | 0.3 | 0.4 | — | 1.0 |
| Carboxymethyl cellulose (Finnfix BDA ex CPKelco) | 1 | — | 0.3 | — | 1.1 | — |
| Xyloglucanase* (mg aep/100 g detergent) | 1.5 | 2.4 | 1.7 | 0.9 | 5.3 | 2.3 |
| Other enzymes powders | 0.23 | 0.17 | 0.5 | 0.2 | 0.2 | 0.6 |
| Fluorescent Brightener(s) | 0.16 | 0.06 | 0.16 | 0.18 | 0.16 | 0.16 |
| Diethylenetriamine pentaacetic acid or Ethylene diamine tetraacetic acid | 0.6 | | 0.6 | 0.25 | 0.6 | 0.6 |
| $MgSO_4$ | 1 | 1 | 1 | 0.5 | 1 | 1 |
| Bleach(es) and Bleach activator(s) | 6.88 | | 6.12 | 2.09 | 1.17 | 4.66 |
| Sulfate/Moisture/perfume | Balance to 100% | | | | | |

| | 24 | 25 | 26 | 27 | 28 | 29 |
|---|---|---|---|---|---|---|
| Linear alkylbenzenesulfonate with aliphatic carbon chain length $C_{11}$—$C_{12}$ | 8 | 7.1 | 7 | 6.5 | 7.5 | 7.5 |
| Other surfactants | 2.95 | 5.74 | 4.18 | 6.18 | 4 | 4 |
| Layered silicate | 2.0 | — | 2.0 | — | — | — |

| | | | | | | |
|---|---|---|---|---|---|---|
| Zeolite | 7 | — | 2 | — | 2 | 2 |
| Citric Acid | 3 | 5 | 3 | 4 | 2.5 | 3 |
| Sodium Carbonate | 15 | 20 | 14 | 20 | 23 | 23 |
| Silicate | 0.08 | — | 0.11 | — | — | — |
| Soil release agent | 0.75 | 0.72 | 0.71 | 0.72 | — | — |
| Acrylic Acid/Maleic Acid Copolymer | 1.1 | 3.7 | 1.0 | 3.7 | 2.6 | 3.8 |
| Amphiphilic alkoxylated grease cleaning polymer[3] | 0.2 | 0.1 | 0.7 | 0.5 | 0.4 | 1.0 |
| Carboxymethyl cellulose (Finnfix BDA ex CPKelco) | 0.15 | — | 0.2 | — | 1 | — |
| Xyloglucanase* (mg aep/100 g detergent) | 3.1 | 2.34 | 3.12 | 4.68 | 3.52 | 7.52 |
| Other enzyme powders | 0.65 | 0.75 | 0.7 | 0.27 | 0.47 | 0.48 |
| Bleach(es) and bleach activator(s) | 16.6 | 17.2 | 16.6 | 17.2 | 18.2 | 15.4 |
| Sulfate/Water & Miscellaneous | Balance to 100% | | | | | |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

[2]Polyethylenimine (MW = 600) with 20 ethoxylate groups per —NH.

[3]Amphiphilic alkoxylated grease cleaning polymer is a polyethylenimine (MW = 600) with 24 ethoxylate groups per —NH and 16 propoxylate groups per —NH

[4]Reversible Protease inhibitor of structure:

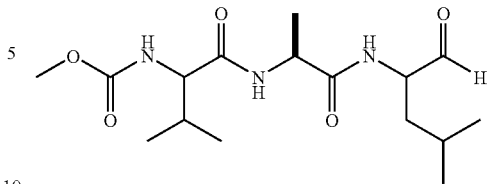

*Remark: all enzyme levels expressed as % enzyme raw material, except for xyloglucanase where the level is given in mg active enzyme protein per 100 g of detergent.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A detergent composition comprising an isolated variant of a parent xyloglucanase, the variant comprising an alteration of the parent xyloglucanase at three or more positions selected from the group consisting of position number 68, 92, 118, 129, 156, 200, and 331, which position corresponds to a position in amino acid sequence SEQ ID NO:3 and wherein:
   a) the alteration(s) are
      i) an insertion of an amino acid downstream of the amino acid which occupies the position, and/or
      ii) deletion of the amino acid which occupies the position, and/or
      iii) a substitution of the amino acid which occupies the position with a different amino acid;
   b) the variant comprises an amino acid sequence having at least 85% identity to the amino acid sequence of the parent xyloglucanase of SEQ ID NO: 3; and
   c) the variant has xyloglucanase activity.

2. The composition of claim 1, wherein the variant comprises one or more of the following combinations of alterations:
   K13A+Q68H+T92V+K118A+Q137E+R156Y+G200P;
   Q68H+G200P+N331F;
   Q68H+K118A+K129A+R156Y+G200P+N331F;
   Q68H+K118A+R156V+G200P+N331F;
   Q68H+K118A+R156Y+H193T+D366H;
   Q68H+K118R+R156F,Y;
   Q68H+K118R+R156Y+G200P;
   Q68H+K118S+R156F+G200P+G274D+N331F;
   Q68H+K129A,T+R156K+G200P+N331F;
   Q68H+R156F,V,Y+G200P+N331F;
   Q68H+R156Y+H193T+G200P+M310V;
   Q68H+S76W+T92V+K118A+Q137E+R156Y+G200P+N331F;
   Q68H+T92A,D,I,S,V,Y+K118A+K129A+R156Y+G200P+N331F;
   Q68H+T92N+D97N+K118A+K129A+R156Y+G200P+N331F;
   Q68H+T92S+K118A+K129A+R156Y+G200P+G274D+N331F;
   Q68H+T92V+G200P+M310V;
   Q68H+T92V+G200P+M310V+N331F;
   Q68H+T92V+K118A+K129A+Q137E+R156Y+G200P+A224P+N331F;
   Q68H+T92V+K118A+K129A+Q137E+R156Y+G200P+N331F;
   Q68H+T92V+K118A+K129A+Q137E+R156Y+H193T;
   Q68H+T92V+K118A+K129A+Q137E+R156Y+H193T+D366H;
   Q68H+T92V+K118A+K129A+Q137E+R156Y+H193T+G200P+M310V+E446K;
   Q68H+T92V+K118A+K129A+Q137E+R156Y+H193T+N331H,K,Q;
   Q68H+T92V+K118A+K129A+R156Y+H193T;
   Q68H+T92V+K118A+K129A+R156Y+H193T+D366H;
   Q68H+T92V+K118A+K129A+R156Y+H193T+G200P+M310V;
   Q68H+T92V+K118A+Q137E+N140F+R156Y+G200P+K470T;
   Q68H+T92V+K118A+Q137E+R156Y+G200P+D324N;
   Q68H+T92V+K118A+Q137E+R156Y+G200P+K470T;
   Q68H+T92V+K118A+Q137E+R156Y+G200P+M310L;
   Q68H+T92V+K118A+Q137E+R156Y+G200P+N331F;
   Q68H+T92V+K118A,R+R156Y,F;

Q68H+T92V+K118A+S123P,T+K129A+Q137E+
   R156Y+G200P+N331F;
Q68H+T92V+K118R+R156Y+H193T+D366H;
Q68H+T92V+R156F+G200P+M310V+S484C;
Q68H+T92V+R156F,V,Y+G200P+M310V;
Q68H+T92V+R156F,V,Y+G200P+M310V+N331F;
Q68H+T92V+R156F,Y+H193T;
Q68H+T92V+R156F,Y+H193T+D366H;
Q68H+T92V+R156F,Y+H193T+G200P+M310V;
Q68H+T92V+R156Y;
G78A+K118A++K129A+R156Y;
G78A+K118A+K129A+R156Y;
G78A+K118A+K129A+R156Y+G200P+N331F;
G78A+K118A+K129A+R156Y+K169A;
G78A+T92V+K118A+K129A+R156Y;
G78A+T92V+K118A+K129A+R156Y+G200P+N331F;
G78A+T92V+K118A+K129A+R156Y+K169A;
T92V+K118A+K129A+Q137E+R156Y+G200P+
   N331F;
T92V+K118A+K129A+R156Y;
T92V+K118A+K129A+R156Y+G200P+N331F;
T92V+K118A+K129A+R156Y+H164N+G200P+
   N331F;
T92V+K129A+R156Y;
K118A+K129A+F146L+R156Y+G200P+N331F;
K118A+K129A+Q137E+R156Y+G200P+N331F;
K118A+K129A+R156Y;
K118A+K129A+R156Y+A224P;
K118A+K129A+R156Y+G200P;
K118A+K129A+R156Y+G200P+M310V+N331F;
K118A+K129A+R156Y+G200P+N331F;
K118A+K129A+R156Y+G200P+N331F+N3991;
K118A+K129A+R156Y+K169A+G200P+N331F;
K118A+K129A+R156Y+K470T;
K118A+R156Y+G200P.

3. The composition according to claim 1, wherein the variant further comprises an alteration at one or more of the positions corresponding position 123, position 137, position 193, or position 76, which position corresponds to a position in amino acid sequence SEQ ID NO: 3.

4. The composition according to claim 1, wherein the variant comprises a substitution at position 68 and two or more substitutions at positions 92, 118, 129, 156, 200 and 331, and wherein the variant further comprises one or more substitutions at one or more additional positions, selected from the group consisting of position number 123, 137, 193, 83, 149, 34, 340, 332, 9, 76, 310, 324, 498, 395 and 366.

5. The composition according to claim 1, wherein the variant comprises a substitution at position 156 and two or more substitutions at positions 68, 92, 118, 129, 200 and 331, and wherein the variant further comprises one or more substitutions at one or more additional positions, selected from the group consisting of position number 10, 13, 14, 19, 37, 78, 123, 137, 139, 140, 147, 159, 164, 165, 169, 176, 177, 179, 183, 204, 211, 222, 224, 244, 247, 249, 259, 267, 268, 269, 275, 288, 299, 301, 302, 303, 310, 324, 328, 366, 380, 383, 384, 389, 406, 409, 415, 436, 443, 445, 449, 450, 454, 455, 456, 461, 470 and 507.

6. The composition according to claim 5, wherein the variant comprises substitutions at position 129 and position 156.

7. The composition according to claim 1, wherein the variant comprises three or more substitutions selected from the group consisting of: Q68H,N,L; T92V,I,A,S; K118A,R; K129T,A,S; R156Y,F,V,I,K,W,L,M; G200P,E,S,D; and N331F,C, and wherein the variant further comprises one or more substitutions at one or more additional positions selected from the group consisting of S123P,T; Q137E; H193T,S,D; A83E; Q149E; L34F,I,V; R340T,N; S332P; T9D; S76W,V,I,K,R,T; M310I,V,L; D324N; G498A,D; D395G and D366H.

8. The composition according to claim 1, wherein the variant comprises one or more of the following combinations of substitutions:
K129A+R156Y+G200P
Q68HK118R+R156F
Q68H+R156F+G200P+N331F
Q68H+T92V+K118A+R156Y
K118A+K129A+R156Y+G200P+N331F
G78A+T92V+K118A+K129A+R156Y
Q68H+K129T+R156K+G200P+N331F
K118A+K129A+R156Y+K169A+G200P+N331F
T92V+K118A+K129A+R156Y+G200P+N331F
G78A+K118A+K129A+R156Y+G200P+N331F
G78A+T92V+K118A+K129A+R156Y+K169A
Q68H+T92V+Q137E+R156Y+G200P+N331F
Q68H+T92V+K118A+Q137E+R156Y+N331F
Q68H+T92V+R156Y+G200P+M310V+N331F
Q68H+K118A+K129A+R156Y+G200P30 N331F
Q68H+T92V+K118A+K129A+R156Y+G200P30
   N331F
Q68H+T92V+K118A+Q137E+R156Y+G200P+N331F
Q68H+T92V+K118A+K129A+R156Y+H193T+D366H
Q68H+T92V+K118A+K129A+Q137E+R156Y+
   H193T+D366H
Q68H+T92V+K118A+K129A+Q137E+R156Y+
   G200P+N331F
Q68H+T92V+K118A+S123P,T+K129A+Q137E+
   R156Y+G200P+N331F
Q68H+T92V+K118A+K129A+Q137E+R156Y+
   G200P+A224P+N331F.

9. The composition according to claim 1, wherein the variant has improved chemical stability compared to the parent xyloglucanase.

10. The composition according to claim 9, wherein the improved chemical stability results in improved detergent stability.

11. A composition according to claim 1, wherein the composition is a liquid laundry detergent composition.

12. A composition according to claim 1, wherein the composition comprises one or more ingredients selected from:
(a) amphiphilic alkoxylated grease cleaning polymer;
(b) random graft co-polymer, wherein the random graft co-polymer comprises:
   (i) hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and
   (ii) hydrophobic side chain(s) selected from the group consisting of: $C_4$-$C_{25}$ alkyl group, polypropylene, polybutylene, vinyl ester of a saturated $C_1$-$C_6$ monocarboxylic acid, $C_1$-$C_6$ alkyl ester of acrylic or methacrylic acid, and mixtures thereof;
(c) a compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n=from 20 to 30, and x=from 3 to 8, or sulphated or sulphonated variants thereof.

13. A composition according to claim 1, wherein the composition comprises a perfume microcapsule.

14. A composition according to claim 1, wherein the composition comprises a fabric hueing agent.

15. A composition according to claim 1, wherein the composition comprises from about 0.1% to about 5% by weight of the composition, of a calcium sequestrant having a conditional stability constant at pH 8 of greater than about 4.

16. A composition according to claim 1, wherein the composition is in solid form.

* * * * *